US012295850B2

(12) United States Patent
Moseley et al.

(10) Patent No.: US 12,295,850 B2
(45) Date of Patent: May 13, 2025

(54) SYSTEMS, METHODS, AND DEVICES FOR LATERAL AND POSTERIOR SACROILIAC JOINT FUSION

(71) Applicant: Spinal Simplicity, LLC, Overland Park, KS (US)

(72) Inventors: Todd Moseley, Olathe, KS (US); Colton McQuinn, Grandview, MO (US); Luke Luallin, Fairway, KS (US); Melissa Frock, Lenexa, KS (US); Jeffrey David Lee, Prairie Village, KS (US); Nick Furman, Raymore, MO (US); Adam Frock, Lenexa, KS (US); Adam Rogers, Olathe, KS (US); Christian Aragonez, Kansas City, MO (US); Jeff Slover, Lee's Summit, MO (US)

(73) Assignee: Spinal Simplicity, LLC, Overland Park, KS (US)

( * ) Notice: Subject to any disclaimer, the term of this patent is extended or adjusted under 35 U.S.C. 154(b) by 0 days.

(21) Appl. No.: 18/504,635

(22) Filed: Nov. 8, 2023

(65) Prior Publication Data
US 2024/0189108 A1 Jun. 13, 2024

Related U.S. Application Data

(60) Provisional application No. 63/498,649, filed on Apr. 27, 2023, provisional application No. 63/576,430, filed on Dec. 13, 2022.

(51) Int. Cl.
*A61F 2/28* (2006.01)
*A61B 17/16* (2006.01)
(Continued)

(52) U.S. Cl.
CPC ...... *A61F 2/30988* (2013.01); *A61B 17/1671* (2013.01); *A61F 2/30771* (2013.01);
(Continued)

(58) Field of Classification Search
CPC ............ A61B 17/7065; A61B 17/7062; A61B 17/7055; A61F 2002/30622;
(Continued)

(56) References Cited

U.S. PATENT DOCUMENTS 8,388,667 B2   3/2013   Reiley et al.
8,882,818 B1   11/2014  Vestgaarden
(Continued)

FOREIGN PATENT DOCUMENTS

WO   2019152737 A1   8/2019
WO   2023056347 A1   4/2023
(Continued)

OTHER PUBLICATIONS

PCT Patent Application PCT/US2023/082673 International Search Report and The Written Opinion, issued Mar. 21, 2024.
(Continued)

*Primary Examiner* — Javier G Blanco
(74) *Attorney, Agent, or Firm* — Erise IP, P.A.

(57) ABSTRACT

Systems, methods, and devices for sacroiliac (SI) joint fusion are described. At least one posterior SI implant and at least one lateral SI implant may be implanted. The posterior SI implant may be placed in the intra-articular region, and the lateral SI implant may transfix the SI joint such that the lateral SI implant passes through the ilium, across the SI joint, and into the sacrum. The lateral SI implant may compress the SI joint. The lateral SI implant may be inserted through a window in the posterior SI implant to interlock the two implants.

20 Claims, 30 Drawing Sheets

(51) Int. Cl.
*A61F 2/30* (2006.01)
*A61F 2/46* (2006.01)

(52) U.S. Cl.
CPC .......... *A61F 2002/2835* (2013.01); *A61F 2002/30405* (2013.01); *A61F 2002/30537* (2013.01); *A61F 2002/30579* (2013.01); *A61F 2002/30593* (2013.01); *A61F 2002/30622* (2013.01); *A61F 2002/30772* (2013.01); *A61F 2002/3085* (2013.01); *A61F 2002/30884* (2013.01); *A61F 2002/30995* (2013.01); *A61F 2002/4627* (2013.01); *A61F 2002/4635* (2013.01)

(58) Field of Classification Search
CPC .. A61F 2002/30405; A61F 2002/30995; A61F 2002/30884; A61F 2002/3085
See application file for complete search history.

(56) References Cited

U.S. PATENT DOCUMENTS

| | | | |
|---|---|---|---|
| 9,198,678 B2 | 12/2015 | Frey et al. |
| 9,375,243 B1 | 6/2016 | Vestgaarden |
| 9,522,028 B2 | 12/2016 | Warren et al. |
| 9,757,164 B2 | 9/2017 | Hess et al. |
| 9,820,789 B2 | 11/2017 | Reiley |
| 9,839,448 B2 | 12/2017 | Reckling et al. |
| 9,861,399 B2 | 1/2018 | Rogers et al. |
| 9,895,176 B2 | 2/2018 | Vestgaarden |
| 9,907,581 B2 | 3/2018 | Hess et al. |
| 10,064,728 B2 | 9/2018 | Donner et al. |
| 10,166,056 B2 | 1/2019 | Warren et al. |
| 10,179,014 B1 | 1/2019 | Menmuir et al. |
| 10,179,015 B2 | 1/2019 | Lavigne et al. |
| 10,251,688 B2 | 4/2019 | Asfora |
| 10,285,739 B2 | 5/2019 | Frock et al. |
| 10,299,837 B2 | 5/2019 | Redmond et al. |
| 10,426,621 B2 | 10/2019 | Vickers et al. |
| 10,588,676 B2 | 3/2020 | Kang et al. |
| 10,595,917 B2 | 3/2020 | Loftus |
| 10,813,679 B2 | 10/2020 | Lanois et al. |
| 10,842,448 B2 | 11/2020 | Shoup et al. |
| 10,940,008 B2 | 3/2021 | Patel |
| 10,980,643 B2 | 4/2021 | Castro |
| 11,172,939 B2 | 11/2021 | Donner et al. |
| 11,304,738 B2 | 4/2022 | Loftus |
| 11,452,532 B2 | 9/2022 | Asfora et al. |
| 11,504,166 B2 | 11/2022 | Kraus |
| 11,534,310 B2 | 12/2022 | Frock et al. |
| 11,628,004 B2 | 4/2023 | Lanois et al. |
| 11,744,623 B2 | 9/2023 | Redmond et al. |
| 11,883,077 B2 | 1/2024 | Kaufmann et al. |
| 11,883,078 B2 | 1/2024 | Schumacher et al. |
| 11,992,409 B2 | 5/2024 | Patel |
| 2015/0012051 A1* | 1/2015 | Warren .............. A61B 17/8685 606/310 |
| 2016/0120661 A1* | 5/2016 | Schell ................ A61B 17/8605 623/17.11 |
| 2017/0189079 A1* | 7/2017 | Frock ................. A61B 17/8891 |
| 2017/0258498 A1 | 9/2017 | Redmond et al. |
| 2020/0085474 A1 | 3/2020 | Harshman et al. |
| 2020/0281729 A1* | 9/2020 | Schifano ........... A61B 17/8875 |
| 2021/0212833 A1 | 7/2021 | Chin et al. |
| 2022/0175548 A1 | 6/2022 | Frock et al. |
| 2022/0226027 A1 | 7/2022 | Rogers et al. |
| 2022/0304672 A1* | 9/2022 | Kalhorn ................. A61B 17/86 |
| 2022/0354654 A1* | 11/2022 | Lewis ................... A61F 2/4601 |
| 2023/0088125 A1 | 3/2023 | Frock et al. |
| 2023/0181322 A1 | 6/2023 | Greenhalgh et al. |
| 2023/0240725 A1 | 8/2023 | Frock et al. |
| 2023/0320764 A1 | 10/2023 | Slover et al. |
| 2023/0329761 A1 | 10/2023 | Rogers et al. |
| 2023/0329871 A1 | 10/2023 | Greenhalgh et al. |
| 2023/0390078 A1* | 12/2023 | Bergey ................ A61B 17/846 |
| 2024/0091026 A1 | 3/2024 | Arnold et al. |
| 2024/0115296 A1 | 4/2024 | Huffmann et al. |

FOREIGN PATENT DOCUMENTS

| | | |
|---|---|---|
| WO | 2023137124 A2 | 7/2023 |
| WO | 2024098047 A1 | 5/2024 |
| WO | 2024098048 A1 | 5/2024 |
| WO | 2024098049 A2 | 5/2024 |
| WO | 2024119118 A1 | 6/2024 |

OTHER PUBLICATIONS

PCT Patent Application PCT/US2023/082670 International Search Report and The Written Opinion, issued Aug. 8, 2024.
U.S. Appl. No. 63/249,945, filed Sep. 29, 2021.

\* cited by examiner

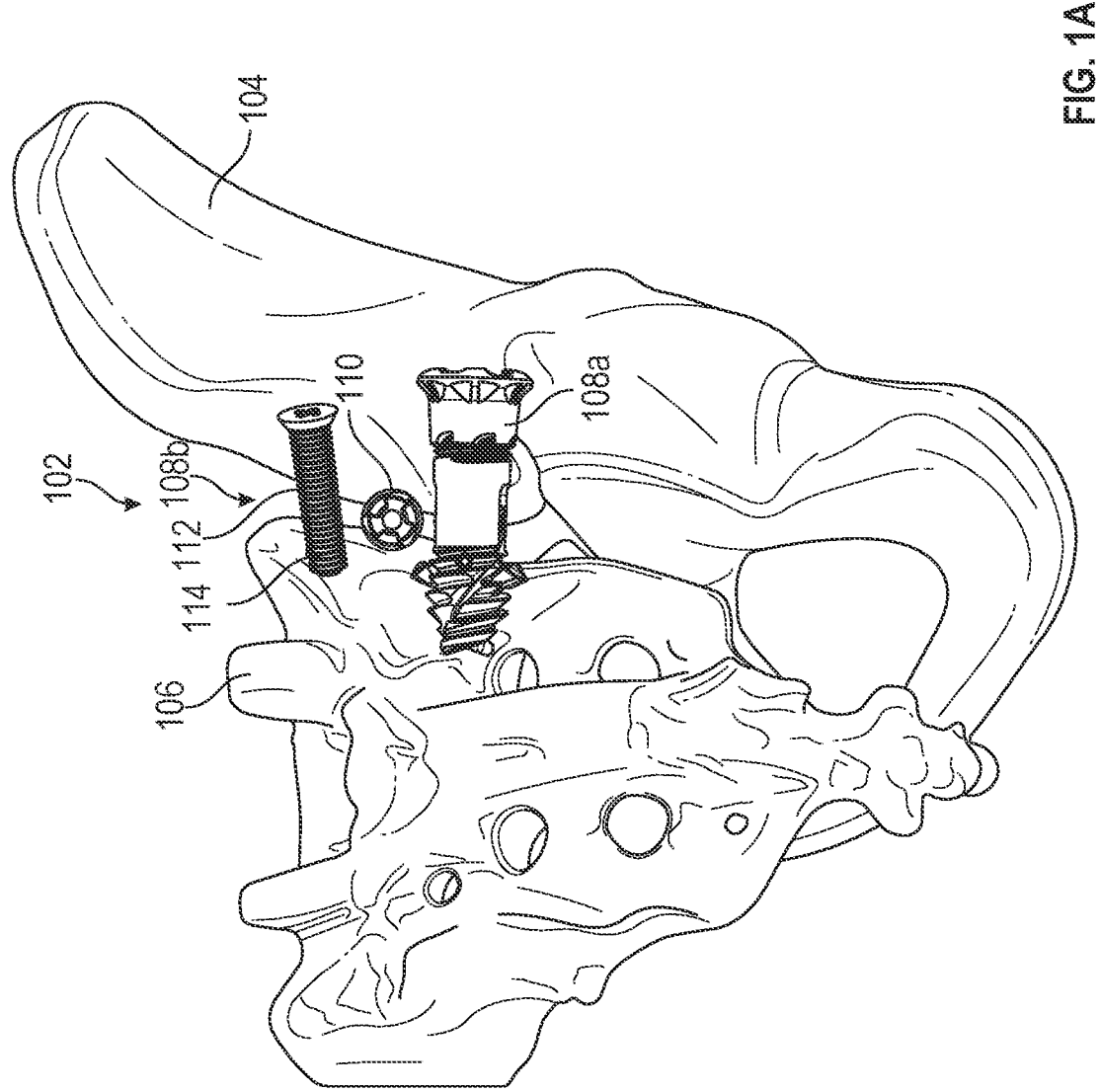

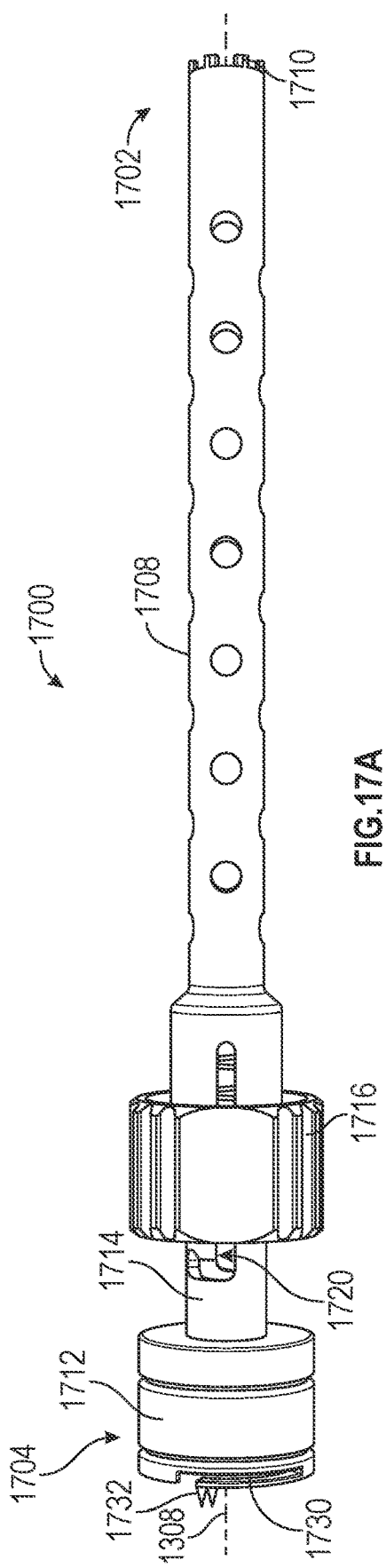
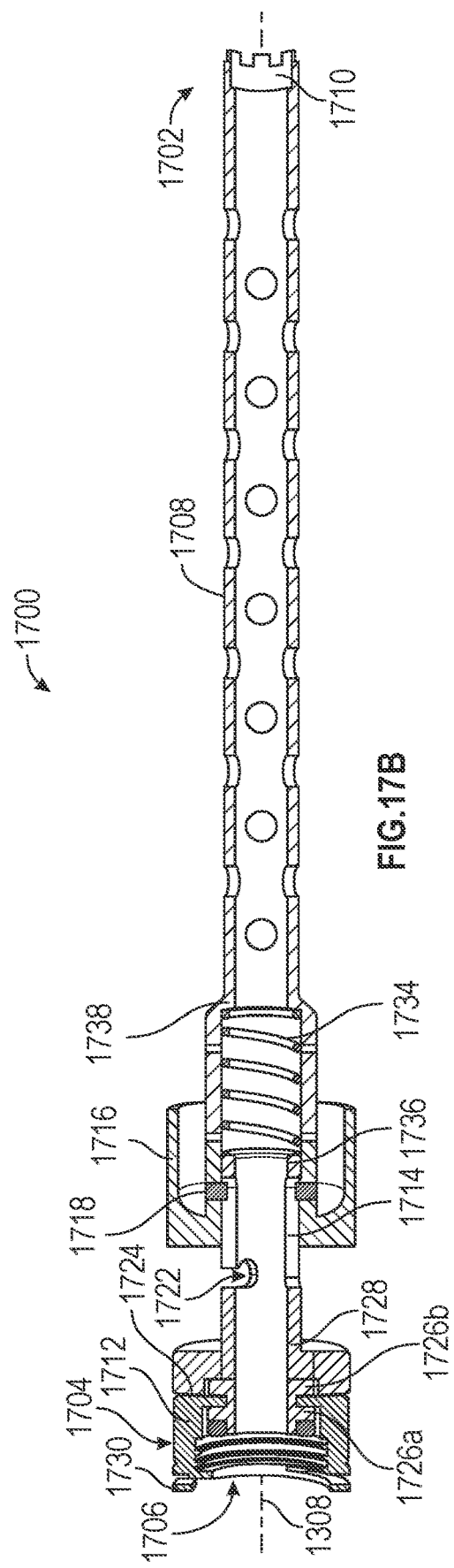
FIG. 17A
FIG. 17B

SYSTEMS, METHODS, AND DEVICES FOR LATERAL AND POSTERIOR SACROILIAC JOINT FUSION

CROSS-REFERENCE TO RELATED APPLICATIONS

This non-provisional patent application claims prior benefit, with regard to all subject matter, of U.S. Provisional Patent Application No. 63/576,430, filed Dec. 13, 2022, and entitled "SACROILIAC JOINT FUSION IMPLANTS AND METHODS"; and U.S. Provisional Patent Application No. 63/498,649, filed Apr. 27, 2023, and entitled "SACROILIAC JOINT FUSION IMPLANTS, INSERTION INSTRUMENTS, AND METHODS".

This non-provisional patent application shares certain common subject matter with U.S. Application Ser. No. 18/504,856, filed Nov. 8, 2023, and entitled "SACROILIAC JOINT FUSION IMPLANTS, INSERTION INSTRUMENTS, AND METHODS"; and U.S. Application Ser. No. 18/504,480, filed Nov. 8, 2023, and entitled "BONY FUSION IMPLANT, INSERTION INSTRUMENT, AND METHODS". The above-identified applications are hereby incorporated by reference in their entirety.

TECHNICAL FIELD

Embodiments of the present disclosure generally relate to systems, devices, and methods for bony fusion. More specifically, embodiments of the present disclosure relate to minimally invasive lateral and posterior sacroiliac (SI) joint fusion systems, methods, and devices.

RELATED ART

The spine consists of a column of twenty-four vertebrae that extends from the skull to the hips. The most inferior lumbar vertebra (L5) connects to the sacrum, which is a large bone that is formed by the fusion of the sacral vertebrae. On each side of the sacrum is an ilium, and the sacrum articulates with each ilium to form two sacroiliac (SI) joints. The SI joints play a significant role in absorbing impact from walking, lifting, and other movements.

When the ligaments or bony surfaces are damaged (e.g., due to trauma, arthritis, or other conditions), the SI joints can be a source of intense pain that can radiate into the leg. SI joint pain can also occur after a patient undergoes other spinal fusion procedures. Inflammation in the SI joints is known as sacroiliitis. Sacroiliitis can be treated via non-surgical and surgical methods. Sacroiliitis may be treated surgically via an SI joint fusion procedure that uses an implant device to provide stability. The SI joints experience significant micromotions that make SI joint fusion difficult. Causing compression across the SI joint can reduce these micromotions; however, typical SI joint fusion devices fail to provide adequate compression across the SI joint to enhance fusion of the joint and/or require multiple implants to be inserted to provide adequate compression across the SI joint.

Posterior SI implants may be inserted in the intra-articular region of the SI joint and interposed between the sacrum and the ilium. By interposing the implant, loads can be transferred to the implant, which relieves stresses on the joint. Further, posterior SI implants obviate the risk of contacting the sacral nerves that are associated with lateral SI implants. Typical posterior SI joint implants are not made out of metal, leading to lower strength, and are deficient in promoting bone ingrowth.

SUMMARY

Embodiments of the present disclosure are generally directed to systems, methods, and devices for a minimally invasive surgical procedure in which at least one lateral SI implant is implanted to transfix the SI joint and at least one posterior SI implant is inserted in the intra-articular region of the joint. The lateral SI implant may compress the SI joint and may include a distal anchor for compressing the sacrum and a proximal anchor for compressing the ilium. The posterior SI implant may be externally threaded and engage with the sacrum and the ilium. Inserting both a lateral SI implant and a posterior SI implant can allow for the lateral SI implant to compress the sacrum and ilium onto the posterior SI implant, which can improve the fixation provided by the posterior SI implant, thereby improving the SI joint fusion. In some embodiments, the lateral SI implant and the posterior SI implant are interlocked. The posterior SI implant may comprise a window through which the lateral SI implant can be inserted to interlock the two implants.

In some embodiments, the techniques described herein relate to a method for sacroiliac (SI) joint fusion, including: providing instructions including: make a first incision on a patient to provide posterior access to the SI joint of the patient; insert, through the first incision and via a posterior approach, a posterior SI implant into the SI joint such that the posterior SI implant engages with both a sacrum and an ilium of the patient, wherein the posterior SI implant includes a window extending through a body of the posterior SI implant; make a second incision on the patient to provide lateral access to the SI joint; and insert, through the second incision, through the window of the posterior SI implant and via a lateral approach, a lateral SI implant across the SI joint such that a distal end of the lateral SI implant is at least partially within the sacrum of the patient and a proximal end of the lateral SI implant is engaged with the ilium of the patient.

In some embodiments, the techniques described herein relate to a method, wherein the instructions further include: apply compression across the SI joint and to the posterior SI implant with the lateral SI implant.

In some embodiments, the techniques described herein relate to a method, wherein the lateral SI implant includes a distal anchor at the distal end and a proximal anchor at the proximal end, wherein both the distal anchor and the proximal anchor are configured to provide the compression across the SI joint.

In some embodiments, the techniques described herein relate to a method, wherein the distal anchor includes a pair of deployable wings housed within the lateral SI implant in a closed configuration and deployed from within the lateral SI implant in an open configuration.

In some embodiments, the techniques described herein relate to a method, wherein the instructions further include: inject bone graft into the lateral SI implant or the posterior SI implant.

In some embodiments, the techniques described herein relate to a method, wherein the bone graft is injected through an insertion instrument configured to insert at least one of the lateral SI implant or the posterior SI implant.

In some embodiments, the techniques described herein relate to a method, wherein inserting the lateral SI implant includes self-drilling the lateral SI implant through the ilium and into the sacrum.

In some embodiments, the techniques described herein relate to a method for sacroiliac (SI) joint fusion, including: providing instructions including: make a first incision on a patient to provide posterior access to the SI joint of the patient; insert, via a posterior approach, using a first insertion instrument, and through the first incision, a posterior SI implant into the SI joint such that the posterior SI implant engages with both a sacrum and an ilium of the patient, wherein the posterior SI implant includes an externally threaded body and is cannulated along a longitudinal axis; make a second incision on the patient to provide lateral access to the SI joint; insert, via a lateral incision, using a second insertion instrument, and through the second incision, a lateral SI implant across the SI joint, wherein the lateral SI implant includes: a main body; a pair of wings at a distal end of the main body, the pair of wings selectively positioned in an open configuration and a closed configuration; and an adjustable compressive body coupled to a proximal end of the main body and configured to adjust an amount of compression across the SI joint; and apply compression across the SI joint and to the posterior SI implant with the lateral SI implant.

In some embodiments, the techniques described herein relate to a method, wherein the first incision and the second incision are minimally invasive incisions having a length of less than two inches.

In some embodiments, the techniques described herein relate to a method, wherein when the lateral SI implant is inserted, the pair of wings are within the sacrum and the adjustable compressive body at least partially protrudes from the ilium.

In some embodiments, the techniques described herein relate to a method, wherein the instructions further include: insert bone graft into the posterior SI implant through the first insertion instrument and into the lateral SI implant through the second insertion instrument.

In some embodiments, the techniques described herein relate to a method, wherein the instructions further include: thread the adjustable compressive body along the proximal end of the main body to adjust the amount of compression applied by the adjustable compressive body.

In some embodiments, the techniques described herein relate to a method, wherein the instructions further include: using the second insertion instrument, retract the lateral SI implant to anchor the pair of wings against cortical bone of the sacrum.

In some embodiments, the techniques described herein relate to a method for sacroiliac (SI) joint fusion, including: providing instructions including: make a first incision on a patient to provide posterior access to the SI joint of the patient; insert, via a posterior approach and through the first incision, a posterior SI implant into the SI joint such that the posterior SI implant engages with both a sacrum and an ilium of the patient; make a second incision on the patient to provide lateral access to the SI joint; insert, via a lateral approach and through the second incision, a lateral SI implant across the SI joint such that a distal end of the lateral SI implant is at least partially within the sacrum of the patient and a proximal end of the lateral SI implant at least partially protrudes from the ilium of the patient; and apply compression across the SI joint with the lateral SI implant.

In some embodiments, the techniques described herein relate to a method, wherein each of the first incision and the second incision are minimally invasive incisions having a length of less than two inches.

In some embodiments, the techniques described herein relate to a method, wherein the lateral SI implant is a first lateral SI implant, the posterior SI implant is a first posterior SI implant, and wherein the instructions further include: insert at least one of: a second lateral SI implant or a second posterior SI implant.

In some embodiments, the techniques described herein relate to a method, wherein the second posterior SI implant is inserted superiorly relative to the first posterior SI implant.

In some embodiments, the techniques described herein relate to a method, wherein the posterior SI implant includes a window therethrough, and wherein inserting the lateral SI implant includes inserting the lateral SI implant through the window of the SI implant.

In some embodiments, the techniques described herein relate to a method, wherein the lateral SI implant includes a distal anchor configured to compress against cortical bone of the sacrum and a proximal anchor configured to compress against the ilium to compress the posterior SI implant.

In some embodiments, the techniques described herein relate to a method, wherein at least one of the posterior SI implant or the lateral SI implant includes a self-drilling distal end.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current present disclosure will be apparent from the following detailed description of the embodiments and the accompanying drawing figures.

BRIEF DESCRIPTION OF THE FIGURES

Embodiments of the present disclosure are described in detail below with reference to the attached drawing figures, wherein:

FIG. 1A illustrates a first view of the SI joint with lateral and posterior SI implants inserted for some embodiments;

FIGS. 17A-17B illustrate a compressive body subassembly of the second insertion instrument for some embodiments;

Figure 1B:
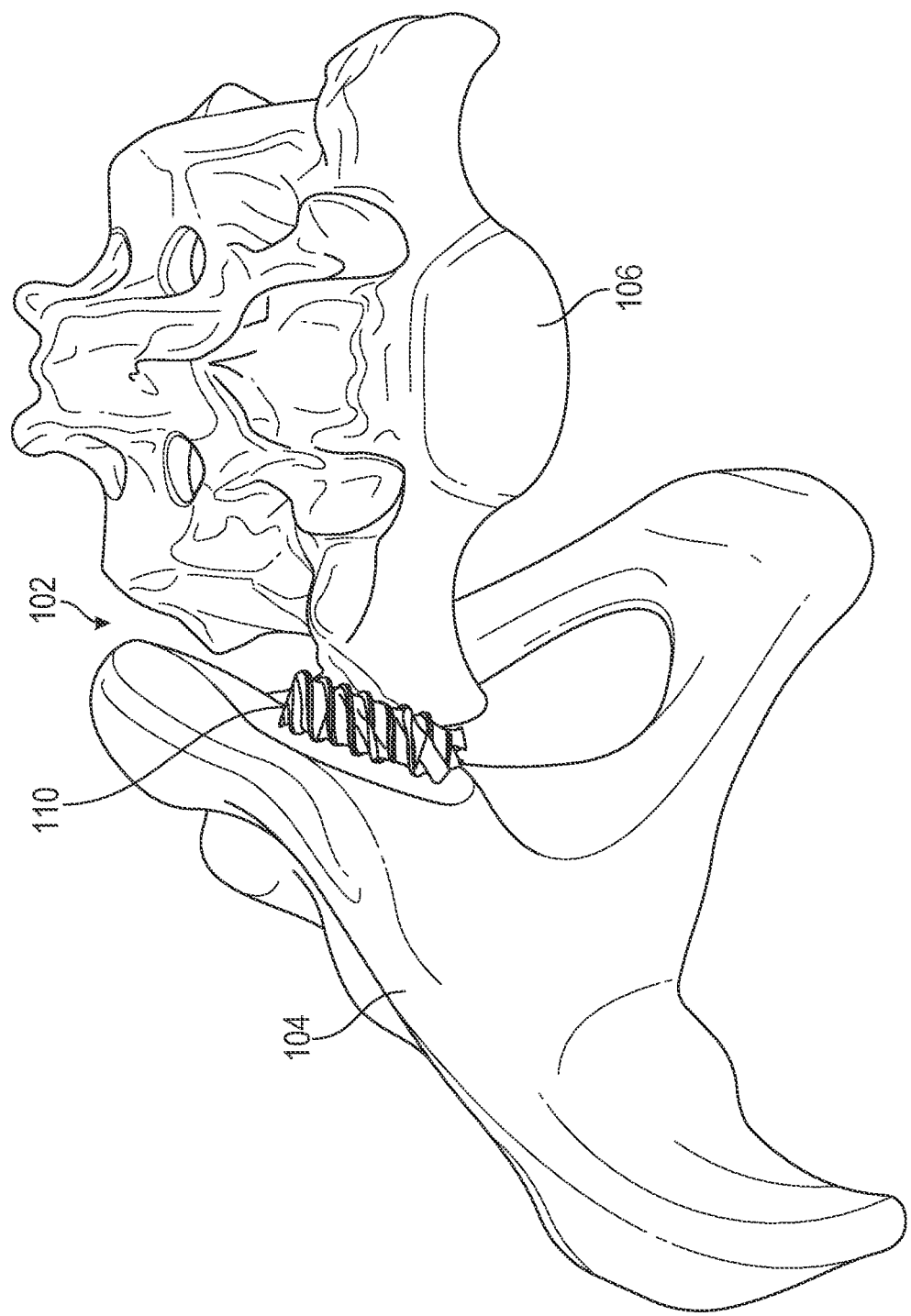
FIG. 1B illustrates a second view of the SI joint showing the posterior SI implant for some embodiments.

The drawing figures do not limit the present disclosure to the specific embodiments disclosed and described herein. The drawings are not necessarily to scale, emphasis instead being placed upon clearly illustrating the principles of the present disclosure.

DETAILED DESCRIPTION

The subject matter of the present disclosure is described in detail below to meet statutory requirements; however, the description itself is not intended to limit the scope of claims. Rather, the claimed subject matter might be embodied in other ways to include different steps or combinations of steps similar to the ones described in this document, in conjunction with other present or future technologies. Minor variations from the description below will be understood by one skilled in the art and are intended to be captured within the scope of the claims. Terms should not be interpreted as implying any particular ordering of various steps described unless the order of individual steps is explicitly described.

The following detailed description of embodiments of the present disclosure references the accompanying drawings that illustrate specific embodiments in which the present disclosure can be practiced. The embodiments are intended to describe aspects of the present disclosure in sufficient detail to enable those skilled in the art to practice the present disclosure. Other embodiments can be utilized and changes can be made without departing from the scope of the present disclosure. The following detailed description is, therefore, not to be taken in a limiting sense. The scope of embodiments of the present disclosure is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate reference to "one embodiment" "an embodiment", or "embodiments" in this description do not necessarily refer to the same embodiment and are also not mutually exclusive unless so stated and/or except as will be readily apparent to those skilled in the art from the description. For example, a feature, structure, or act described in one embodiment may also be included in other embodiments but is not necessarily included. Thus, the technology can include a variety of combinations and/or integrations of the embodiments described herein.

Embodiments of the present disclosure are generally directed to systems, methods, and devices for sacroiliac (SI) joint fusion. A SI joint fusion method is provided in which at least one lateral SI implant and at least one posterior SI implant are inserted. The lateral SI implant may transfix the SI joint such that the lateral SI implant passes through the ilium, across the SI joint, and into the sacrum. The posterior SI implant (also referred to as an in-line SI implant) may be placed in the intra-articular region of the SI joint such that the posterior SI implant does not transfix the SI joint. The compression across the SI joint provided by the lateral SI implant may improve the fixation provided by the posterior SI implant, thereby improving fixation of the SI joint.

The lateral SI implant may interlock with the posterior SI implant. The posterior SI implant may include an opening or window extending through a body portion of the implant. To interlock the two implants, after inserting the posterior SI implant, the lateral SI implant may be inserted across the SI joint and through the window of the posterior SI implant. The lateral SI implant may compress the SI joint, and the interlocking may improve compression across the SI joint about the posterior SI implant, which may improve fixation, bone ingrowth, bone ongrowth, reduce migration of the posterior SI implant, reduce micromotions in the SI joint, create fusion, among other benefits.

In some embodiments, the lateral SI implant includes a distal anchor and a proximal anchor. The distal anchor may apply compression to the sacrum, and the proximal anchor may apply compression to the ilium. The distal anchor may include a pair of selectively deployable wings that, when deployed, engage with the cortical bone of the sacrum. The proximal anchor may include a compressive body that is adjustable along a length of the lateral SI implant and may engage with the gluteal surface of the ilium.

In some embodiments, the posterior SI implant comprises a distal section, a proximal section, and a central section between the distal section and the proximal section. The distal section may comprise cutting threads and flutes for self-drilling the implant into bone. The proximal section may be configured to couple to an insertion instrument for the implant. The central section may have a lattice structure through which bone graft may flow to promote bone ingrowth. A solid core region may be located inwards from the lattice structure. The central section may also have openings through the core region to connect the lattice structure to the cannula.

SI Joint Fusion Overview

FIG. 1A illustrates the SI joint 102, ilium 104, and sacrum 106 with lateral SI implants 108a, 108b, and a posterior SI implant 110 implanted in accordance with aspects of the present disclosure. The SI joint 102 is located between the ilium 104 and the sacrum 106 in the pelvic region of the body. As described above, embodiments of the present disclosure involve an SI joint fusion procedure in which one or more lateral SI implants 108a, 108b and one or more posterior SI implants 110 are inserted for fusion of the SI joint 102 (e.g., to treat sacroiliitis).

In some embodiments, a lateral SI implant 108a, 108b is implanted to transfix the SI joint 102 such that the lateral SI implant 108a, 108b passes through the ilium 104, across the SI joint 102, and into the sacrum 106. In some embodiments, the lateral SI implant 108a, 108b is configured to apply compression to the SI joint 102. Applying compression may aid in SI joint fusion and reduce micromotions in the joint space, among other benefits. For example, as discussed below with respect to FIGS. 6A-12, a lateral SI implant 108a may include a distal anchor configured to apply compression to a cortical wall of the sacrum 106 in the lateral direction (see FIG. 12) and a proximal anchor configured to compress the ilium 104 in the medial direction, thereby compressing the SI joint 102.

Along with lateral SI implant 108a that is discussed in further detail below, various other lateral SI implants are considered to be within the scope of the present disclosure. For example, as shown with respect to second lateral SI implant 108b, a screw-type lateral SI implant may be used. Second lateral SI implant 108b may comprise external threads 112 along at least a portion of a body 114 of the implant 108b. In some embodiments, lateral SI implant 108b is non-threaded. While shown as having a rounded distal tip, implant 108b may have a sharp distal tip (e.g., a self-drilling distal tip), or a tip of any other geometry without departing from the scope hereof. Generally, implant 108b may take any geometry and size for transfixing SI joint 102. As another example, lateral SI implant 108b may have a triangular, splined, or wedge shape. Implant 108b may include one or more openings (not shown) for receiving bone graft.

In some embodiments, a single lateral SI implant 108a, 108b is inserted. As discussed further below, it is one advantage of the first lateral SI implant 108a that the distal and proximal anchors can provide sufficient compression such that only a single implant needs to be inserted for SI joint fusion. The surgeon may be able to determine when sufficient compression has been achieved based on feel and by using fluoroscopy imaging, which may visually indicate that the SI joint 102 has been reduced in width. However, in some embodiments, multiple lateral SI implants 108a, 108b may be inserted for the procedure. When multiple lateral SI implants 108a, 108b are inserted, adjacent implants 108a, 108b may be offset in the sagittal plane, the coronal plane, the transverse plane, or any combination thereof. For example, as shown, first lateral SI implant 108a is displaced inferiorly relative to second lateral SI implant 108b. Implanting multiple lateral SI implants 108a, 108b may comprise inserting multiple of the same lateral SI implants 108a, 108b or may include inserting multiple distinct lateral SI implants 108a, 108b. For example, multiple first lateral SI implants 108a may be inserted without implanting any of the second lateral SI implants 108b shown in FIG. 1B. As another example, a first lateral SI implant 108a may be inserted and two second lateral SI implants 108b may also be inserted. Generally, any combination of lateral SI implants 108a, 108b may be inserted without departing from the scope hereof.

Reference is now also made to FIG. 1B, showing a perspective, inferior-looking view of SI joint 102, with lateral SI implants 108a, 108b hidden for the sake of clarity. As shown in FIGS. 1A and 1B, in some embodiments, a posterior SI implant 110 is inserted in the SI joint 102 such that posterior SI implant 110 does not transfix the SI joint 102, i.e., the posterior SI implant 110 is placed in the intra-articular region. In some embodiments, a single posterior SI implant 110 is inserted. In some embodiments, multiple posterior SI implants 110 are inserted. When multiple posterior SI implants 110 are inserted, adjacent posterior SI implants 110 may be offset generally in the medial plane (i.e., a second SI implant 110 may be offset superiorly or inferiorly relative to a first SI implant 110). In some embodiments, adjacent posterior SI implants 110 are offset in the sagittal plane such that different posterior SI implants 110 may be inserted at different depths into the intra-articular space In some embodiments, posterior SI implant 110 is configured has a final position from the posterior-inferior aspect of the articular portion of the joint 102, anterior to the posterior superior iliac spine (PSIS), and posterior to the posterior inferior iliac spine (PIIS), ranging from 0 to 10 mm from the proximal end of SI joint 102.

As previously discussed, the posterior SI implant and the lateral SI implants may be inserted in a single procedure to treat the SI joint 102. In some embodiments, the posterior implants are inserted first, and the lateral SI implants are inserted after the posterior SI implants. In some embodiments, lateral SI implants are inserted before the posterior SI implants. Each implant may be inserted through a minimally invasive incision such that a first minimally invasive incision may be made to provide posterior access to SI joint 102 for inserting the posterior SI implant(s), and a second minimally invasive incision may be made to provide lateral access to SI joint 102 for inserting the lateral SI implant(s). Additional minimally invasive incisions may be made as needed, e.g., to insert additional implants if existing incisions do not provide the requisite access to the implantation site. As discussed in further detail below with respect to FIGS. 5, 18, and 20, the surgical procedure may be conducted under fluoroscopy to provide internal imaging. Once the incisions are made, working channels may be created using dilators, drills, decorticators, rasps, and the like to prepare the SI joint 102 for implantation of the SI implants.

Interlocking Posterior and Lateral SI Implants

Figure 2A:
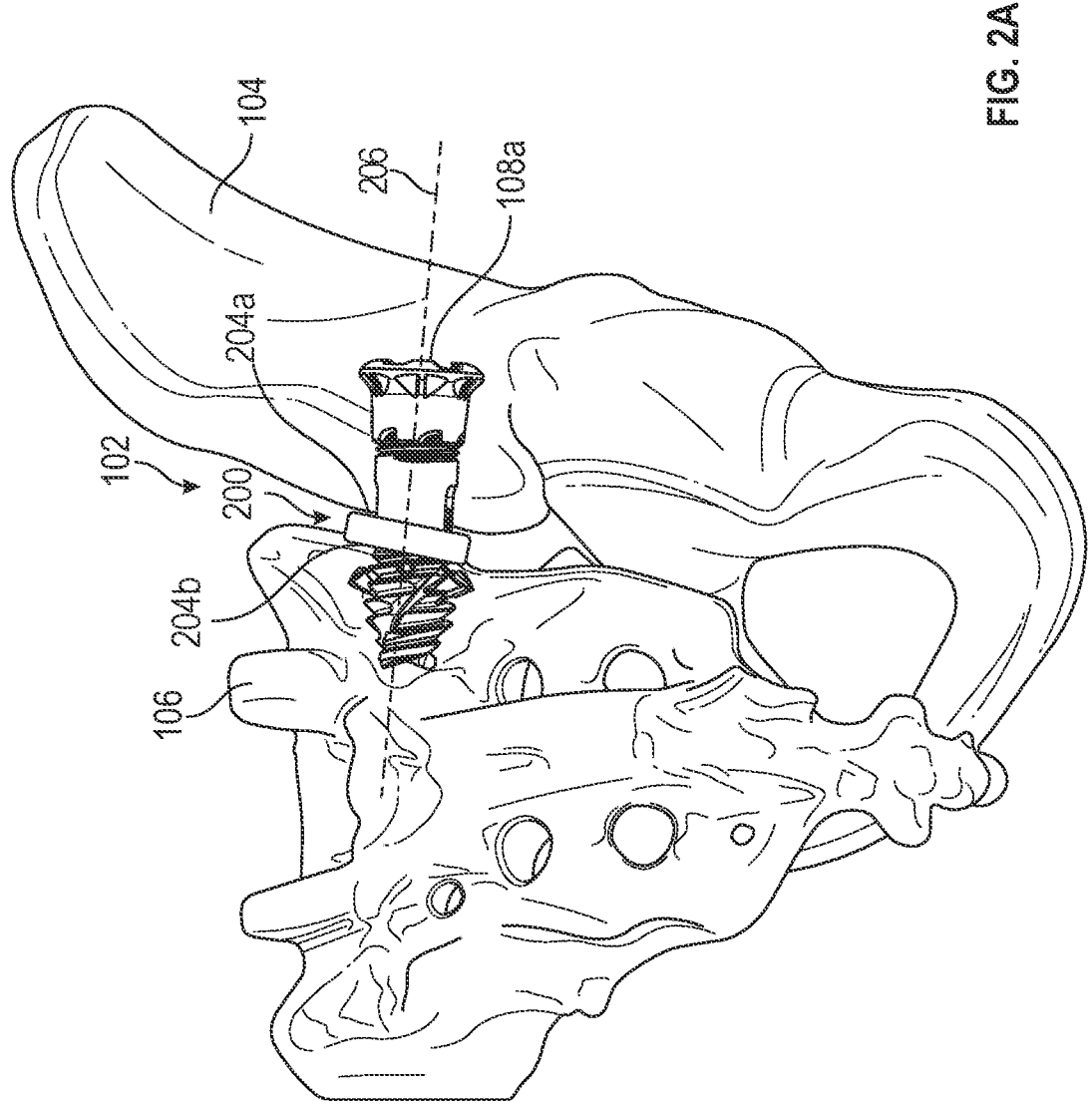
FIGS. 2A and 2B illustrate the SI joint with a lateral SI implant interlocked with a posterior SI implant for some embodiments.
Figure 2B:
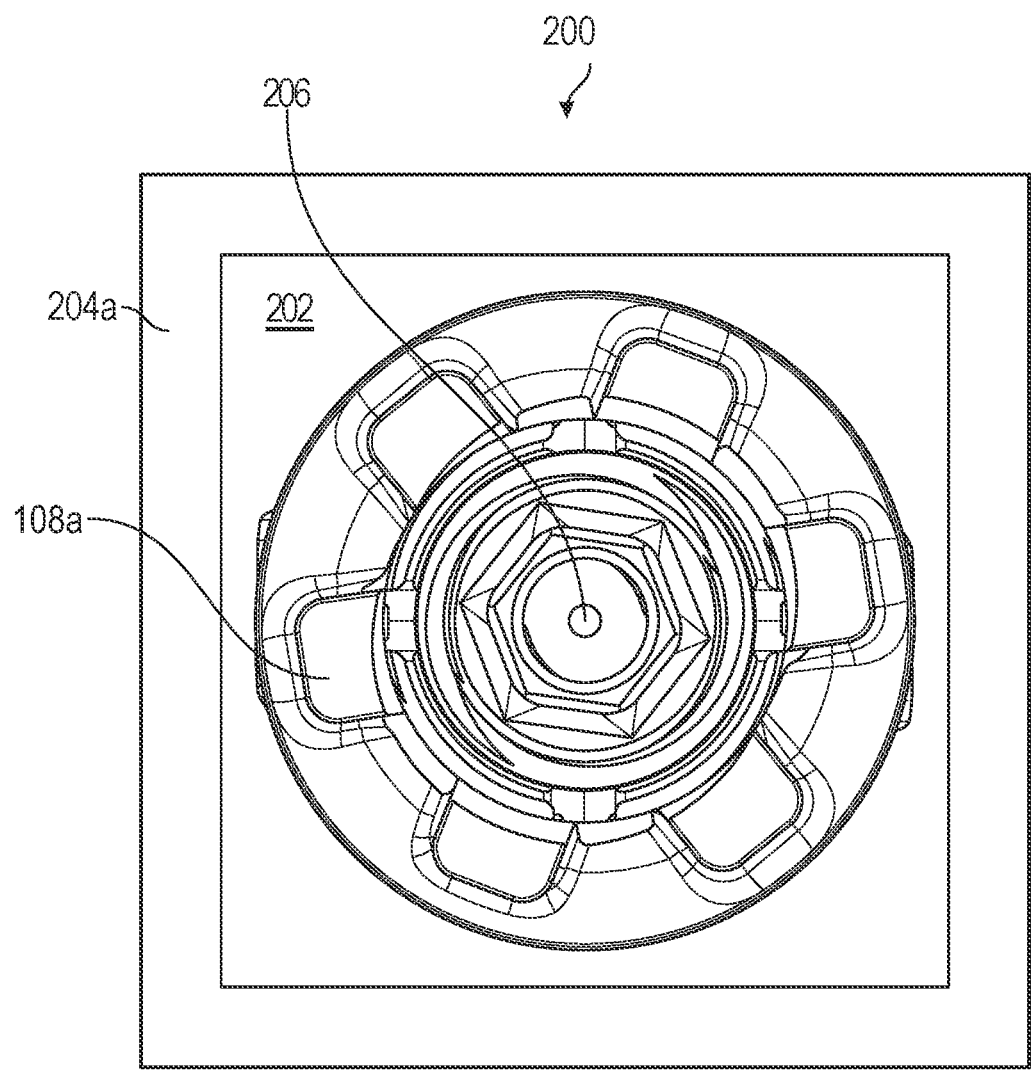

FIGS. 2A and 2B schematically depict how a lateral SI implant 108a may interlock with a posterior SI implant 200 in accordance with aspects of the present disclosure. FIG. 2A illustrates a posterior-looking view of the interlocked implants 108a, 200 in SI joint 102, and FIG. 2B illustrates a medial-looking planar view of the interlocked implants 108a, 200. As shown, posterior SI implant 200 may have a generally rectangular cross-section; however other cross-sectional shapes are within the scope of the present disclosure. For example, posterior SI implant 200 may have a trapezoidal, a triangular, an ovular, a circular, or any other cross-sectional shape, including non-uniform cross-sections. As one example, posterior SI implant 200 may have a generally rectangular cross-section with a sharp distal tip that aids in inserting posterior SI implant 200 such that the cross-section of the distal tip is distinct from the cross-section of the rectangular body.

Posterior SI implant 200 may have a window 202 extending through the implant 200, from a first face 204a to a second face 204b. When inserted, first face 204a may be adjacent to ilium 104, and second face 204b may be adjacent to sacrum 106. The window 202 may be rectangular, as shown, or any other shape (e.g., ovular, trapezoidal, circular, etc.). The window 202 may be sized such that lateral SI implant 108a can fit through window 202. As discussed further below, a distal end of lateral SI implant 108a may have deployable wings that extend from a body of lateral SI implant 108*a* when lateral SI implant 108*a* transitions from a closed configuration to an open configuration. Accordingly, in some embodiments, window 202 may be sized such that lateral SI implant 108*a* can fit through window 202 when lateral SI implant 108*a* is in the closed configuration even if lateral SI implant 108*a* cannot fit through window 202 when in the open configuration and the wings are deployed. Generally, posterior SI implant 200 may take any configuration that enables lateral SI implant 108*a* to be inserted through posterior SI implant 200 to interlock the two implants 108*a*, 200. In some embodiments, a targeting tool is provided that aids the surgeon in inserting the lateral SI implant 108*a* through window 202.

Interlocking implants 108*a*, 200 may improve the engagement of posterior SI implant 200 with ilium 104 and sacrum 106. As previously discussed, posterior SI implant 200 helps manage loads applied to SI joint 102 by interposing the implant 200 between ilium 104 and sacrum 106. By interlocking posterior SI implant 200 with lateral SI implant 108*a* and applying compression across SI joint 102, where the compressive force is generally in-line with a lateral axis 206 of posterior SI implant 200 the fixation provided by posterior SI implant 200 may be improved. As discussed previously, multiple lateral and posterior implants may be inserted across or into the SI joint 102 and, likewise, multiple sets of interlocking implants 108*a*, 200 may be inserted as part of the SI joint fusion procedure. For example, a first interlocking implant set (formed by lateral SI implant 108*a* and posterior SI implant 200) may be inserted at a first location in the SI joint 102, and a second interlocking implant set may be inserted at a second location in the SI joint 102 at a location distinct from the first location.

Exemplary lateral SI and posterior SI implants, insertion instruments, and methods for inserting the implants are discussed in detail below.

Posterior SI Implant

FIGS. 3A-3E illustrate a posterior SI implant 300 for some embodiments of the present disclosure. Posterior SI implant 300 may correspond to posterior SI implant 110 discussed above. Posterior SI implant 300 may be configured for stabilization and fusion of bones and/or joints, such as the sacroiliac (SI) joint 102, as discussed above. An implant 300 may be inserted posteriorly into the SI joint 102 and wedged between the ilium 104 and the sacrum 106. The implant 300 may be placed in or proximal to the S1 vertebra of the sacrum 106 or at any other location in the SI joint 102. The implant 300 may be externally threaded, and the threads may help anchor implant 300 to ilium 104 and sacrum 106 on either side of SI joint 102.

The implant 300 may be inserted via a minimally invasive incision. As discussed, a minimally invasive incision may comprise an incision of less than about 2 inches, in contrast to traditional open surgeries having five-to-six-inch incisions. Minimally invasive surgeries allow for muscle to be distracted as opposed to cut away as in open surgeries, which allows for quicker recoveries, reduced blood loss, and hospital stay, among other benefits.

The implant 300 may have a distal end configured to self-drill the implant 300 into bone, which may obviate the need to drill a pilot hole. A central section may extend proximally from the distal section and may have a lattice structure therein. A proximal section may extend proximally from the central section and may be configured to receive an insertion tool for inserting implant 300 into the patient. The lattice structure may delineate the central section from the proximal and distal sections. The implant 300 may be cannulated along a length thereof. The open architecture provided by the cannula and the lattice structure may promote bone ingrowth (osseointegration) when implant 300 is implanted. Improving bone ingrowth may improve bony fusion, thereby increasing the stabilization of the bone. In contrast, typical posterior SI joint implants are solid structures that cannot be packed internally with bone graft and, as such, the bone ingrowth of such implants may be less than implant 300 described herein. The implant 300 may be additively manufactured from a metal or metal alloy.

Figure 3B:
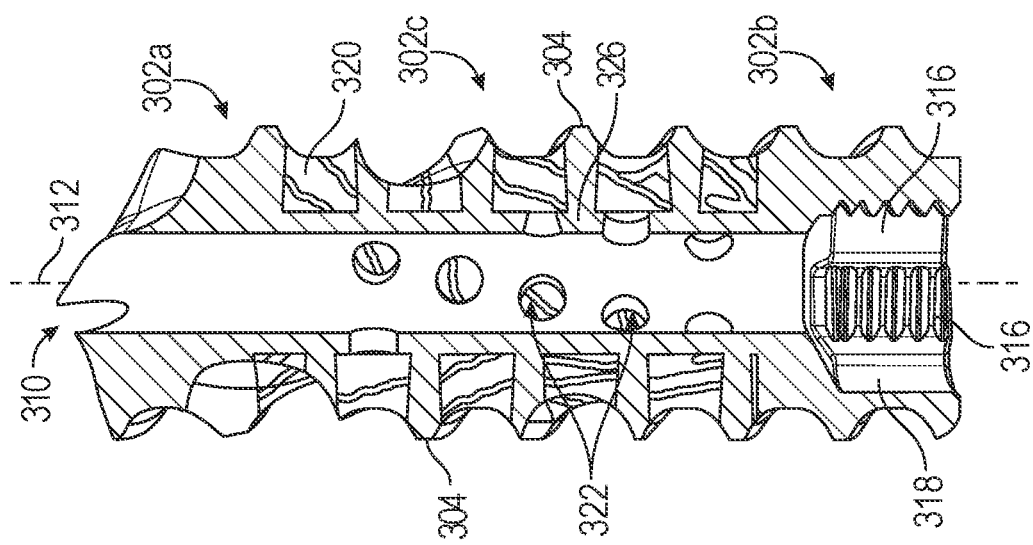
FIG. 3B illustrates a first cross-sectional view of the posterior SI implant for some embodiments.
Figure 3A:
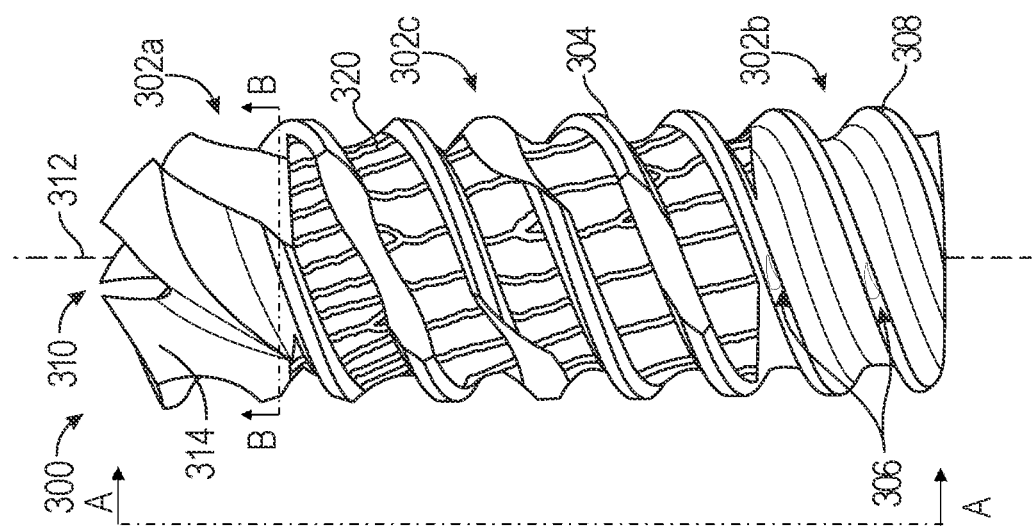
FIG. 3A illustrates a planar view of the posterior SI implant for some embodiments.

Looking at FIGS. 3A and 3B, a planar view and a cross-sectional view taken along the line A-A, respectively, are illustrated for some embodiments of the present disclosure. As shown, implant 300 may comprise a distal section 302*a*, a proximal section 302*b*, and a central section 302*c* extending between distal section 302*a* and proximal section 302*b*. Implant 300 may comprise external threads 304 along a length thereof. In some embodiments, threads 304 extend entirely along implant 300. It is contemplated that a portion of implant 300 may be unthreaded. For example, proximal section 302*b* may be unthreaded. As described above, when inserted in SI joint 102, threads 304 may engage with ilium 104 and sacrum 106 to maintain the position of implant 300 within SI joint 102. The threaded engagement may reduce movement of implant 300 when inserted into SI joint 102.

In some embodiments, the major diameter of threads 304 increases from distal section 302*a* to proximal section 302*b*. Providing a larger diameter at proximal section 302*b* may provide implant 300 with a tighter fit when inserted into the final position, which may reduce the likelihood that the implant 300 moves once inserted. In some embodiments, the major diameter of threads 304 at distal section 302*a* is about 7 mm, and the major diameter of threads 304 at proximal section 302*b* is about 10 mm. In some embodiments, the threads 304 on distal section 302*a* may taper down towards the distal end of distal section 302*a*.

Threads 304 may be single lead threads, dual lead threads, tri-lead threads, quad lead threads, or any other thread type. Threads 304 may have a major diameter of about 7 mm to about 10 mm and a minor diameter of about 5 mm to about 8 mm in some embodiments. Generally, any thread dimensions may be employed, and it will be appreciated that the thread dimensions and other dimensions of implant 300 may vary based on where in the body implant 300 is configured to be inserted. For example, an implant 300 configured for insertion into SI joint 102 may have different thread dimensions than an implant 300 configured for insertion into the foot.

Figure 3D:
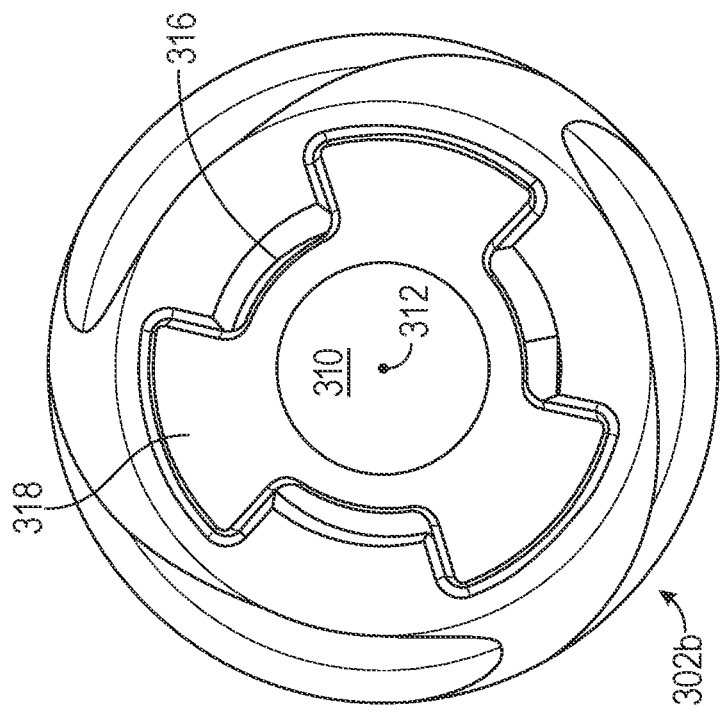
FIG. 3D illustrates a distal-looking view of the posterior SI implant for some embodiments.
Figure 3C:
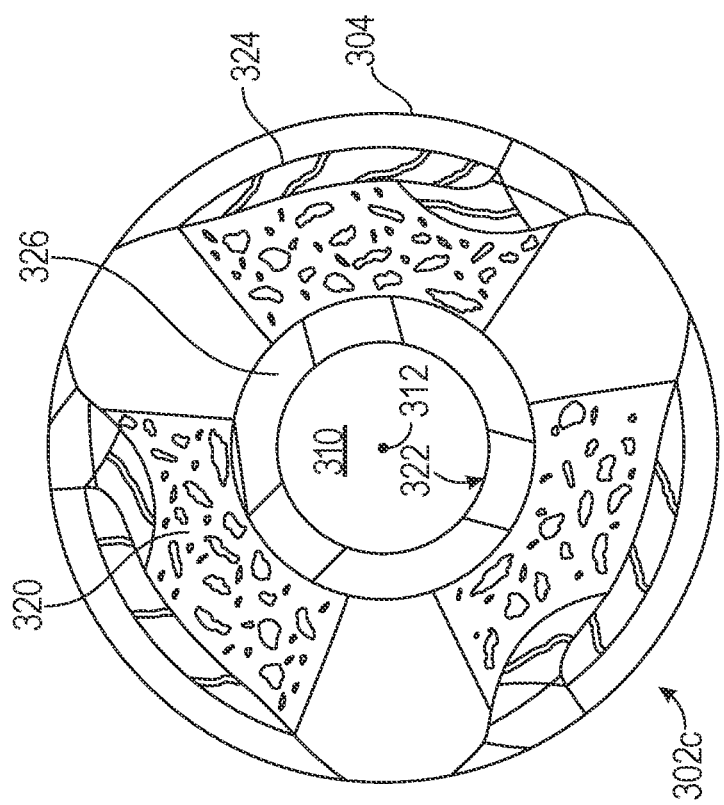
FIG. 3C illustrates a second cross-sectional view of the posterior SI implant for some embodiments.
Figure 3E:
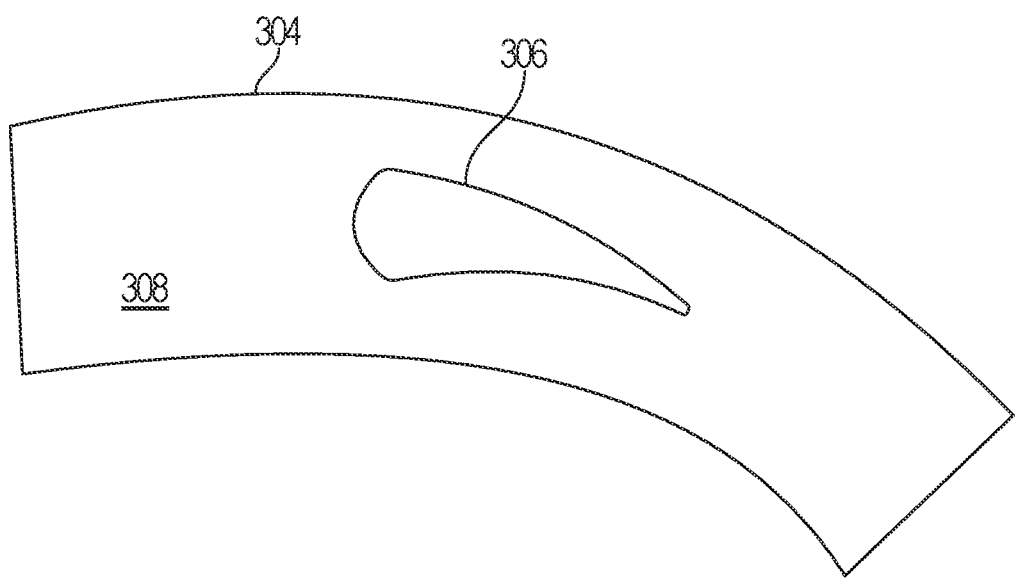
FIG. 3E illustrates a top-down view of a thread heel on a thread of the posterior SI implant for some embodiments.

In some embodiments, and as shown in FIGS. 3A and 3E, threads 304 comprise heels 306 on an outer surface 308 of threads 304. The heels 306 (also referred to as hooks or teeth) may be a gripping feature configured to maintain the position/minimize movement of implant 300 in SI joint 102. When implant 300 is inserted into SI joint 102, heels 306 may at least partially embed into ilium 104 and sacrum 106 and resist movement of implant 300. Accordingly, back out of implant 300 from SI joint 102 may be mitigated.

As shown, heels 306 may be oriented in one direction. That is, heels may have a first end with a smaller width than a second end. For example, heels 306 may have a first end formed as a pointed tip and a second end formed as a blunt tip. The first end may be distal from the second end. Providing heels 306 with such a geometry may allow for heels 306 to not interfere (e.g., not resist) the threading of implant 300 into SI joint 102 while resisting any proximal motion of implant 300 out of SI joint 102. In some embodiments, heels 306 protrude from outer surface 308. In some embodiments, heels 306 protrude a height of about 1 mm above outer surface 308. In some embodiments, the height of heels 306 decreases from the second, wider end to the first, thinner end, or vice versa. In some embodiments, heels 306 are evenly spaced on threads 304 along the length of implant 300. In some embodiments, heels 306 are spaced along threads 304 by 15 degrees, 30 degrees, 45 degrees, 90 degrees, 180 degrees, or in any other increment. In some embodiments, the spacing between heels 306 is not even. For example, it may be advantageous to have more heels 306 and/or reduced spacing between heels 306 near proximal section 302b than near distal section 302a to aid in mitigating back out of implant 300. Generally, any number, arrangement, sizing, spacing, or any combination thereof of heels 306 on threads 304 is within the scope of the present disclosure.

In some embodiments, implant 300 has a cannula 310 extending along a length thereof. The cannula 310 may extend entirely through implant 300. In some embodiments, implant 300 may be symmetrical about a longitudinal axis 312, and cannula 310 may extend along longitudinal axis 312 such that cannula 310 presents a central bore through implant 300. In some embodiments, cannula 310 is sized to receive a guidewire therethrough such that implant 300 may be inserted over the guidewire. As shown in FIG. 3B, cannula 310 may have a variable diameter. For example, proximal section 302b may have a larger diameter to accommodate an insertion instrument (discussed below). In some embodiments, cannula 310 does not extend entirely through implant 300 such that distal section 302a is closed. In some embodiments, implant 300 does not comprise a cannula 310, presenting a solid structure. In some such embodiments, proximal section 302b may be formed with a recess as shown for coupling to an insertion instrument.

As discussed previously, distal section 302a may be configured for self-drilling implant 300 into bone such that a pilot hole may not need to be drilled into the patient. In some embodiments, distal section 302a comprises one or more flutes 314 that aid in self-drilling. Additionally, threads 304 may be sharp to aid in self-drilling. For example, threads 304 may be cutting threads or box threads configured to cut through bone. Threads 304 and/or flutes 314 may also self-harvest the drilled bone, which may further promote bone ingrowth of implant 300.

Looking now at FIGS. 3B and 3D, it can be seen that proximal section 302b may be configured for coupling to the insertion instrument. In some embodiments, proximal section 302b may comprise internal threads 316 and recesses 318. In some embodiments, each recess 318 mates with a corresponding prong of the insertion instrument, and internal threads 316 couple to a threaded rod of the insertion instrument, as discussed in further detail below (see FIGS. 4A-4C). Accordingly, once coupled, the insertion instrument may be used to insert implant 300 into SI joint 102. When implant 300 is formed without a cannula 310, proximal section 302b may still comprise internal threads 316 and recesses 318, while distal section 302a and central section 302c may be solid through their center.

As shown in FIGS. 3A-3C, central section 302c may comprise a lattice structure 320 and openings 322 (also referred to as fenestrations). The portion of implant 300 that is distal from lattice structure 320 may be distal section 302a, and the portion of implant 300 that is proximal from 1022 may be proximal section 302b. Providing a lattice structure 320 may reduce the overall weight of implant 300. Furthermore, the lattice structure 320 provides for open volume in which bone graft may flow to promote bone ingrowth. In some embodiments, implant 300 may be prepacked and/or post-packed with bone graft to promote bony fusion. Openings 322 may fluidly connect cannula 310 to lattice structure 320, thereby allowing for bone graft to be packed via cannula 310 and travel into lattice structure 320. Openings 322 may follow the thread path of threads 304. By following the thread path of threads 112, bone ingrowth may be enabled across or through implant 300 from ilium 104 to sacrum 106. In some embodiments, openings 322 are arranged linearly in central section 302c. Generally, any arrangement of openings 322 within central section 302c is within the scope hereof. In some embodiments, central section 302c comprises a length of about 20% to about 80% of an overall length of implant 300. In some embodiments, central section 302c comprises a length of about 30% to about 60% of an overall length of implant 300. In some embodiments, central section 302c comprises a length of about 50% of an overall length of implant 300. In some embodiments, implant 300 comprises a length measured from proximal section 302b to distal section 302a of about 25 mm to about 35 mm.

Referring now to FIG. 3C, a cross-sectional, proximal-looking view taken along the lines B-B shown in FIG. 3A is illustrated for some embodiments. As shown, lattice structure 320 extends laterally substantially from a minor diameter 324 of threads 304 to a core region 326 of implant 300. The core region 326 may be an interior region of implant 300 through which lattice structure 320 does not extend. Core region 326 may be adjacent to cannula 310. Core region 326 may be generally solid; however, and as shown, openings 322 may extend through portions of core region 326 to fluidly connect cannula 310 to lattice structure 320. Accordingly, bone graft may be inserted into cannula 310 and flow into lattice structure 320 via openings 322. Furthermore, as seen best in FIG. 3B, the core region 326 is mechanically connected to the solid thread profile at various locations along the length of central section 302c, which improves the mechanical strength of implant 300 as compared to an implant in which lattice structure 320 was adjacent to cannula 310 (i.e., if core region 326 was not present).

As previously discussed, implant 300 may be additively manufactured. Accordingly, lattice structure 320 may be a software-generated lattice structure printed by an additive manufacturing device. In some embodiments, lattice structure 320 is a triply periodic minimal surface (TPMS) lattice. In some embodiments, lattice structure 320 is a split-P TPMS lattice, or may be any other TPMS lattice type. In some embodiments, lattice structure 320 is one of a cubic lattice, a pentagonal lattice, a hexagonal lattice, an octagonal lattice, or the like. Generally, any type of lattice structure may be used. The lattice structure 320 may be roughened, which may further promote bone ingrowth of implant 300. Further, lattice structure 320 may comprise more than one lattice type. For example, a first portion of lattice structure 320 may have a first lattice type and a second portion of lattice structure 320 may have a second lattice type. It is contemplated that the lattice structure may be selected and/or customized based on the specific anatomy of the patient.

In some embodiments, implant 300 is formed from a metal or metal alloy. In some embodiments, implant 300 is formed from a titanium or titanium alloy. In some embodiments, implant 300 comprises Ti-6AI-4V, which is an alpha-beta titanium alloy that provides a high specific strength and good corrosion resistance. It is contemplated that other alpha-beta titanium alloys may be used without departing from the scope hereof. For example, implant 300 may comprise TI-6Al-7Nb. Other metal and metal alloys may be used such as, but not limited to, cobalt chrome, stainless steel, nitinol, or tantalum. In some embodiments, implant 300 is formed from a polymer, such as PEEK. In some embodiments, implant 300 is formed from a bioresorbable material such as a ceramic, hydroxyapatite, or magnesium.

In some embodiments, implant 300 is post-processed after printing via hot isostatic pressing. Other post-processing steps, such as heat treatment, machining, surface treatments (e.g., roughening), and the like may be performed. For example, in some embodiments, at least a portion of implant 300 may undergo a roughening treatment. Providing a roughened surface may promote bone ingrowth of implant 300.

Posterior SI Implant Insertion Instrument

Figure 4A:
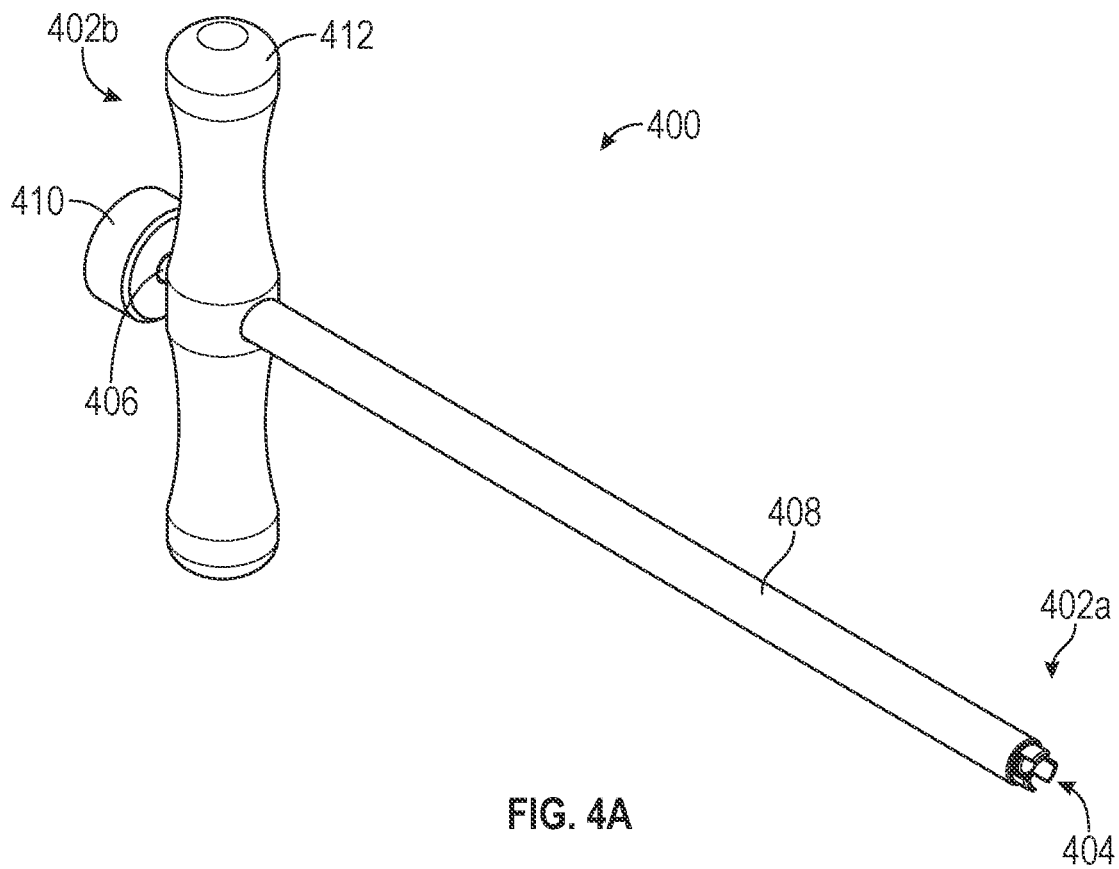
FIG. 4A illustrates a perspective view of a first insertion instrument for the posterior SI implant for some embodiments.
Figure 4B:
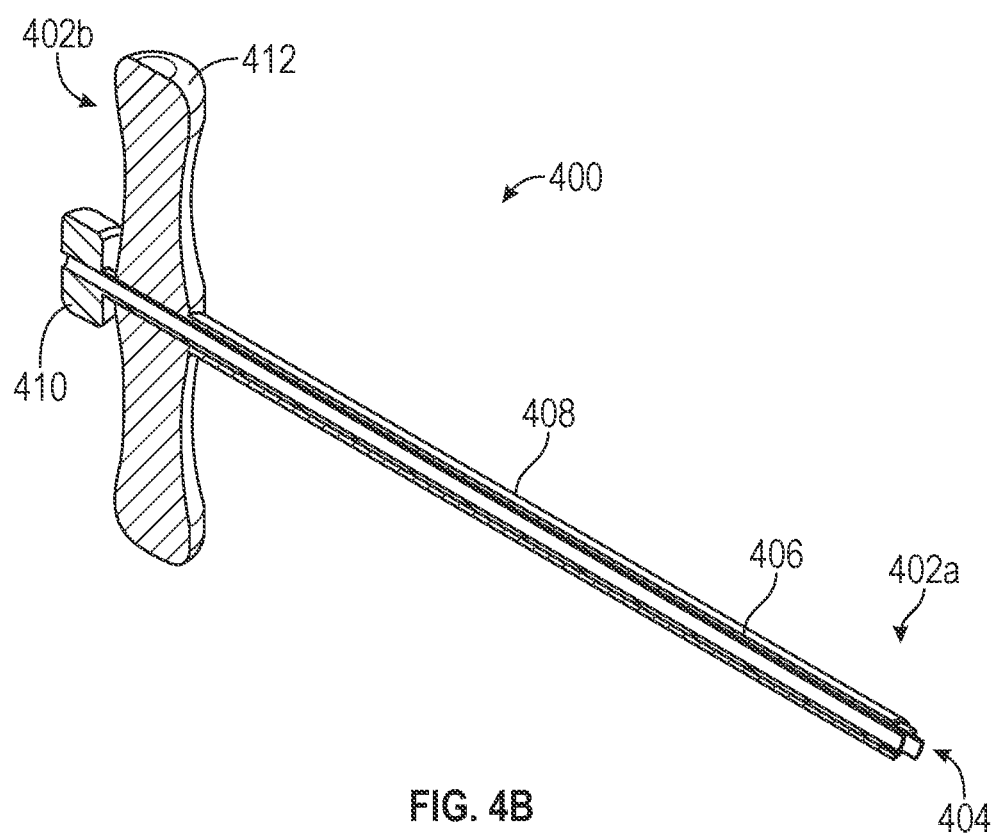
FIG. 4B illustrates a cross-sectional view of the first insertion instrument for some embodiments.
Figure 4C:
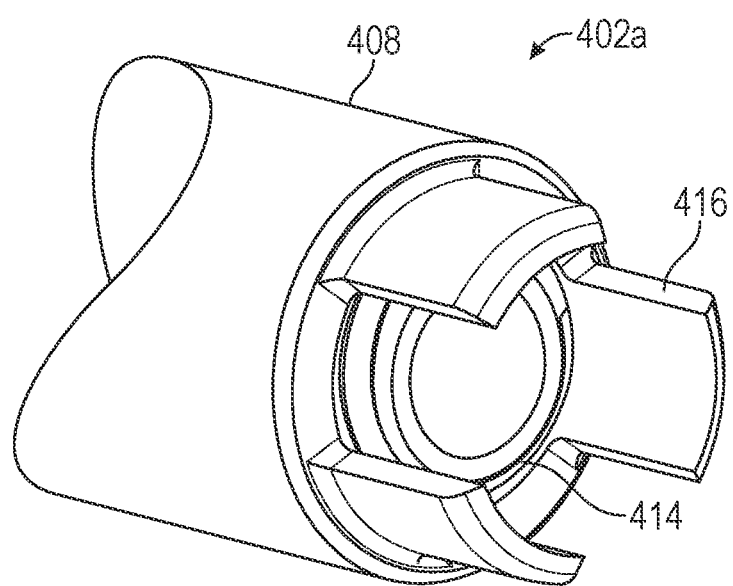
FIG. 4C illustrates a close-up view of a distal end of the first insertion instrument for some embodiments.

FIGS. 4A and 4B illustrate a perspective view and a cross-sectional view, respectively, of an insertion instrument 400 for some embodiments of the present disclosure. FIG. 4C illustrates a close-up view of a distal end of the insertion instrument 400 for some embodiments. Once the SI joint 102 is prepared for insertion of implant 300 (discussed further below), insertion instrument 400 may be used to insert implant 300 into SI joint 102.

Insertion instrument 400 may comprise a distal end 402a for coupling to implant 300 and a proximal end 402b for the operator to interface with insertion instrument 400. A bore 404 may extend lengthwise through insertion instrument 400. The bore 404 may provide a path for inserting insertion instrument 400 over a guidewire (FIG. 19) during the insertion process, as discussed further below.

Insertion instrument 400 may further comprise a rod 406 that may be received within a shaft 408. Rod 406 and shaft 408 may be concentric. An inner surface of shaft 408 may abut an outer surface of rod 406. A rod handle 410 may be coupled to a proximal end of the rod 406, and a shaft handle 412 may be coupled to the shaft 408. Shaft handle 412 may comprise a bore through which shaft 408 may extend such that a portion of shaft 408 extends proximally from shaft handle 412. In some embodiments, a proximal face of shaft handle 412 coincides with a proximal face of shaft 408. In some embodiments, rod 406 is movable longitudinally within shaft 408. The travel distance of rod 406 in the distal direction may be limited by a proximal face of shaft handle 412.

As shown in FIG. 4C, a distal end of rod 406 may comprise external threads 414 configured to threadedly engage with internal threads 316 on proximal section 302b. A distal end of shaft 408 may comprise prongs 416 configured to engage with recesses 318 in proximal section 302b. An operator may rotate rod handle 410 to mate external threads 414 with internal threads 316. Once engaged, prongs 416 may be inserted into recesses 318 to complete the coupling of insertion instrument 400 with implant 300. When implant 300 is coupled to insertion instrument 400, the operator may use shaft handle 412 to rotate insertion instrument 400, thereby driving implant 300 into SI joint 102. The flutes 314 and/or threads 304 may self-drill implant 300 into SI joint 102.

Posterior SI Implant Insertion Method

Figure 5:
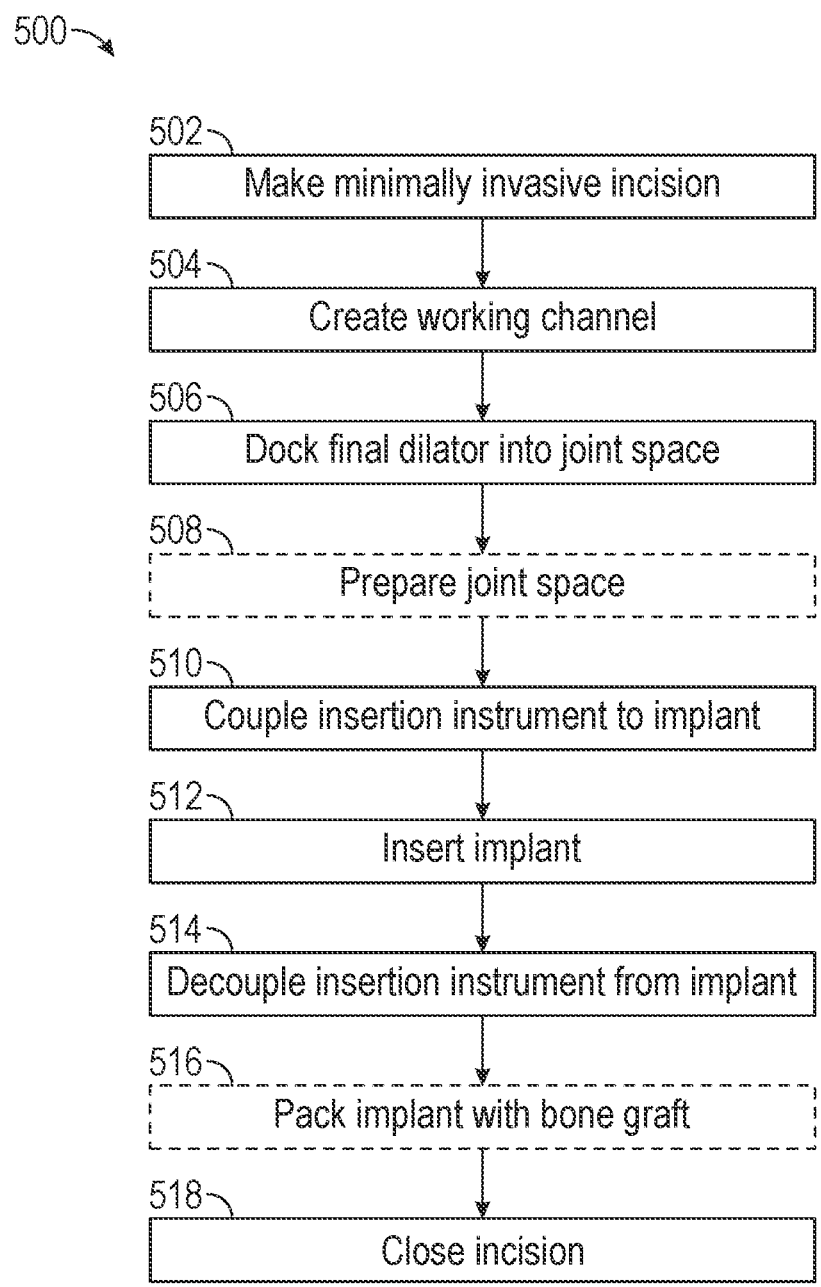
FIG. 5 illustrates an operational method for inserting the posterior SI implant for some embodiments.

FIG. 5 illustrates a method 500 for inserting implant 300 into SI joint 102 in accordance with embodiments of the present disclosure. One or more implants 300 may be inserted into the SI joint 102 to provide fusion and stabilization thereof. In some embodiments, the implant 300 is inserted at the S1 level of the spine. While method 500 is discussed with respect to a posterior approach, one of skill in the art will appreciate that method 500 may be suitably modified to insert implant 300 via other approaches, such as anteriorly. Furthermore, while method 500 is discussed with respect to inserting implant 300, method 500 may be suitably followed for implanting posterior SI implant 200.

Method 500 may begin at step 502 where a minimally invasive incision may be made on the patient. As described above, minimally invasive incisions reduce blood loss, recovery time, and hospital stay, among other benefits, as compared to open surgery. However, it is contemplated that embodiments herein may be practiced in an open surgery without departing from the scope hereof. In some embodiments, the minimally invasive incision is made to provide posterior access to SI joint 102 such that implant 300 may be inserted into SI joint 102 via a posterior approach. The patient may be placed in a prone position to provide posterior access to SI joint 102. In some embodiments, a separate incision is made for each implant 300 inserted into the SI joint 102. In some embodiments, a single incision is made for inserting implant 300 into SI joint 102. In some embodiments, one, two, three or more implants 300 may be inserted into SI joint 102.

Next, at step 504, a working channel for inserting the implant 300 may be created. In some embodiments, the working channel is created by successively inserting one or more dilators over a guidewire that is inserted into SI joint 102 to dilate soft tissues surrounding SI joint 102. In embodiments where multiple implants 300 are inserted, a parallel pin guidewire tool may be used to insert a guidewire for each implant 300. The guidewires may be inserted by tapping or any other method as will be appreciated by one of skill in the art.

Thereafter, at step 506, a final dilator may be inserted. The final dilator may comprise tangs, prongs, or other engaging features that may dock into SI joint 102 as discussed further below. The dilators may be tubes or other hollow bodies that provide a pathway for inserting implant 300 and insertion instrument 400 therein to access SI joint 102.

At optional step 508, one or more site preparation steps may be taken to prepare SI joint 102 for insertion of implant 300. In some embodiments, SI joint 102 may be roughened using a cannulated decorticator or other like tool. Another preparation step may comprise drilling a pilot hole to access SI joint 102. As described above, distal section 302a may be configured to self-drill implant 300 into SI joint 102 such that drilling a pilot hole may be unnecessary. Exemplary tools, including the guidewire and dilators, for preparing SI joint 102 for insertion of implant 300 are discussed below with respect to FIG. 19.

Next, at step 510, with SI joint 102 prepared for insertion of implant 300, implant 300 may be coupled to insertion instrument 400. As described above, external threads 414 on rod 406 may couple to internal threads 316 in proximal section 302b and prongs 416 on shaft 408 may couple to recesses 318 in proximal section 302b. Threadedly engaging external threads 414 with internal threads 316 may lock implant 300 to insertion instrument 400, while the engagement between prongs 416 and recesses 318 may allow for the rotational movement of insertion instrument 400 to rotate implant 300.

Next, at step 512, implant 300 may be inserted into SI joint 102 by rotationally driving insertion instrument 400 via shaft handle 412. As implant 300 is advanced distally, flutes 314 and/or threads 304 may work to self-drill implant 300 into SI joint 102. As discussed above, the procedure may be conducted under fluoroscopy such that the surgeon may monitor the position of implant 300 during insertion. When in the final position, threads 304 may be engaged with ilium 104 and sacrum 106, and this threaded engagement may mitigate movement of implant 300 once implanted. Furthermore, heels 306 may engage with ilium 104 and sacrum 106 to prevent backing out of implant 300 from SI joint 102.

Thereafter, at step 514, insertion instrument 400 may be decoupled from implant 300. Decoupling insertion instrument 400 from implant 300 may comprise unthreading external threads 414 from internal threads 316 and pulling insertion instrument 400 proximally to disengage prongs 416 from recesses 318.

Next, at optional step 516, implant 300 may be packed with bone graft. The bone graft may be autograft, allograft, a synthetic bone graft, or the like. Bone graft may be inserted via cannula 310 and flow through openings 322 and into lattice structure 320. In some embodiments, the bone graft is inserted into cannula 310 via the bore 404 in the insertion instrument 400. As described above, the open architecture of implant 300 may improve bone ingrowth because the bone graft may flow within the openings of implant 300. Accordingly, more bone graft may be added to implant 300 than prior implants. Implant 300 may also have bone graft packed to the exterior thereof. Lastly, at step 518, the incision may be closed to complete the insertion process.

In some embodiments, the above-described method 500 may be provided as instructions with a surgical kit. For example, the surgical kit may comprise the instrumentation required to perform the surgery, such as one or more implants 300, insertion instrument 400, and surgical tools for performing the procedure. The surgical kit may provide multiple sizes of the tools, implants 300, and inserter instruments 400, which may be selected based on the size of the patient. The surgeon may use the surgical kit to perform the fusions and follow the above-described method to carry out the operations. An exemplary surgical kit is discussed below with respect to FIG. 19.

Lateral SI Implant

Figure 6A:
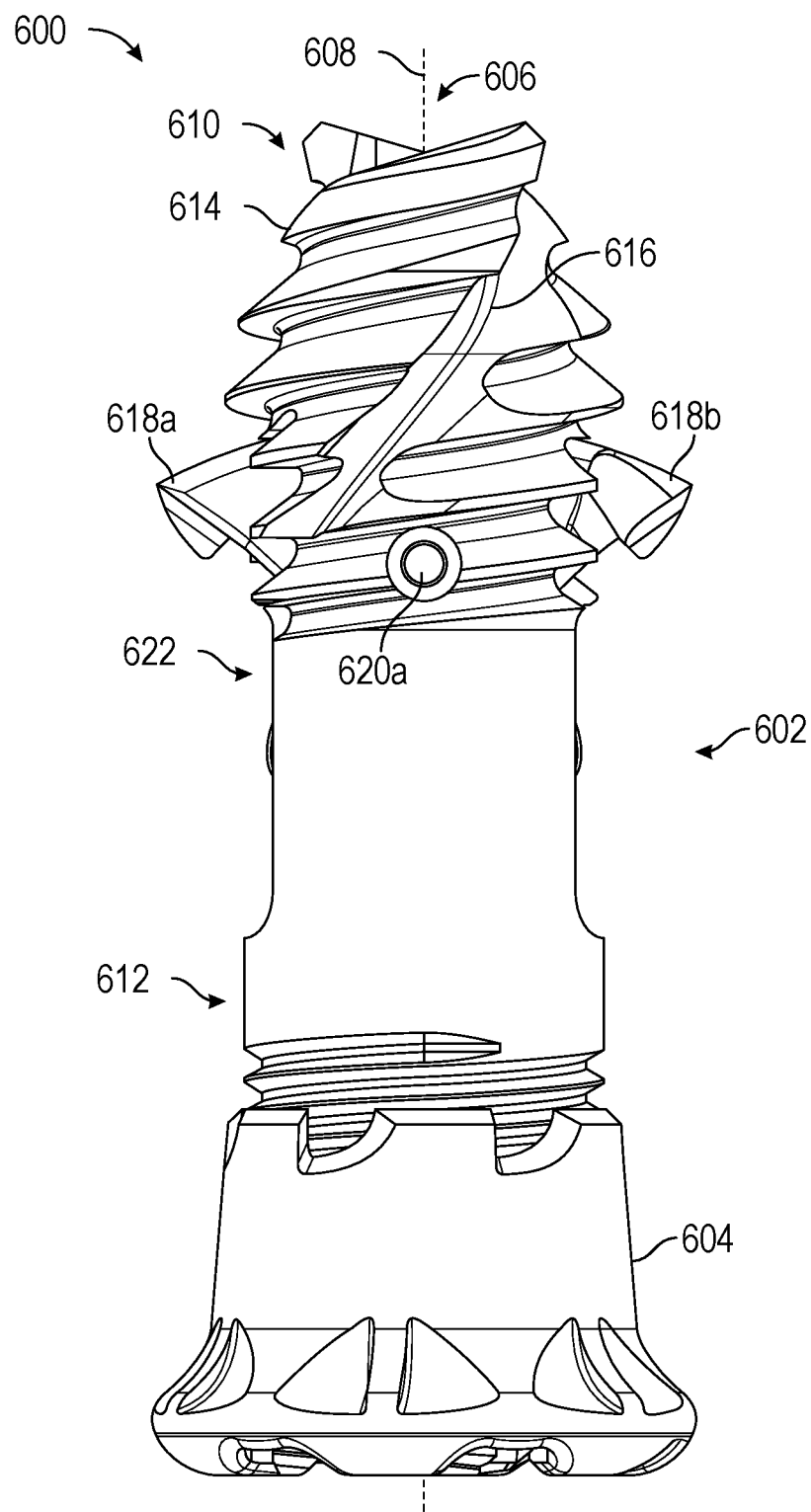
FIG. 6A illustrates a planar view of a lateral SI implant in a partially-open configuration for some embodiments of the present disclosure.

FIGS. 6A-12 illustrate a lateral SI implant 600 for some embodiments of the present disclosure. Lateral SI Implant 600 may correspond to lateral SI implant 108a discussed above. FIGS. 6A and 6B illustrate a planar view and a cross-sectional view, respectively, of implant 600 in a partially-open configuration for some embodiments of the present disclosure. Implant 600 may comprise a distal anchor formed by a pair of wings that are selectively actuatable between a closed configuration (where the wings are housed within the implant 600) and a closed configuration (where the wings extend externally from the implant 600). A compressive body on a proximal end of implant 600 may form a proximal anchor. The distal anchor and the proximal anchor may cause compression across the SI joint 102.

Implant 600 may comprise main body 602 and compressive body 604. A bore 606 may extend along a longitudinal axis 608 of implant 600. Internally, the bore 606 may be unobstructed along longitudinal axis 608 such that the implant 600 can be inserted over a guidewire for implantation into a patient. As discussed further below, various components of implant 600 may be moved to deploy the wings while maintaining an unobstructed path for a guidewire to be received through the bore 606.

Main body 602 may comprise a distal end 610 and a proximal end 612. In some embodiments, distal end 610 is configured with one or more self-drilling features to self-drill implant 600 into the patient. In some embodiments, distal end 610 comprises threads 614 and flutes 616 to self-drill implant 600 through the ilium 104 and into the sacrum 106. By self-drilling implant 600 into the patient, the need for a pilot hole to be drilled into the patient before inserting implant 600 may be alleviated. Threads 614 and flutes 616 may also self-tap implant 600 into the patient. In some embodiments, threads 614 are dual-lead threads. In some embodiments, threads 614 are single-lead threads, triple-lead threads, or quad-lead threads. Generally, threads 614 may have any number of leads. Threads 614 and flutes 616 may also be configured to reduce proximal movement of implant 600 once implanted into the patient. For example, threads 614 and flutes 616 may resist a proximal pulling force that may act on implant 600, thereby holding implant 600 in the implantation site.

In some embodiments, threads 614 may comprise a depth of about 0.5 mm to about 3.0 mm, an angle of about 45° to about 100°, and a spacing of about 1.0 mm to about 5.0 mm. In some embodiments, the angle is 50° on the leading face and 5° on the trailing face. In some embodiments, the thread has a pitch of 4 mm. In some embodiments, the spacing of peaks between threads is about 2 mm. Other thread dimensions may be used without departing from the scope hereof.

In some embodiments, distal end 610 comprises two flutes 616. In some embodiments, distal end 610 comprises fewer or greater than two flutes 616 (e.g., four). In some embodiments, the number of flutes 616 is equivalent to the number of leads for threads 614. Flutes 616 may be helical and wrap around the outer surface of distal end 610, following the path of threads 614. Along with self-drilling implant 600 into bone, flutes 616 may also help self-harvest bone during insertion and implantation of implant 600.

Figure 6B:
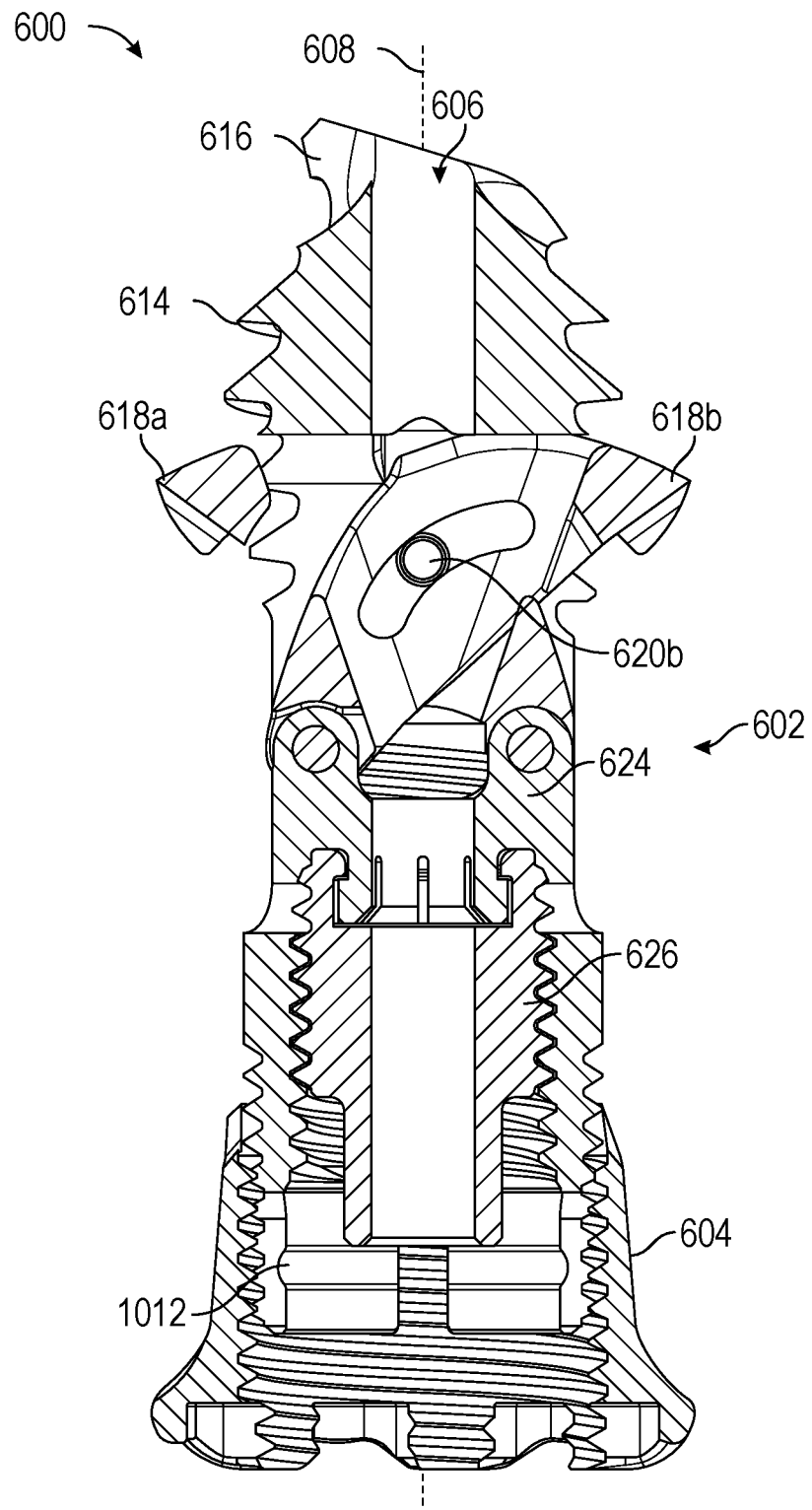
FIG. 6B illustrates a cross-sectional view of the lateral SI implant for some embodiments.

Implant 600 may comprise a distal anchor formed by a first wing 618a and a second wing 618b. Each wing 618a, 618b may be fixed within implant 600 with a separate pin 620a, 620b. The pins 620a, 620b may not extend laterally across window 622 such that bore 606 remains unobstructed along the length of implant 600. In a closed configuration of implant 600, wings 618a, 618b may be entirely within window 622, while in an open configuration, wings 618a, 618b may be deployed out of the window 622. As shown in FIG. 6B, second wing 618b has a slot that rides along the second pin 620b. When the second pin 620b sits proximal to a first or distal end of the slot, the second wing 618b may be in the open configuration, and when the second pin 620b sits in a second or proximal end of the slot, the second wing 618b may be in the closed configuration.

Each wing 618a, 618b may be coupled at an inner end to a distal plunger 624. The distal plunger 624, in turn, may be coupled to a proximal plunger 626. The distal plunger 624 and the proximal plunger 626 may be housed within main body 602. As discussed further below, the proximal plunger 626 may be configured to be driven longitudinally to cause longitudinal movement of distal plunger 624. When proximal plunger 626 moves distal plunger 624 distally, wings 618a, 618b may be deployed out of window 622. Proximal plunger 626 may threadedly engage with internal threads on main body 602 and be threaded to move longitudinally along main body 602.

Compressive body 604 may form a proximal anchor for implant 600. Compressive body 604 may have internal threading (see FIG. 11) for threadedly engaging with external threads on proximal end 612 of main body 602. Accordingly, compressive body 604 may be threaded along proximal end 612 to adjust an effective length of implant 600 and to change the amount of compression applied by compressive body 604 to the SI joint 102. Compressive body 604 is discussed further below with respect to FIG. 11.

Figure 6C:
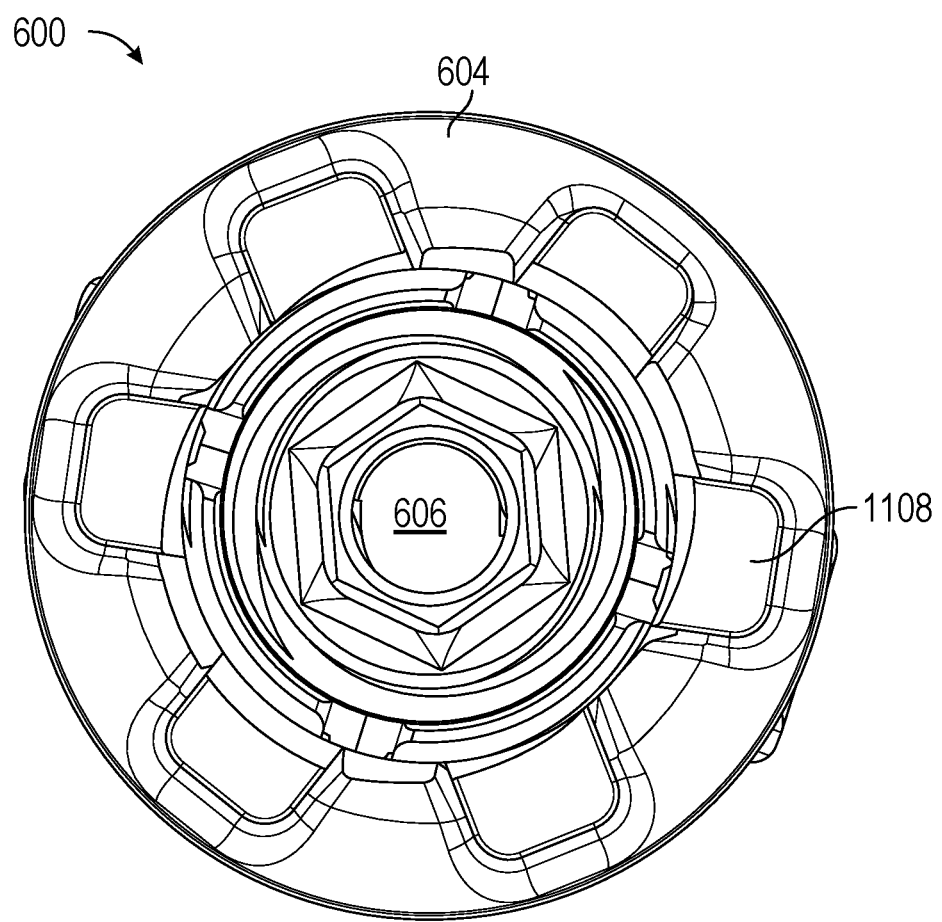
FIG. 6C illustrates a distal-looking view of the lateral SI implant for some embodiments.

Turning now to FIG. 6C, a distal-looking view of implant 600 is illustrated for some embodiments of the present disclosure. As shown, bore 606 is unobstructed centrally, along the length of implant 600 such that implant 600 can be inserted over the guidewire for insertion into the patient. Bore 606 may remain unobstructed as distal plunger 624, proximal plunger 626, and wings 618a, 618b move implant 600 between the open and closed configurations.

In some embodiments, implant 600 is provided in various lengths. Implants of different lengths may be selected based on patient anatomy. In some embodiments, a surgical kit may be provided for performing the surgery, comprising various sized implant lengths and any instrumentation (discussed further below) necessary to perform the operations. In some embodiments, compressive body 604 is configured to accommodate main bodies 602 of different lengths. In some embodiments, implant 600 is provided in a first size having a maximum length of implant 600 at a fully-extended position of about 40.4 mm, and a minimum length of about 32.4 mm. In some embodiments, implant 600 is provided in a second size where the maximum length is about 65.9 mm and the minimum length is about 57.9 mm.

Figure 7:
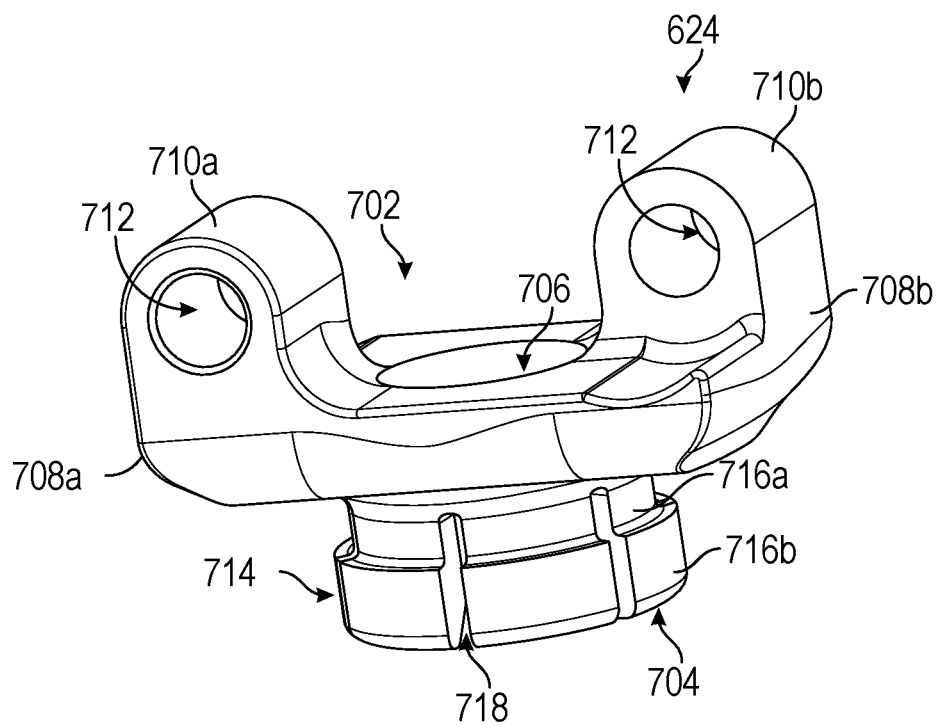
FIG. 7 illustrates an implant plunger of the lateral SI implant for some embodiments.

FIG. 7 illustrates distal plunger 624 for some embodiments of the present disclosure. Distal plunger 624 may comprise a distal end 702 and a proximal end 704. In some embodiments, distal plunger 624 defines a central bore 706 therethrough corresponding to bore 606. Distal plunger 624 may comprise a first lateral side 708a and a second lateral side 708b. A first hub 710a may protrude from distal end 702 on first lateral side 708a, and a second hub 710b may protrude from distal end 702 on second lateral side 708b. First wing 618a may be coupled to distal plunger 624 via first hub 710a, and second wing 618b may be coupled to distal plunger 624 via second hub 710b. Each hub 710a, 710b may have an opening 712 extending therethrough in which a pin may be received. The pin may extend through opening 712 and a corresponding opening on an inner end of each wing 618a, 618b to couple the wings 618a, 618b to hubs 710a, 710b (see FIG. 9).

Proximal end 704 may comprise a connecting portion 714 for coupling distal plunger 624 to proximal plunger 626. Connecting portion 714 may have a first portion 716a and a second portion 716b. First portion 716a may have a smaller diameter than second portion 716b. Proximal plunger 626 may couple with connecting portion 714, and the larger diameter second portion 716b may prevent proximal plunger 626 from decoupling from distal plunger 624 (see also FIG. 6B). In some embodiments, connecting portion 714 further comprises one or more openings 718 extending through the connecting portion 714. The openings 718 may be configured to provide flexure in the connecting portion 714 as compared to forming connecting portion 714 as a solid piece. In some embodiments, connecting portion 714 comprises two to eight openings 718 that are spaced evenly around connecting portion 714. Connecting portion 714 may comprise more, fewer, or no openings 718 in some embodiments. In some embodiments, openings 718 extend longitudinally through first portion 716a and partially into second portion 716b.

Figure 8:
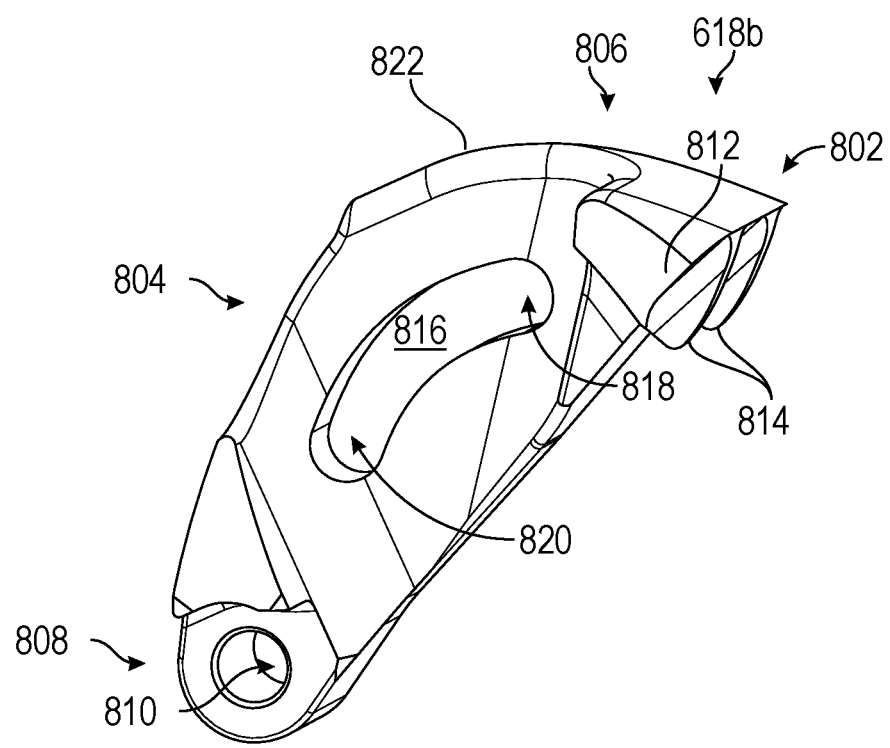
FIG. 8 illustrates a wing of the lateral SI implant for some embodiments.
Figure 9:
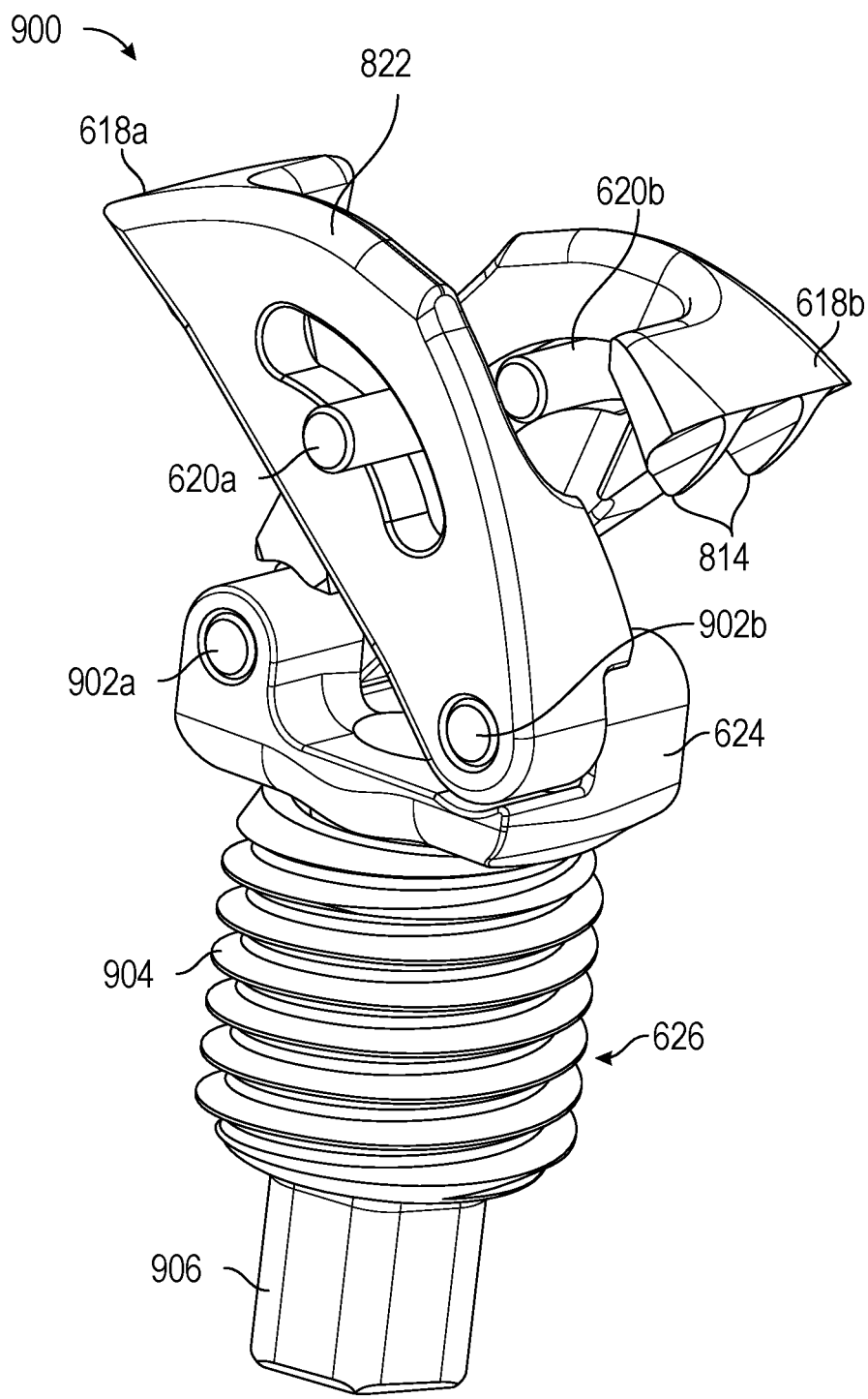
FIG. 9 illustrates a wing assembly of the lateral SI implant for some embodiments.

Turning now to FIG. 8, a perspective view of second wing 618b is illustrated for some embodiments of the present disclosure. Second wing 618b may be substantially similar to first wing 618a. Second wing 618b may comprise a wing tip 802 and a main body 804. Main body 804 may have a distal end 806 and a proximal or inner end 808. Proximal end 808 may comprise an opening 810 therethrough for receiving a pin to couple second wing 618b to distal plunger 624 as shown in FIG. 9 below. Distal end 806 may transition into wing tip 802. Wing tip 802 may be substantially rectangular with an offset portion 812 that may include a sharp edge. The sharp edge may aid in pushing through cortical bone 1206 of the sacrum 106 when wings 618a, 618b are deployed. In some embodiments, one or more fangs 814 protrude from a bottom surface of wing tip 802. The fangs 814 may help anchor implant 600 into the cortical bone 1206. Further, the fangs 814, when engaged with the cortical bone 1206, may help prevent rotation of implant 600 once implanted. In some embodiments, the bottom surface of wing tip 802 comprises one, two, or more fangs 814. In some embodiments, the bottom surface of wing tip 802 is flat with no fangs 814.

A slot 816 may extend through main body 804. Slot 816 may have a distal end 818 and a proximal end 820. Second pin 620b may be received within slot 816. Second pin 620b may be fixed within main body 602 such that, as distal plunger 624 is moved longitudinally, thereby forcing second wing 618b distally, second pin 620b may remain substantially stationary, and slot 816 may move relative to second pin 620b. Thus, in some embodiments, the travel path of wing 618a, 618b is defined by a curvature of the slot 816. In some embodiments, slot 816 defines a travel path such that wings 618a, 618b deploy path tangentially out of window 622. By path tangentially, it is meant that the wings 618a, 618b follow a path that is tangent to a curve formed by the wings 618a, 618b in the closed configuration. The path tangential deployment allows the wings 618a, 618b to displace a minimal amount of cancellous bone 1208 during the deployment process, thus minimizing trauma to the surrounding areas of the sacrum 106. In the closed configuration, second pin 620b may be seated at or proximal to the distal end 818 and, in the open configuration, second pin 620b may be seated at or proximal to the proximal end 820. Further, when in the closed configuration, the offset portion 812 of second wing 618b may be disposed above a top surface 822 of second wing 618b, and an offset portion 812 of first wing 618a may be disposed above a top surface 822 of second wing 618b. As shown in FIG. 6C, when wings 618a, 618b are in the closed configuration, bore 606 remains unobstructed for the guidewire to be received therethrough.

FIG. 9 illustrates a wing assembly 900 formed by wings 618a, 618b, distal plunger 624, and proximal plunger 626 for some embodiments of the present disclosure. The wing assembly 900 is depicted in a partially-deployed configuration with each pin 620a, 620b near a center of the slot 816, about halfway between distal end 818 and proximal end 820. As shown, first wing 618a is coupled to first hub 710a via a first pin 902a, and second wing 618b is coupled to second hub 710b via a second pin 902b. The distance between inner walls of main body 602 and the external ends of pins 902a, 902b when inserted through openings 712, 810 may be such that pins 902a, 902b are unable to slide out of openings 712, 810, thereby maintaining the connection between wings 618a, 618b and distal plunger 624.

As previously discussed, pins 620a, 620b may be received within openings on main body 602 and fixed to main body 602 such that pins 620a, 620b do not move during operations of the device. Pins 620a, 620b may extend into and/or partially through offset portion 812 on wings 618a, 618b, respectively, maintaining a clear path for the guidewire to be received within bore 606. Accordingly, when distal plunger 624 moves distally, wings 618a, 618b may move along pins 620a, 620b to deploy out of window 622. The path of wings 618a, 618b when deployed may be tangent relative to a curve formed by a curvature of top surface 822 when wings 618a, 618b are in the closed configuration.

Distal plunger 624 may be moved by longitudinal movement of proximal plunger 626. In some embodiments, proximal plunger 626 comprises a threaded portion 904 and a non-threaded portion 906. The threaded portion 904 may engage with internal threading on main body 602 (see FIG. 10) to move proximal plunger 626 longitudinally. In some embodiments, the non-threaded portion 906 has a geometry configured to couple to the insertion instrument, such that the non-threaded portion 906 may be rotationally driven to rotate and thread non-threaded portion 904 along the internal threads in main body 602. For example, non-threaded portion 906 may have a hexagonal shape for coupling to a hex driver, which may be formed in the insertion instrument (see FIGS. 15A-15B). It will be understood that proximal plunger 626 has a bore therethrough corresponding to bore 606 described above.

Figure 10:
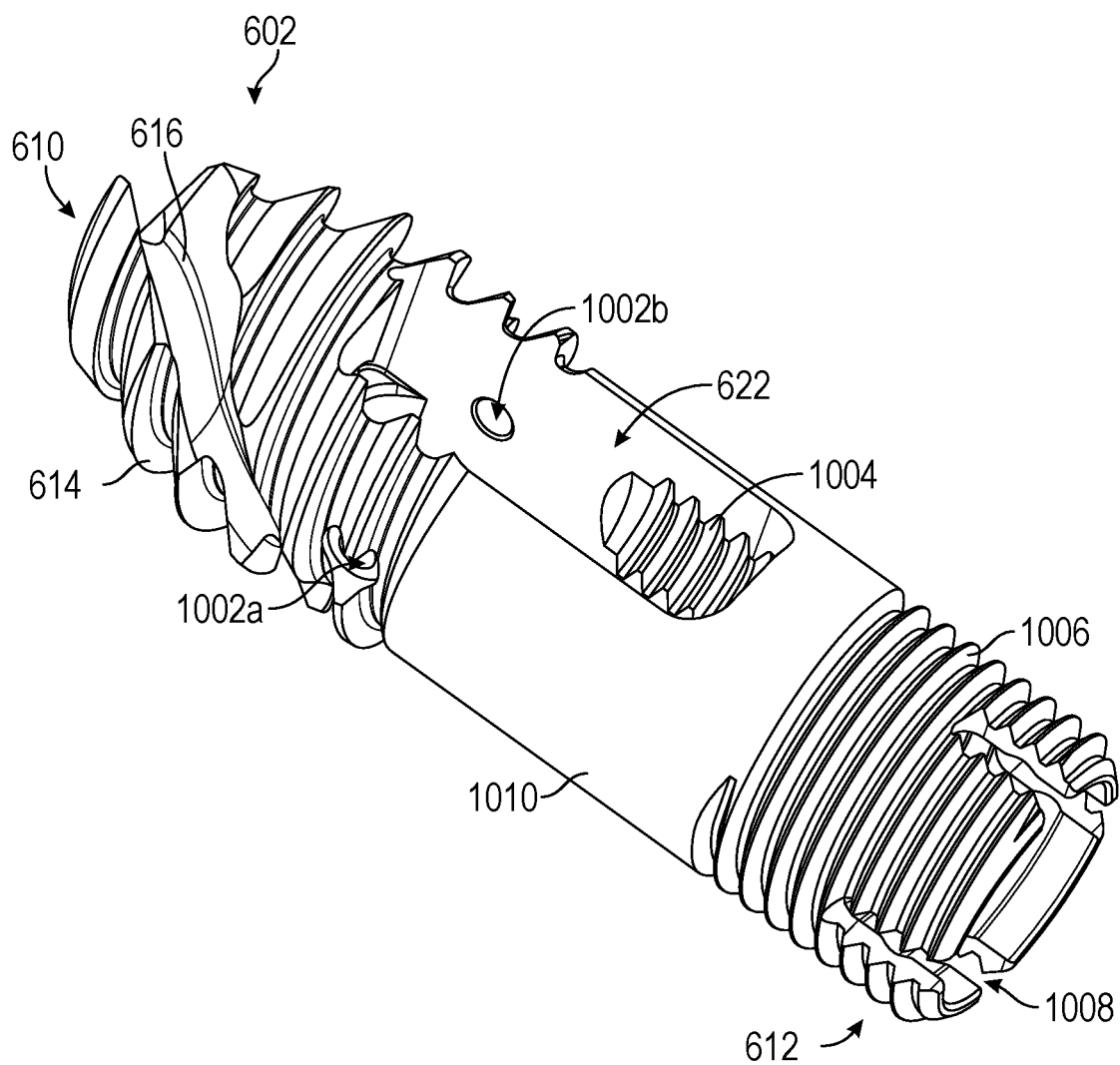
FIG. 10 illustrates a main body of the lateral SI implant for some embodiments.

FIG. 10 illustrates a perspective view of main body 602 for some embodiments of the present disclosure. Main body 602 may comprise distal end 610 and proximal end 612. Distal end 610 may comprise threads 614 and flutes 616 for self-drilling implant 600 into bone. Threads 614 and flutes 616 may extend proximally from a distal tip of distal end 610 lengthwise about a third of the overall length of main body 602. In some embodiments, threads 614 and/or flutes 616 extend lengthwise about 20% to about 50% an overall length of main body 602.

Main body 602 may also comprise a first opening 1002a and a second opening 1002b. First opening 1002a may receive first pin 620a that is received within slot 816 on first wing 618a, and second opening 1002b may receive second pin 620b that is received within slot 816 on second wing 618b. The use of two, separate pins instead of a single pin extending across window 622 may allow for bore 606 to remain unobstructed along longitudinal axis 608 such that implant 600 may be inserted over a guidewire and into the target space within a patient.

An inner surface of main body 602 may comprise internal threads 1004. Internal threads 1004 may be configured to mate with non-threaded portion 904 on proximal plunger 626. Accordingly, proximal plunger 626 may be rotationally driven and move longitudinally due to the threaded engagement of the non-threaded portion 904 with internal threads 1004. Longitudinal distal movement of proximal plunger 626 may cause deployment of wings 618a, 618b, and longitudinal proximal movement of proximal plunger 626 may cause retraction of wings 618a, 618b.

Proximal end 612 may comprise external threads 1006. External threads 1006 may be configured to mate with internal threads on compressive body 604 (see FIG. 11). Accordingly, compressive body 604 may be threaded along external threads 1006 to apply compression to the SI joint 102 (via distal movement of compressive body 604) or reduce compression to the SI joint 102 (via proximal movement of compressive body 604). Proximal end 612 may also comprise openings 1008. In some embodiments, proximal end 612 comprises four openings 1008. In some embodiments, the openings 1008 are configured to mate with a corresponding feature on a distal tip of the insertion instrument (see FIG. 16C) Openings 1008 may also allow bone graft to flow around implant 600 after placement of implant 600 to promote bony fusion.

In some embodiments, main body 602 comprises a central section 1010 extending between the threads 614 on distal end 610 and the external threads 1006 on proximal end 612. Central section 1010 may aid in retracting implant 600 to anchor wings 618a, 618b to the sacrum 106. In some embodiments, central section 1010 is substantially smooth. In some embodiments, central section 1010 is a non-threaded section of main body 602 and may have a rough outer surface to promote bony fusion. It is contemplated that one or more openings may extend through central section 1010 to aid in self-harvesting bone.

Figure 11:
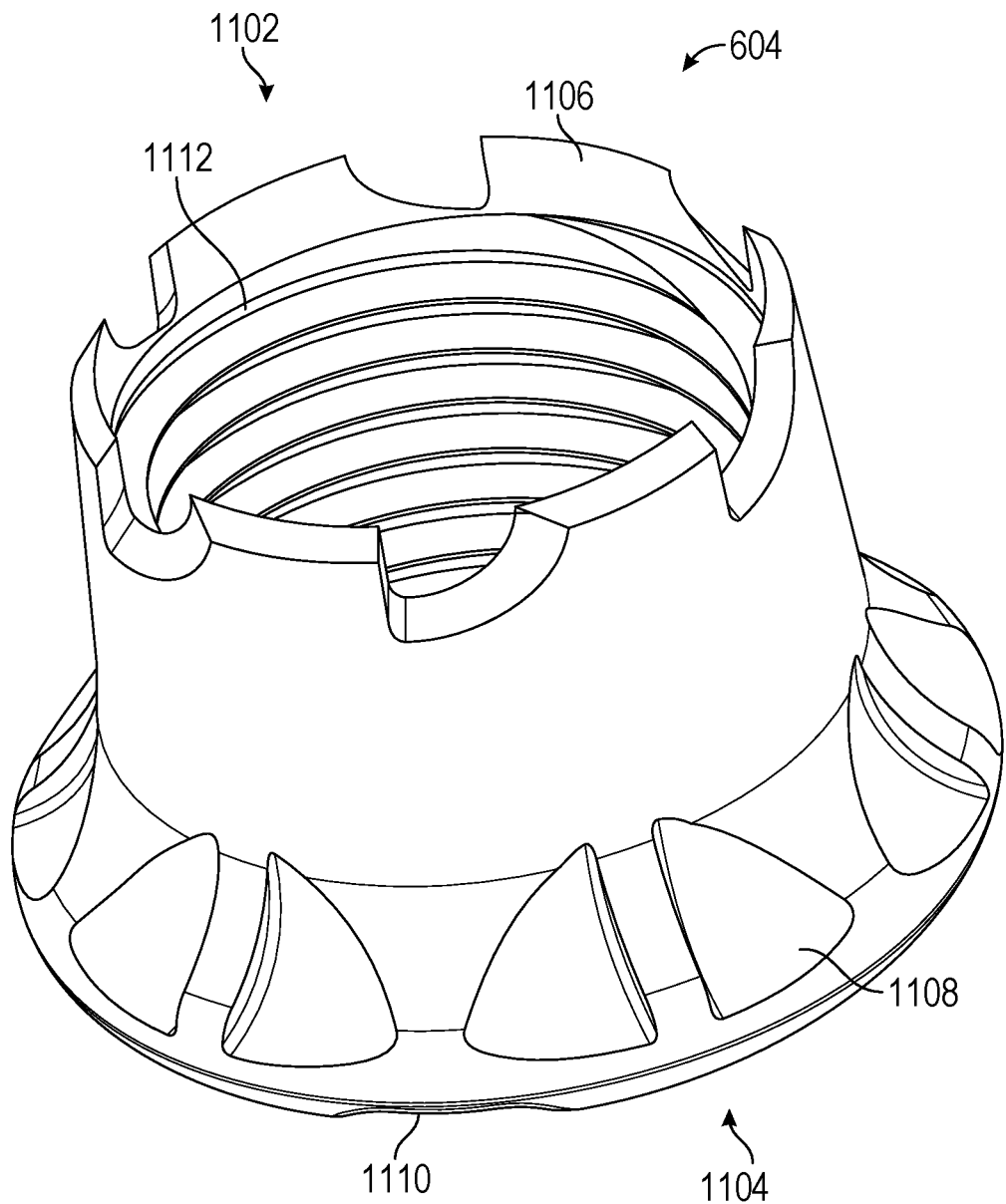
FIG. 11 illustrates a compressive body of the lateral SI implant for some embodiments.

FIG. 11 illustrates a perspective view of compressive body 604 for some embodiments. Compressive body 604 may comprise a distal end 1102 and a proximal end 1104. Distal end 1102 may be formed with teeth 1106 that may extend circumferentially around distal end 1102. In some embodiments, the teeth 1106 are sharp such that teeth 1106 help burrow compressive body 604 into the ilium.

Proximal end 1104 may comprise one or more recesses 1108 extending circumferentially around proximal end 1104. In some embodiments, the one or more recesses 1108 may be substantially triangular shaped, although embodiments are not limited to a triangle shape. In some embodiments, the recesses 1108 are configured to prevent implant 600 from bottoming out. That is, recesses 1108 help keep compressive body 604 flush against the ilium 104. Recesses 1108 may also act as a counter rotating feature for implant 600. As discussed above, the distal anchor (i.e., wings 618a, 618b) may also have fangs 814 that act as an anti-rotational feature. Thus, rotation of implant 600, when inserted, may be minimized by both wings 618a, 618b and compressive body 604.

As seen best in FIG. 6C, a bottom surface of compressive body 604 may comprise an annular array of receiving portions 1110. The receiving portions 1110 may be configured to cooperatively engage with a driver on the insertion instrument (see FIGS. 17A and 17B). Accordingly, the driver may rotationally drive compressive body 604. Internal threads 1112 on compressive body 604 may thread along external threads 1006 to move compressive body 604 longitudinally.

Figure 12:
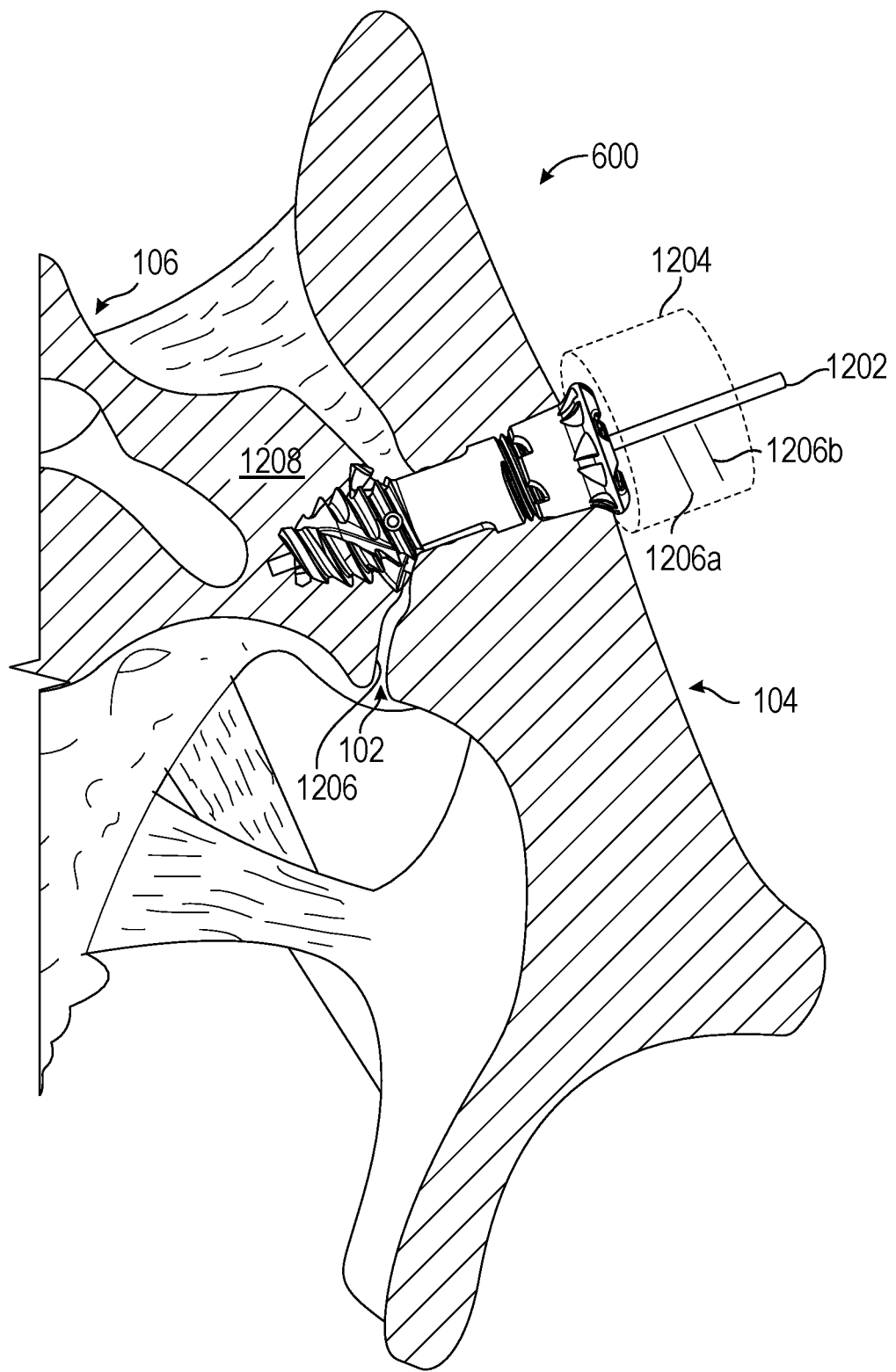
FIG. 12 illustrates the lateral SI implant inserted across the SI joint for some embodiments.

FIG. 12 illustrates implant 600 inserted into a patient for some embodiments of the present disclosure. As discussed above FIGS. 1A-2B, implant 600 may be inserted across the SI joint 102 to cause compression across the SI joint 102. Once a minimally invasive incision has been made, implant 600 may be inserted as follows. A guidewire 1202 may be inserted through the incision and the ilium 104 and into the sacrum 106. In some embodiments, the guidewire 1202 is configured to be visible under fluoroscopy to allow the surgeon to view the guidewire 1202 in the patient's body. Next, one or more sleeves 1204 may be inserted over the guidewire 1202 to dilate and/or distract surrounding tissue. Each successive sleeve 1204 may be larger than a previous sleeve. As shown in FIG. 12, once a final, largest sleeve 1204 has been inserted, the smaller sleeves may be removed, leaving the guidewire 1202 and a single sleeve 1204 in place. The sleeves 1204 may be advanced against an outer surface of the ilium 104.

When the last sleeve 1204 is in place, implant 600 may be inserted over the guidewire 1202. By "over the guidewire" it is meant that the guidewire 1202 is received within bore 606. Bore 606 may be unobstructed such that the guidewire 1202 can be received therein without obstructing the movement of the other components that are moved to deploy the wings. When two or more implants 600 are inserted across the SI joint 102, guidewires 1202 may be inserted using a parallel pin guidewire tool as is known to those of skill in the art.

Once the implant 600 is inserted over the guidewire, the implant 600 may be self-drilled into the sacrum 106. Distal end 610 may comprise threads 614 and flutes 616 that are configured for self-drilling into bone. Accordingly, the operator, using the insertion instrument, may rotationally drive implant 600 to self-drill the implant 600 into the sacrum 106.

When the implant 600 is in the target space, the wings 618a, 618b may be deployed to transition the implant 600 from the open configuration to the open configuration. Wings 618a, 618b may be deployed by longitudinal, distal movement of distal plunger 624. This longitudinal, distal movement may be accomplished using the insertion instrument, which may be configured to drive non-threaded portion 906 using a hex driver, for example. When non-threaded portion 906 is rotationally driven in a first direction, threaded portion 904 may thread along internal threads 1004 on main body 602. Accordingly, longitudinal distal movement of distal plunger 624 may be achieved, causing slots 816 on wings 618a, 618b to move along pins 620a, 620b, thereby deploying the wings 618a, 618b. Likewise, rotating the non-threaded portion 906 in a second direction that is opposite the first direction may cause longitudinal, proximal movement of distal plunger 624, thereby retracting wings 618a, 618b within window 622. In some embodiments, once wings 618a, 618b are deployed, implant 600 is pulled proximally towards the operator to engage fangs 814 with the cortical bone 1206 of the sacrum 106. Fangs 814 may provide a counter-rotational measure to prevent rotation of implant 600 when implanted.

Lastly, with wings 618a, 618b deployed, the insertion instrument may be used to thread compressive body 604 along main body 602 to provide additional compression across SI joint 102. Threading compressive body 604 distally along main body 602 may add compression to the SI joint 102, while threading compressive body 604 proximally along main body 602 may reduce compression on the SI joint 102. In some embodiments, the insertion instrument has engaging features configured to couple with internal threads 1112 on main body 602. Accordingly, the engaging features on the insertion instrument may engage with receiving portions 1110 such that the insertion instrument can rotationally drive main body 602 along the outer threads 1006 on the proximal end 612 of main body 602.

As previously discussed, implant 600 may be provided in various lengths. Accordingly, a surgeon may select an appropriate length of implant 600 based on patient anatomy when performing the SI joint fusion operation. In some embodiments, the length of implant 600 needed can be determined using the guidewire 1202. In some embodiments, the guidewire 1202 comprises one or more marking holes that indicate a length of the guidewire 1202 at the location of each of the marking holes. Thus, the surgeon can view the guidewire 1202 within the patient (i.e., under fluoroscopy) to determine the length that guidewire 1202 is inserted into the patient. The length of implant 600 may then be selected accordingly. In some embodiments, the implant size can be determined based on a distance between sleeve 1204 that is docked against an outer surface of ilium 104 and the marking hole on the guidewire 1202.

Lateral SI Implant Insertion Instrument

Figure 13A:
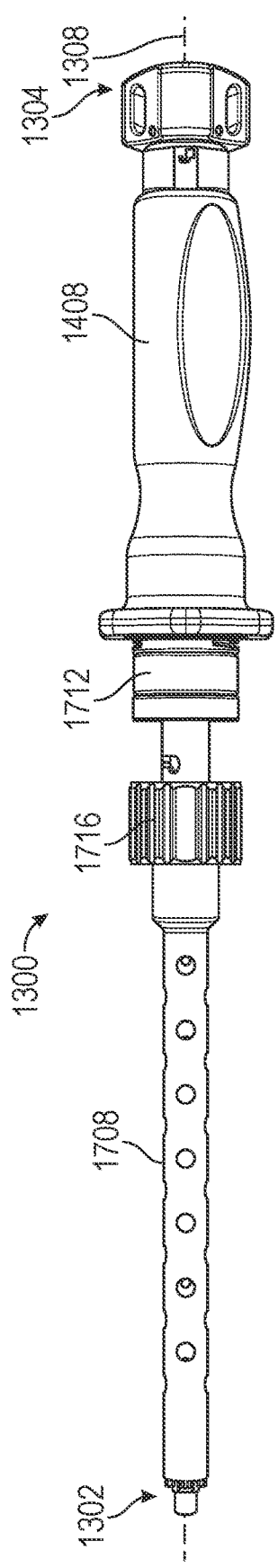
FIGS. 13A-13D illustrate a second insertion instrument for the lateral SI implant for some embodiments.
Figure 13B:
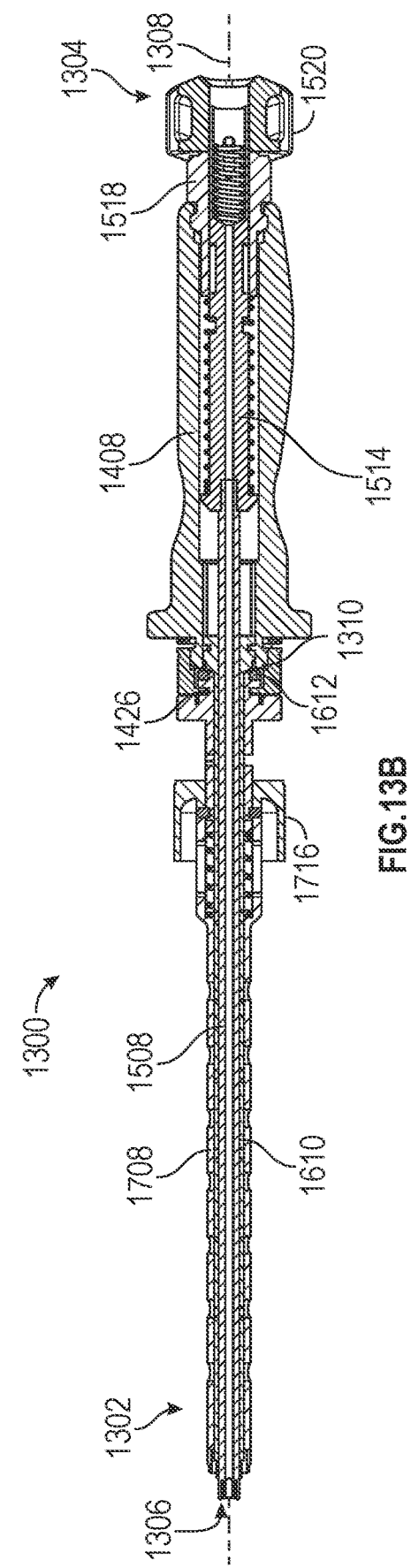
Figure 13C:
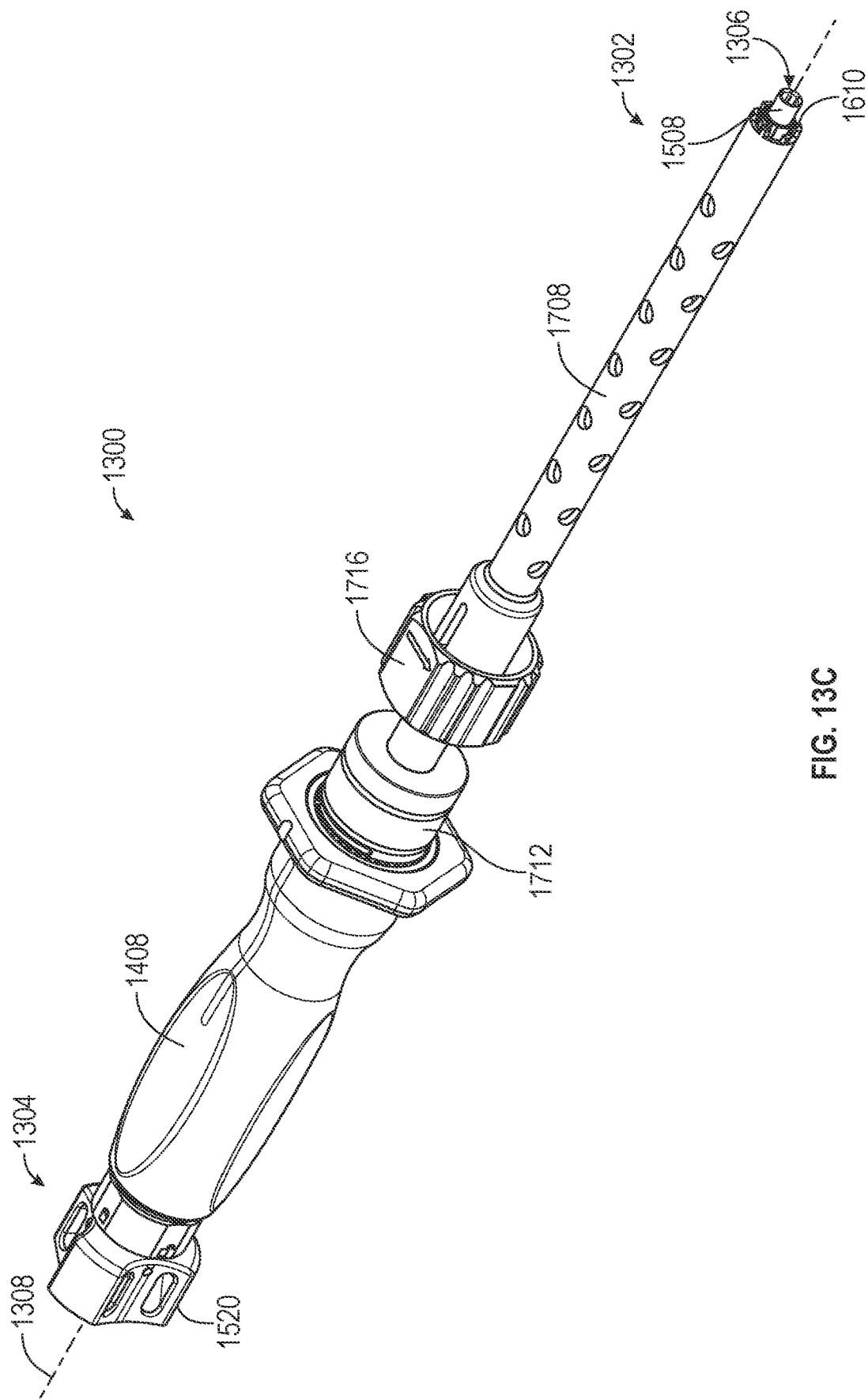

FIGS. 13A, 13B, and 13C illustrate a planar view, a cross-sectional view, and a perspective view, respectively, of an insertion instrument 1300 for some embodiments of the present disclosure. Insertion instrument 1300 may be configured to: (1) insert the implant 600 across the SI joint 102 and into the sacrum 106; (2) deploy the wings 618a, 618b; and (3) adjust the position of compressive body 604 to apply the desired compression across SI joint 102.

Insertion instrument 1300 may comprise a distal end 1302, a proximal end 1304, and a bore 1306 extending entirely along a longitudinal axis 1308 of insertion instrument 1300. When insertion instrument 1300 is coupled to implant 600, longitudinal axis 1308 may be coaxial with longitudinal axis 608 such that implant 600 and insertion instrument 1300 may be inserted over a guidewire for inserting implant 600 into the patient. Additionally, both bores 606, 1306 may be unobstructed along axes 608, 1308 to enable insertion over the guidewire. Furthermore, bores 606, 1306 may enable bone graft to be added to implant 600 through bores 606, 1306.

Figure 13D:
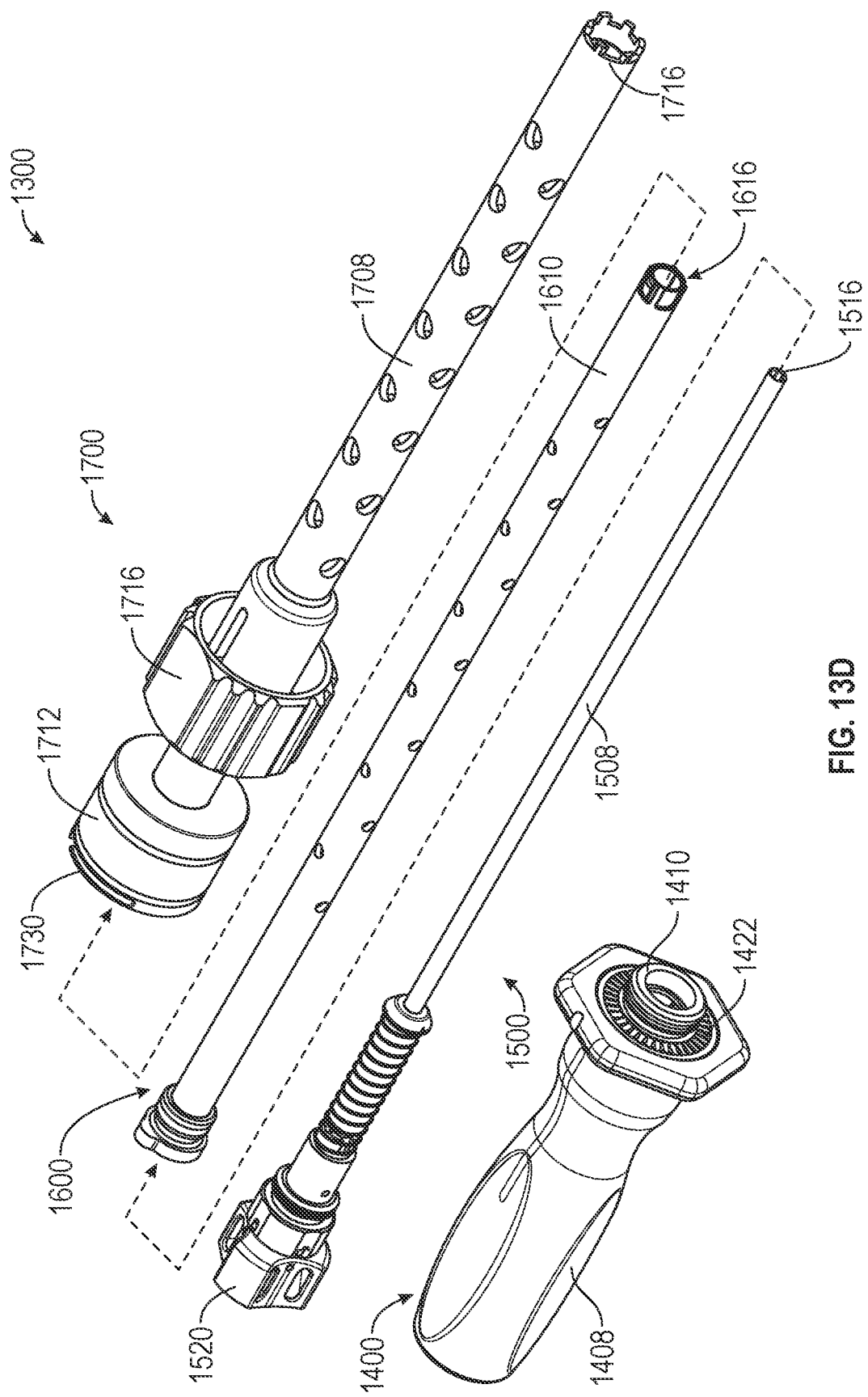

As shown in FIG. 13D, insertion instrument 1300 comprises four subassemblies: (1) a handle subassembly 1400, (2) a wing driver subassembly 1500, (3) an implant driver subassembly 1600, and (4) a compressive body driver subassembly 1700. Wing driver subassembly 1500 may be at least partially received within implant driver subassembly 1600, and implant driver subassembly 1600 may be at least partially received within compressive body driver subassembly 1700. Wing driver subassembly 1500 may be configured to deploy wings 618a, 618b and may be coupled to proximal plunger 626 on implant 600. Implant driver subassembly 1600 may be configured to rotate implant 600 for self-drilling implant 600 through ilium 104, SI joint 102, and into sacrum 106. Implant driver subassembly 1600 may couple to proximal end 612 of implant 600. Compressive body driver subassembly 1700 may be configured to move compressive body 604 longitudinally along main body 602 and, accordingly, may be coupled to compressive body 604.

Operation of insertion instrument 1300 to insert implant 600 across SI joint 102 may proceed as follows. Once insertion instrument 1300 is coupled to implant 600, implant driver subassembly 1600 may be rotated and advanced distally to rotate and self-drill implant 600 through ilium 104, across SI joint 102, and into sacrum 106. Handle subassembly 1400 may be coupled to implant driver subassembly 1600 such that rotation of handle subassembly 1400 rotates implant driver subassembly 1600. Next, wing driver subassembly 1500 may be operated to rotate and advance distally proximal plunger 626, thereby deploying wings 618a, 618b into cancellous bone 1208 of sacrum 106. Lastly, compressive body driver subassembly 1700 may be operated and rotationally driven to thread compressive body 604 to the desired location along proximal end 612. Wing driver subassembly 1500, implant driver subassembly 1600, and compressive body driver subassembly 1700, may be simultaneously coupled to implant 600 and successively actuated for insertion of implant 600, or each subassembly 1500, 1600, 1700 may be coupled to the respective component on implant 600 for actuation thereof and then decoupled before coupling the next assembly for performing the respective function.

Figure 14A:
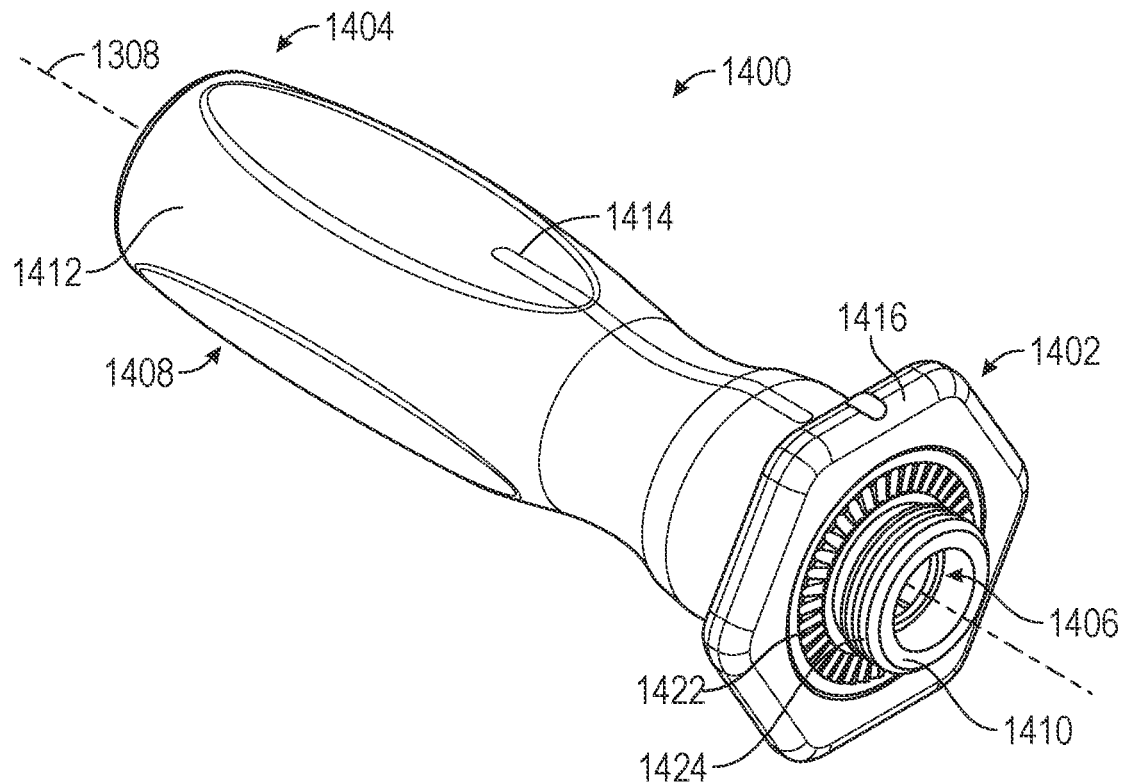
FIGS. 14A-14B illustrate a handle subassembly of the second insertion instrument for some embodiments.
Figure 14B:
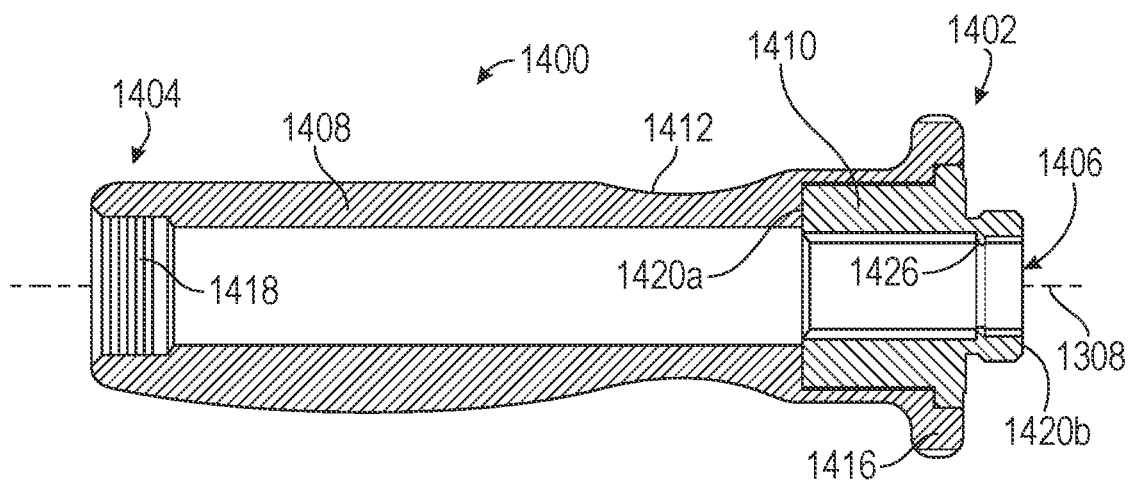

Turning now to FIGS. 14A and 14B a perspective view and a cross-sectional view, respectively, of handle subassembly 1400 are illustrated for some embodiments. Handle subassembly 1400 may comprise a distal end 1402 and a proximal end 1404. A bore 1406 may extend through handle subassembly 1400 along longitudinal axis 1308.

Handle subassembly 1400 may comprise a handle 1408 and a connecting member 1410. Handle 1408 may include a contoured outer surface 1412 for enhancing the grip of the user. Contoured outer surface 1412 may have a profile similar to a screwdriver or other rotational hand-operated tool, for example. Outer surface 1412 may also include a wing reference 1414 that provides a visual indicator to the surgeon of the position of a wing 618a, 618b. Handle 1408 may be symmetrical about longitudinal axis 1308, and a corresponding second wing reference (not shown) may be included on handle 1408, spaced 180 degrees apart from the first wing reference 1414 to indicate the position of the other wing 618a, 618b. Handle 1408 may be rotated to cause a corresponding rotation in implant 600 such that wing references 1414 remain in-line with wings 618a, 618b. Thus, the surgeon is able to ascertain the position of wings 618a, 618b using wing reference 1414. In some embodiments, handle 1408 comprises a hex-shaped distal end 1416. Handle 1408 may also comprise internal threads 1418 that threadedly engage with threads 1533 on wing driver subassembly 1500 as shown in FIG. 13B. Thus, rotation of wing driver subassembly 1500 via handle 1408 may result in rotation of implant driver subassembly 1600.

Connecting member 1410 may couple handle subassembly 1400 to both implant driver subassembly 1600 and compressive body driver subassembly 1700. Connecting member 1410 may be coupled to handle 1408 at distal end 1402. As shown, connecting member 1410 has a proximal end 1420a received within handle 1408 and a distal end 1420b extending out of handle 1408. Connecting member 1410 may be coupled to handle 1408 via welding, a friction fit, a fastener, or via any other connection. Distal end 1420b may also comprise an array of ratchet teeth 1422 for locking handle subassembly 1400 with compressive body driver subassembly 1700 as discussed further below with respect to FIGS. 17A-17B. Distal end 1420b may include external threads 1424 for coupling to compressive body driver subassembly 1700 (see FIG. 13B). The connection between connecting member 1410 and compressive body driver subassembly 1700 may be configured such that compressive body driver subassembly 1700 can rotate freely from handle subassembly 1400, as discussed further below with respect to FIGS. 17A-17B. A collar 1608 and shaft 1610 of implant driver subassembly 1600 (see FIGS. 13B and 16A-16B) may also be received within connecting member 1410 to couple implant driver subassembly 1600 to handle subassembly 1400. The subassemblies 1400, 1600 may be coupled such that rotation of handle 1408 causes a corresponding rotation in implant driver subassembly 1600, which may cause rotation of implant 600 for self-drilling implant 600 into the patient.

Figure 15A:
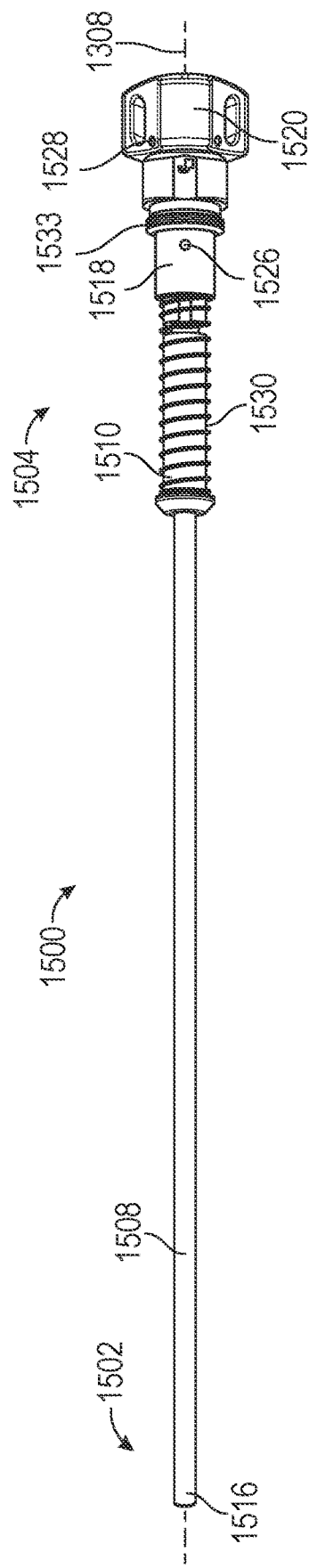
FIGS. 15A-15C illustrate a wing deployment subassembly of the second insertion instrument for some embodiments.
Figure 15B:
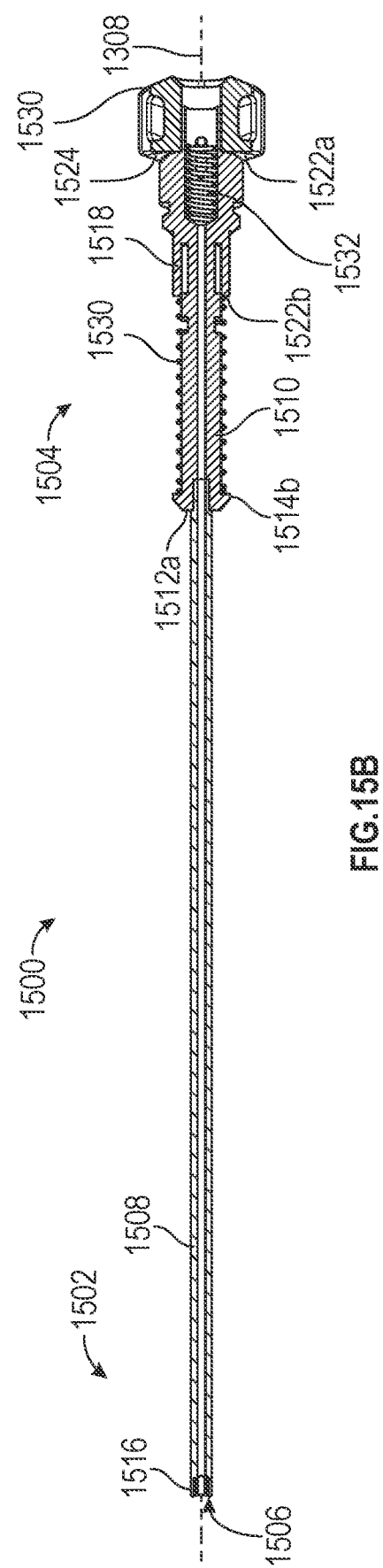
Figure 15C:
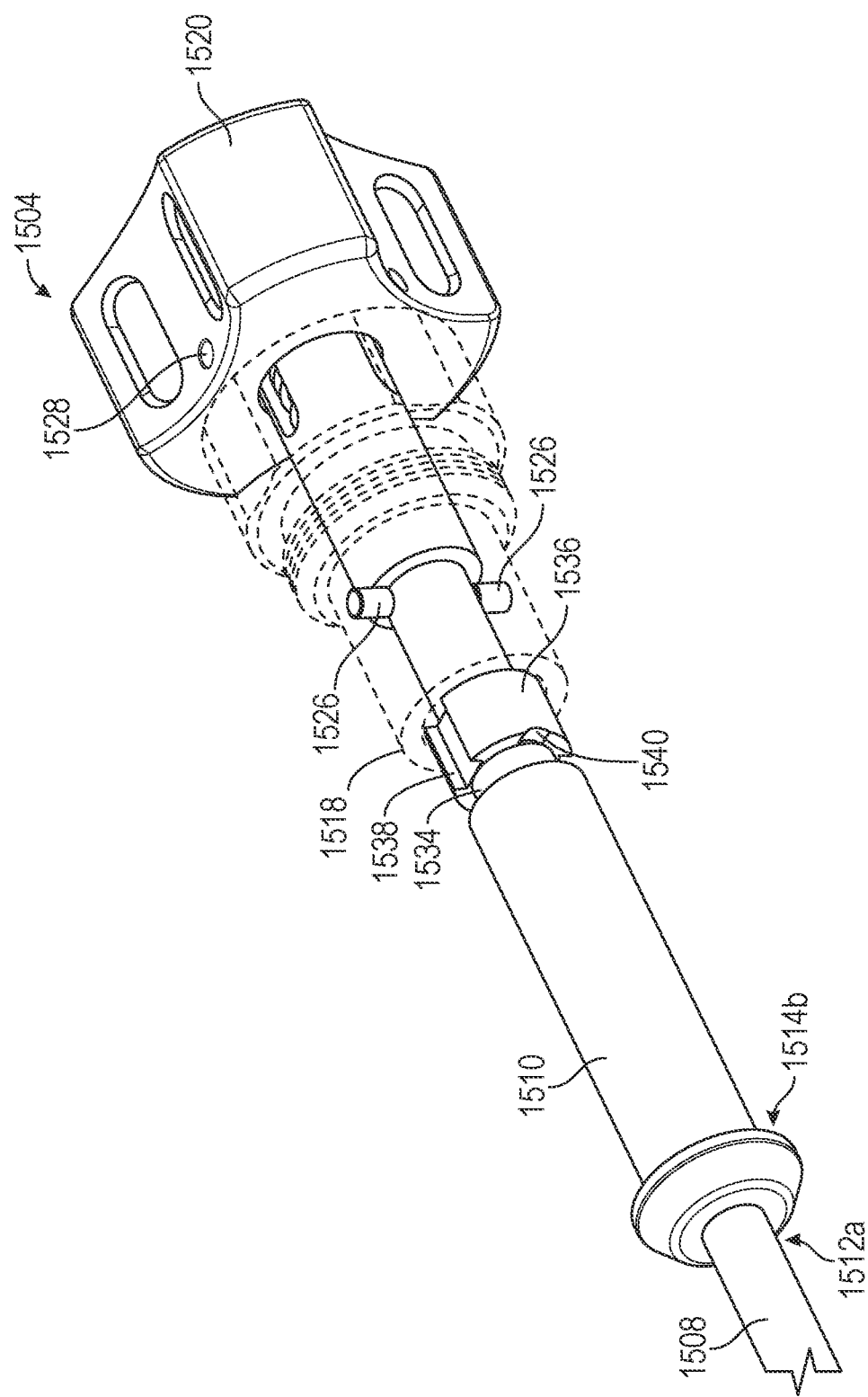

Turning now to FIGS. 15A-15C, wing driver subassembly 1500 is illustrated for some embodiments. FIGS. 15A and 15B illustrate a planar view and a cross-sectional view, respectively, of wing driver subassembly 1500. As discussed previously, wing driver subassembly 1500 may be configured to deploy wings 618a, 618b by causing longitudinal, distal movement of proximal plunger 626. Wing driver subassembly 1500 may also lock insertion instrument 1300 onto implant 600.

Wing driver subassembly 1500 may include a distal end 1502, a proximal end 1504, and a bore 1506 along longitudinal axis 1308. Wing driver subassembly 1500 may further comprise a shaft 1508 coupled to an inner sleeve 1510. Shaft 1508 may be coupled at a proximal end 1512a to a distal end 1514b of inner sleeve 1510. In some embodiments, shaft 1508 is welded to inner sleeve 1510. In some embodiments, shaft 1508 is coupled to inner sleeve 1510 via fasteners, adhesives, or the like. Shaft 1508 may have a hex-shaped distal tip 1516 for coupling to the hex-shaped non-threaded portion 906 of proximal plunger 626.

Inner sleeve 1510 may be received within and extend through a second sleeve 1518 and may partially extend within a wing deployment knob 1520. When shaft 1708 is coupled to proximal plunger 626, knob 1520 may be moved forward (i.e., distally) to deploy wings 618a, 618b via distal movement of proximal plunger 626. When implant 600 is in the final position with wings 618a, 618b engaged with the cortical bone 1206 and compressive body 604 engaged with the ilium 104, knob 1520 may be rotated to disengage knob 1520 from proximal plunger 626. A proximal surface 1522a of outer sleeve 1514 may abut a distal surface 1524 of wing deployment knob 1520. Outer sleeve 1514 may be coupled to inner sleeve 1510 via pins 1526. Inner sleeve 1510 may be coupled to wing deployment knob 1520 via pins 1528.

A first spring 1530 may be received on an outer surface of inner sleeve 1510. First spring 1530 may be concentric with inner sleeve 1510. The first spring 1530 may bias (i.e., spring-load) shaft 1508 to maintain engagement of shaft 1508 with proximal plunger 626, i.e., first spring 1530 biases shaft 1508 distally. First spring 1530 may be bounded by a distal surface 1522b of outer sleeve 1514 and a distal end 1514b of inner sleeve 1510. As discussed below, shaft 1508 may be locked in a retracted position by overcoming the spring force of first spring 1530.

A second spring 1532 may be received within outer sleeve 1514. The second spring 1532 may bias wing deployment knob 1520 proximally, i.e., away from implant 600. The second spring 1532 may also transfer axial force applied distally to knob 1520 into outer sleeve 1514, into handle 1408, and then into main body 602, which is connected to implant driver subassembly 1600 as discussed further below. Outer sleeve 1514 includes external threads 1533 for engaging with internal threads 1418. Transferring this axial force reduces the force transferred to shaft 1508 and proximal plunger 626 to reduce the risk of inserting implant 600 too far medially, which risks damaging the neuroforamen as previously discussed. Furthermore, transferring the axial force as described reduces the risk of implant 600 being forced off the end of insertion instrument 1300. The axial force is typically received from the surgeon pressing on wing deployment knob 1520 distally along longitudinal axis 1308 to advance the insertion instrument 1300 into the patient. Accordingly, second spring 1532 works to reduce the force transferred to implant 600. Additionally, the pinned connection between knob 1520 and inner sleeve 1510 allows for rotation of knob 1520 to rotate inner sleeve 1510 and, thereby shaft 1508 for decoupling shaft 1508 from implant 600 after the wings 618a, 618b are deployed. Further, knob 1520 may be rotated to rotate shaft 1508 and in turn proximal plunger 626 to thread threaded portion 904 along internal threads 1004, thereby advancing proximal plunger 626 distally to deploy wings 618a, 618b. Thus, deploying wings 618a, 618b may comprise rotating wing deployment knob 1520 to rotate 1508 and, in turn, threaded portion 904 along internal threads 1004 to thread proximal plunger 626 distally relative to main body 602.

Referring now to FIG. 15C, a perspective view of proximal end 1504 of wing driver subassembly 1500 is illustrated for some embodiments. For clarity of illustration, first spring 1530 is not shown in FIG. 3C, and second sleeve 1518 is illustrated transparently (as indicated by the dashed lines). As shown, inner sleeve 1510 may include a circumferential groove 1534 that defines a raised portion 1536 proximally from circumferential groove 1534. Additionally, inner sleeve 1510, including raised portion 1536 may have a diameter or width smaller than an inner diameter or width of second sleeve 1518 such that inner sleeve 1510 can be moved longitudinally within second sleeve 1518. For example, the knob 1520 may be pulled proximally to move inner sleeve 1510 within second sleeve 1518. Distal end 1514b may be flanged and have a diameter or width larger than the inner dimension of second sleeve 1518, thereby limiting the proximal travel of inner sleeve 1510.

The raised portion 1536 may include two longitudinal grooves 1538 spaced 180 degrees apart from one another. Additionally, inner sleeve 1510 may include two circular grooves 1540 spaces radially from two longitudinal grooves 1538 on raised portion 1536. The grooves 1534, 1538, 1540 may enable shaft 1508 to be placed in a locked position. To lock the shaft 1508, wing deployment knob 1520 may be pulled proximally to move inner sleeve 1510 within second sleeve 1518. Two longitudinal grooves 1538 may be aligned with pins 1526 such that two longitudinal grooves 1538 can slide by pins 1526. Inner sleeve 1510 may be moved such that circumferential groove 1534 is in line with pins 1526, i.e., circumferential groove 1534 and pins 1526 are within substantially the same lateral plane. Once in this position, inner sleeve 1510 can be rotated to align pins 1526 with two circular grooves 1540, and pins 1526 may sit in two circular grooves 1540 to lock shaft 1508 in this retracted position. When pins 1526 are engaged with two circular grooves 1540, pins 1526 may prevent distal movement of inner sleeve 1510 and, therefore, shaft 1508 as well. Pulling inner sleeve 1510 proximally may require overcoming the spring force of first spring 1530. Additionally, retracting wing driver subassembly 1500 enables the distal tip 1616 of shaft 1610 to flex inward when coupling implant driver subassembly 1600 to the implant 600. To unlock shaft 1508, inner sleeve 1510 may be pulled proximally to unseat pins 1526 from two circular grooves 1540, and then inner sleeve 1510 may be rotated to realign pins 1526 with two circular grooves 1540 such that inner sleeve 1510 can be moved distally.

Figure 16A:
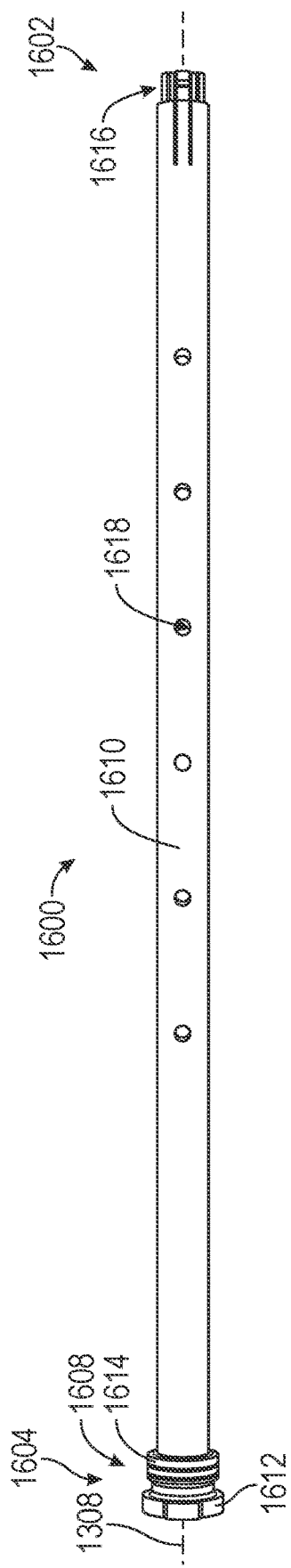
FIGS. 16A-16C illustrate an implant subassembly of the second insertion instrument for some embodiments.
Figure 16B:
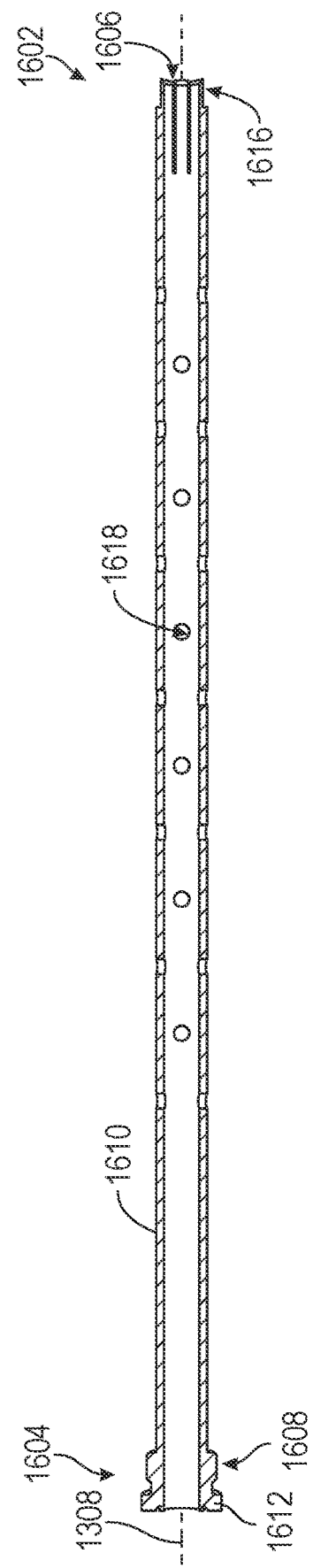

FIGS. 16A-16B illustrate a planar view and a cross-sectional view, respectively, of the implant driver subassembly 1600 for some embodiments. Implant driver subassembly 1600 may comprise a distal end 1602, a proximal end 1604, and a bore 1606 extending along longitudinal axis 1308 from distal end 1602 to proximal end 1604. At proximal end 1604, implant driver subassembly 1600 may comprise a collar 1608. A shaft 1610 may be coupled to extend from collar 1608. Collar 1608 may comprise a flanged portion 1612 that abuts a shoulder 1426 of connecting member 1410 such that implant driver subassembly 1600 is prevented from moving distally past shoulder 1426. Collar 1608 may also comprise external threads 1614 for threadedly engaging with an internal collar 1310 (see FIG. 13B) of insertion instrument 1300. Distal end 1602 may include a distal tip 1616. Distal tip 1616 may couple to proximal end 612 as described above with respect to distal tip 1616. A plurality of openings 1618 may extend along shaft 1610 and may aid in cleaning insertion instrument 1300, along with overall weight reduction of insertion instrument 1300. As previously discussed, implant driver subassembly 1600 can be rotated by rotation of collar 1608. Distal tip 1616 may couple to main body 602 such that rotating shaft 1610 rotates implant 600 for inserting implant 600 into the patient.

Figure 16C:
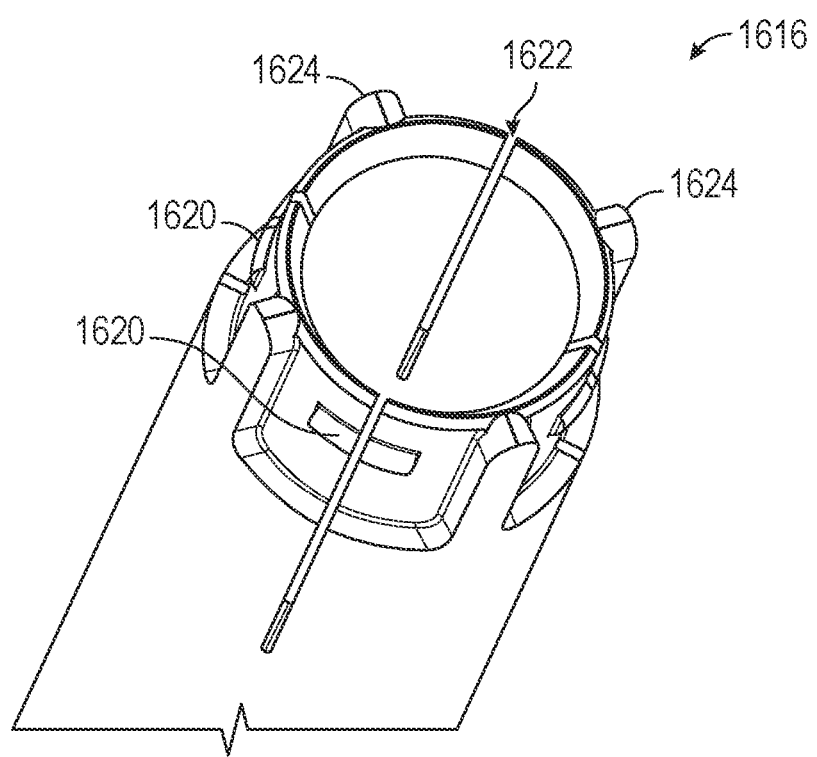

FIG. 16C illustrates distal tip 1616 for some embodiments. As shown, distal tip 1616 comprises a plurality of detents 1620 circumferentially around the tip. Distal tip 1616 may also comprise a plurality of tangs 1622 bisecting each of the detents 1620. The detents 1620 may interface with recesses 1012 on the inner surface of main body 602. Tangs 1622 may be configured to provide additional flexure (e.g., radial flexure) in distal tip 1616, which may aid in coupling distal tip 1616 to proximal end 612. Distal tip 1616 may further comprise a plurality of cutouts 1624, with each cutout 1624 disposed between adjacent detents 1620 on the exterior of distal tip 1616. The cutouts 1624 may be received within openings 1008 on proximal end 612. Accordingly, distal tip 1616 may couple to proximal end 612 of main body 602 with detents 1620 engaging recesses 1012 (see FIG. 6B) and cutouts 1624 fitting in the openings 1008. When coupling insertion instrument 1300 to implant 600, wing driver subassembly 1500 and compressive body drive subassembly 1700 may be retracted such that distal tip 1616 is the distal most component of insertion instrument 1300, which may enable the inward flexing of distal tip 1616 for coupling shaft 1610 to implant 600. Once coupled, shaft 1610 may be rotationally driven, using handle 1408, to rotate implant 600 for inserting implant 600 into the patient. The self-drilling features at distal end 610 may then self-drill implant 600 through ilium 104 and into the sacrum 106.

FIGS. 17A-17B illustrate the compressive body driver subassembly 1700 for some embodiments. Compressive body driver subassembly 1700 may comprise a distal end 1702, a proximal end 1704, and a bore 1706 extending from distal end 1702 to proximal end 1704 along longitudinal axis 1308. Compressive body driver subassembly 1700 may further include a shaft 1708 having a distal tip 1710, which may be configured as a castle nut for engaging with receiving portions 1110 on compressive body 604.

At proximal end 1704, compressive body driver subassembly 1700 may include a threaded boss 1712, a connecting member 1714 connecting shaft 1708 to threaded boss 1712, and a knob 1716. Pins 1718 may couple shaft 1708 to connecting member 1714 via a J-slot 1720 formed in connecting member 1714 as shown in FIG. 17B. Knob 1716 may be seated on shaft 1708. Knob 1716 may be coupled to shaft 1708 such that rotating knob 1716 also rotates shaft 1708. Accordingly, the surgeon may rotate knob 1716 to rotate shaft 1708, which rotates compressive body 604 along proximal end 612 via threaded engagement of external threads 1006 and internal threads 1112, allowing the compression applied across SI joint 102 to be adjusted. The position of shaft 1708 may be locked via J-slot 1720. A corresponding J-slot 1720 may be opposite the illustrated J-slot 1720. For example, the surgeon may have shaft 1708 locked via the J-slot 1720 while the surgeon connects wing driver subassembly 1500 and implant driver subassembly 1600 to proximal plunger 626, and proximal end 612, respectively, before unlocking shaft 1708 and coupling distal tip 1710 to compressive body 604. The pins 1718 may be seated in J-slot 1720 such that shaft 1708 can be moved relative to connecting member 1714, and pins 1718 may ride within J-slot 1720. Accordingly, shaft 1708 may be pulled proximally, e.g., via pulling knob 36 proximally, and then rotated to align pins 1718 into a groove 1722 of the J-slot, thereby preventing distal movement of shaft 1708 until pins 1718 are unseated from the grooves 1722.

A proximal end of the connecting member 1714 may be received within threaded boss 1712 and coupled thereto. A bottom surface 1724 may interpose a first washer 1726a and a second washer 1726b to couple connecting member 1714 to threaded boss 1712. A collar 1728 may be coupled to an outer surface of connecting member 1714 and concentric therewith. The collar 1728 may be distal from the second washer 1726b and may have an upper surface abutting a bottom surface of the second washer 1726b. Washers 1726a, 1726b may be plastic washers configured to prevent galling of metal on metal parts (i.e., between threaded boss 1712 and connecting member 1714).

The threaded boss 1712 may include a pair of flexible tabs 1730 with teeth 1732. The tabs 1730 and teeth 1732 provide an auto-locking feature for insertion instrument 1300. As handle subassembly 1400 is rotated, ratchet teeth 1422 engage with teeth 1732 to lock handle subassembly 1400 with threaded boss 1712 and, thereby compressive body drive subassembly 1700. Rotation of threaded boss 1712 in a first direction (e.g., clockwise) may lock handle subassembly 3200 to compressive body driver subassembly 1700, while rotation of a threaded boss 1712 in a second, opposite direction (e.g., counterclockwise) may unlock handle subassembly 3200 from compressive body driver subassembly 1700 to allow for disassembly of insertion instrument 1300. Meanwhile, shaft 1708 may be configured to rotate independently from rotation of threaded boss 1712.

Compressive body driver subassembly 1700 may additionally include a spring 1734. Spring 1734 may be received within a proximal end of shaft 1708 and may be bounded by a distal face 1736 of connecting member 1714 and a shoulder 1738 of shaft 1708. Similar to second spring 1532 discussed above, spring 1734 may bias shaft 1708 distally such that the connection between distal tip 1710 and compressive body 604 can be maintained. Because the compressive body 604 will be traveling distally along main body 602 as compressive body 604 is threaded by subassembly 1700, providing this spring-loading allows distal tip 1710 to maintain the connecting between shaft 1708 and compressive body 604.

In some embodiments, insertion instruments 400, 1300 comprises titanium or a titanium alloy. In some embodiments, insertion instruments 400, 1300 comprise stainless steel. In some embodiments, insertion instruments 400, 1300 comprise a polymer, a plastic, a bioabsorbable material, or any combination thereof. For example, insertion instruments 400, 1300 may be formed from polyacrylamide or IXEF®. In some embodiments, insertion instrument 400, 1300 is additively manufactured and may be formed from RULON, PEEK, or the like. In some embodiments, at least a portion of insertion instrument 400, 1300 is radiopaque or radiolucent. In some embodiments, insertion instrument 400, 1300 is disposable, e.g., configured for single use.

In some embodiments, one or more components of insertion instruments 400, 1300 are coated in a biocompatible, corrosion resistant material to help protect and/or strengthen the component. For example, some or all portions of insertion instruments 400, 1300 may be advantageously reinforced with a coating material to increase the durability of the components while maintaining safety to the patient by the coating material being of a biocompatible substance. Such a coating material may be applied specifically to components of insertion instruments 400, 1300 that come into contact with tissue of the patient. In some embodiments, the coating material may be an anodized metal. In some embodiments, the coating material may be formed by an electroplating process, such as a hard chromium electroplating process. For example, in some embodiments, the coating material may be MEDCOAT 2000™. In some embodiments, the thickness of the coating material may be between about 1 μm to about 15 μm. In some embodiments, the coating material may be between about 2 μm to about 10 μm.

Lateral SI Implant Insertion Method

Figure 18:
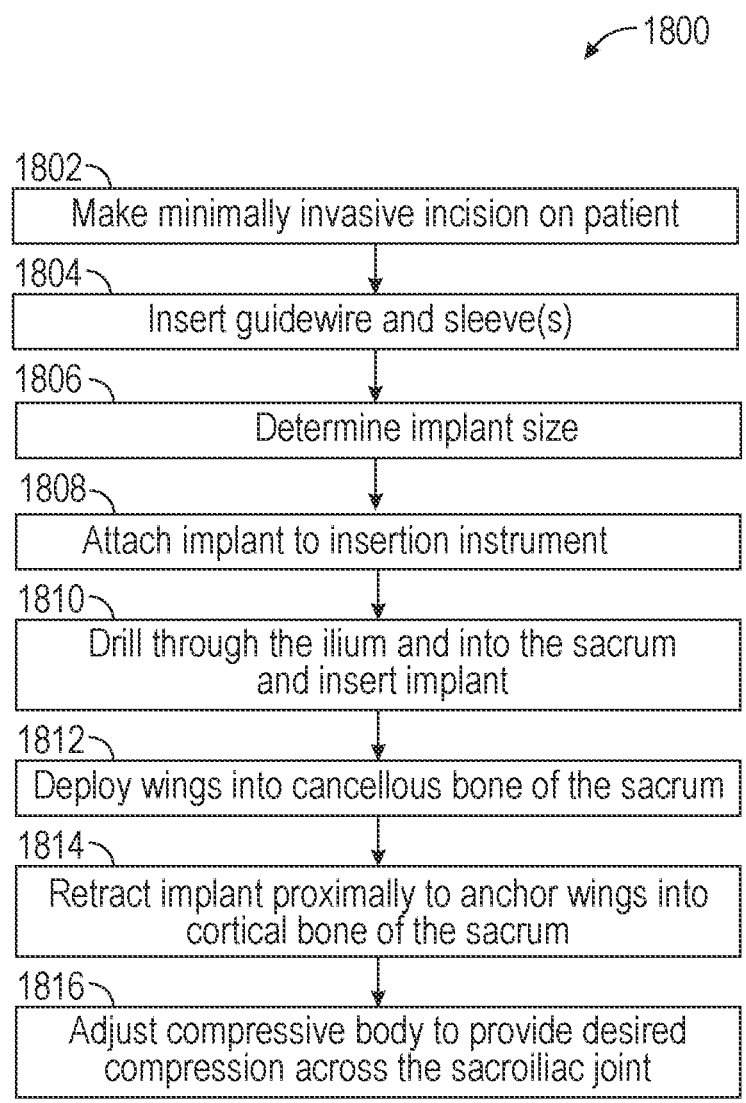
FIG. 18 illustrates an operational method for inserting the lateral SI implant for some embodiments.

Turning now to FIG. 18, a method 1800 for insertion and implantation of implant 600 using insertion instrument 1300 is illustrated for some embodiments of the present disclosure. One or more implants 600 may be inserted across the SI joint 102 to provide fusion and stabilization thereof. In some embodiments, the implant 600 is inserted at the S1 level of the spine. Placement of the implant 600 may be done to avoid damaging the neuroforamen that are medial from the sacrum 106. While method 1800 is discussed with respect to inserting implant 600, implant 108*b* may similarly be inserted without departing from the scope of the present disclosure.

At step 1802, a minimally invasive incision may be made on the patient. As discussed above, minimally invasive incisions reduce blood loss, recovery time, and hospital stay, among other benefits, as compared to open surgery. However, it is contemplated that embodiments herein may be practiced in an open surgery. In some embodiments, the incision is made to provide lateral access to the patient such that the implant 600 may be inserted across the SI joint 102. In some embodiments, a separate incision is made for each implant 600 that is inserted. In some embodiments, each implant 600 is inserted through the same incision. In some embodiments, one, two, or three implants are inserted for the SI joint fusion procedure.

Next, at step 1804, a guidewire 1202 and sleeves 1204 may be inserted through the incision to provide access to the target space. The guidewire 1202 may be inserted (e.g., tapped or using any other method) through the incision and advanced into the sacrum 106 where the surgeon wishes to insert the implant 600. When multiple implants are inserted, a parallel pin guidewire tool may be used to insert the guidewires 1202 parallelly through the incision. Soft tissues may then be dilated using one or more dilators or sleeves 1204. In some embodiments, the soft tissues are dilated by sequentially inserting larger width or diameter dilators or sleeves 1204 over the guidewire 1202. Each successive sleeve 1204 may be inserted over the previous sleeve 1204. After the last sleeve 1204 has been added, the smaller diameter sleeves 1204 may be removed, leaving the guidewire 1202 in place. In some embodiments, the largest sleeve 1204 is left over the guidewire 1202.

Next, at step 1806, the size of the implant 600 for the patient may be determined. In some embodiments, the size of the implant 600 is determined based on the depth that guidewire 1202 is inserted into the patient. In some embodiments, the size of the implant 600 is determined based on a distance between the outer surface of ilium 104 (or a distalmost surface of sleeve 1204, which may be docked against the outer surface of ilium 104) and a point on guidewire 1202 within sacrum 106. As discussed further below, guidewire 1202 may comprise an alignment indicator that may be visible under fluoroscopy such that the surgeon can determine the location of the guidewire 1202 within the patient. Generally, any method of determining the requisite size for the implant 600 based on the anatomy of the patient is within the scope hereof. Different sized implants 600 may have different lengths but the same or substantially similar diameters.

Next, at step 1808, the implant 600 may be coupled to the insertion instrument 1300. As previously discussed, the insertion instrument 1300 may have a wing driver subassembly 1500 that couples to non-threaded portion 906 on proximal plunger 626, an implant driver subassembly 1600 that couples to proximal end 612 of main body 602, and a compressive body driver subassembly 1700 that couples to compressive body 604. As Thereafter, at step 1810, the surgeon may drill into the patient, through the ilium 104 and into the sacrum 106 to provide an access space for inserting the implant 600. In some embodiments, the drilling is self-drilling of implant 600, with the surgeon rotationally driving the implant using insertion instrument 1300 to drill into the patient. In some embodiments, a drill is used. The drill may be configured to be inserted over the guidewire 1202 to ensure that the hole is made at the desired implantation location. Drilling also provides distraction of the target space. As discussed above, implant 600 may have an externally threaded distal end 610 that can distract the target space to aid in implantation. Furthermore, self-harvesting features, such as an open distal tip, slots, flutes, or any combination thereof may be provided such that implant 600 self-harvests bone during insertion. Additionally, implant 600 may be formed with a substantially blunt distal end 610 to reduce the likelihood that the implant pierces through the innermost cortical wall of the sacrum 106, thereby protecting the neuroforamen. Implant 600 may also be packed with bone graft material to promote bony fusion. Step 1810 may also comprise inserting the implant 600 into the sacrum 106, which may be done as part of the self-drilling process, or after drilling into the sacrum 106 and by advancing the implant 600 over guidewire 1202.

Once implant 600 is at the implantation site, at step 1812, the wings may be deployed into the cancellous bone 1208 of the sacrum 106. The cancellous bone 1208 is softer than the cortical bone 1206; thus, it is advantageous to deploy the wings in the cancellous bone 1208 because less force will be required. As discussed above, plunger 624 may be formed with a cannulation for post packing or injection of bone graft through the cannulation after deployment of the wings. In some embodiments, the wings are deployed by driving implant driver subassembly 1600 with handle subassembly 1400. In turn, proximal plunger 626 is threaded along internal threads 1004, thereby moving proximal plunger 626 longitudinally, and the longitudinal movement may move the wings between the open configuration to the closed configuration.

Next, at step 1814, implant 600 may be retracted proximally to anchor the wings against the cortical bone 1206 of the sacrum 106. The proximal retraction may be carried out by the operator pulling insertion instrument 1300 proximally. In some embodiments, the proximal retraction is performed by handle subassembly 1400 being pulled proximally. Thus, a distal anchor is formed by the wings. The distal anchor is selectively positioned in the open configuration and the closed configuration. The wings may comprise a substantially flat bottom surface to dock against cortical bone 1206. In some embodiments, the wings comprise fangs 814 protruding from the bottom surface to anchor into the cortical bone and to counter rotation of the implant 600. Additionally, implant 600 may comprise a substantially smooth body located proximally from the threaded distal end 610 that aids in retracting implant 600.

At step 1816, the compressive body 604 may be adjusted to adjust the compression applied across the SI joint 102. As the compressive body is advanced distally, the compression across the SI joint 102 is increased. Increasing compression improves the fusion and stabilization of the SI joint 102 as micromotions therein are reduced. In some embodiments, the compressive body is advanced distally until recesses 1108 are docked against an outer surface of the ilium 104. In some embodiments, the compressive body is advanced distally such that recesses 1108 are partially embedded within the ilium 104. Thus, a proximal anchor is formed. In some embodiments, compressive body 604 is advanced by rotating shaft 1708 using compressive body driver subassembly 1700.

In some embodiments, the above-described method 1800 may be provided as instructions with a surgical kit and/or with the implant 600. For example, the surgical kit may comprise the instructions, one or more implants 600, insertion instrument 1300, guidewire 1202, sleeves 1204, and any other instrumentation necessary to complete the SI joint fusion procedure. An exemplary surgical kit is discussed below with respect to FIG. 19.

In some embodiments, all or part of implant 600 may be composed of titanium or a titanium alloy. In some embodiments, all or part of implant 600 may be composed of stainless steel. In some embodiments, all or part of implant 600 may be composed of a polymer or a bioabsorbable material. In some embodiments, all or part of implant 600 may be composed of allograft (i.e., cadaver bone), such as cortical allograft. In some embodiments, implant 600 may be formed by an additive manufacturing process. In some embodiments, implant 600 may be formed by machining and/or molding. In some embodiments, implant 600 coated on at least one surface thereof. In some embodiments, at least one outer surface of the implant 600 may be coated with hydroxyapatite (HA). In some embodiments, multiple surfaces may be coated with HA. In some embodiments, implant 600 is packed with bone graft, such as demineralized bone matrix.

Exemplary Surgical Kit

Figure 19:
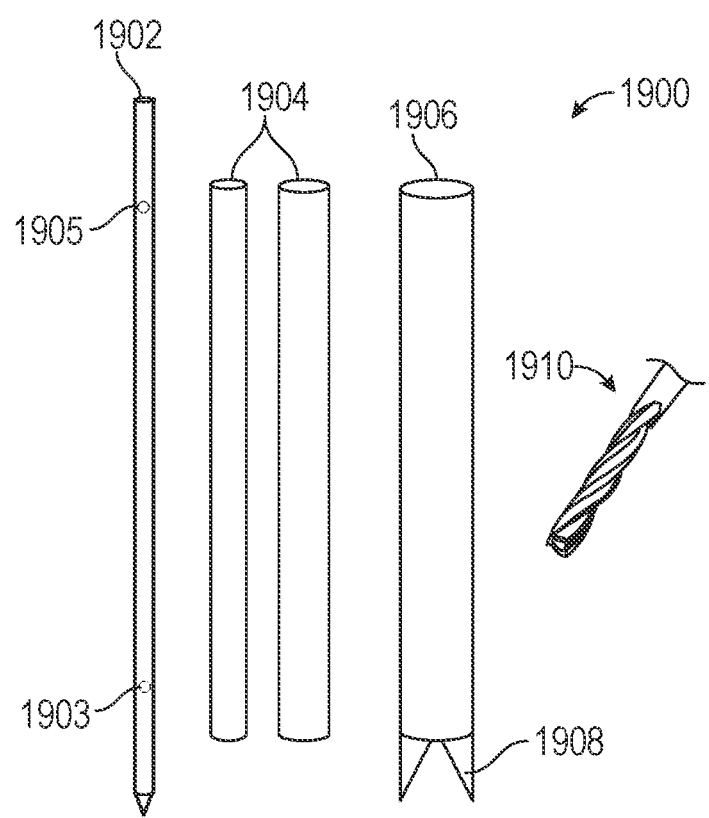
FIG. 19 illustrates a surgical kit for some embodiments.

FIG. 19 illustrates a surgical kit 1900 for preparing a target space (e.g., SI joint 102) for insertion of an implant in accordance with embodiments of the present disclosure. Surgical kit 1900 may comprise tools, along with implants 108a, 108b, 110, 200, 300, 600, insertion instruments 400, 1300 for inserting the implants, or any combination thereof. Surgical kit 1900 may include a first set of tools for inserting the lateral SI implants and a second set of tools for inserting the posterior SI implants. Both sets of tools may include all or a subset of the tools discussed herein.

In some embodiments, the tools comprise at least one guidewire 1902. Guidewire 1902 may be inserted into a minimally invasive incision and, under fluoroscopy, guidewire 1902 may be advanced to locate the target space where it is desired to place implant 300, 600. Guidewire 1902 may correspond to guidewire 1202 discussed above. In some embodiments, the tools comprise one or more dilators 1904. When inserting the lateral SI implant 600, a guidewire 1902 may be provided with an alignment indicator 1903 on a distal end of guidewire 1902 used to ensure guidewire 1902 is correctly aligned in the patient. The alignment indicator 1903 may be a feature on the distal end of the guidewire 1902 that is visible under fluoroscopy such that the surgeon can see the location of the alignment indicator 1903 relative to patient's anatomy to ensure the guidewire 1902 is at the correct depth into the sacrum 106 as viewed in the medial direction. For example, the alignment indicator 1903 may be a hole (as shown), a groove, a notch, a contrasting mark, or the like.

In some embodiments, the reference point for inserting guidewire 1902 is the cortical bone 1206 of sacrum 106 that is medial to the articular surface of the SI joint 102. That is, the alignment indicator 1903 may be placed in cancellous bone 1208 of sacrum 106 to ensure that wings 618a, 618b can deploy. As discussed previously, because the cancellous bone 1208 is softer than cortical bone 1206, the wings 618a, 618b are able to deploy into cancellous bone 1208. When the guidewire 1902 is in this position, the guidewire 1902 provides a representation of the final placement of implant 600. A sizing instrument can then be placed against the lateral surface of ilium 104, over guidewire 1902. A marking feature 1905 (such as a laser mark) may be on a proximal end of the guidewire 1902, and the location of the marking feature 1905 relative to indicators on the sizing instrument (not shown) can provide an indication of the size of the implant 600 that should be inserted into the patient. For example, the sizing instrument may be integrated into a dilator (e.g., sleeve 1204 shown in FIG. 12) such that the dilator includes indicators that dictate the size of implant 600 to implant. For example, if, when guidewire 1902 is inserted into cancellous bone 1208, marking feature 1905 is proximate to a first indicator 1206a (FIG. 12), the surgeon may know to use an implant size based on the first indicator. If the marking feature 1905 is instead proximate to a second indicator 1206b (FIG. 12) that is longitudinally spaced form the first indicator 1206a, the surgeon may know to use a different size implant 600.

Dilators 1904 may be hollow tubes that are placed over guidewire 1902 to create a working channel for insertion of an implant. Dilators 1904 may be provided in increasing sizes such that a larger sized dilator 1906 may be placed over a smaller-sized dilator to dilate the target space.

In some embodiments, the tools comprise a final dilator 1906. The final dilator may have a larger size than dilators 1904 such that final dilator 1906 may be placed over the largest dilator 1906. Additionally, in some embodiments, the final dilator 1906 may have one or more tangs 1908. The tangs 1908 may be configured to dock into the SI joint 102 for preparing the target space for inserting the posterior SI implant 300. In some embodiments, final dilator 1906 comprises at least one tang 1908. In some embodiments, final dilator 1906 comprises two or more tangs 1908. For example, a first tang 1908 may engage with the ilium 104 and a second tang 1908 may engage with the sacrum 106. Docking one or more tangs 1908 with ilium 104 and/or sacrum 106 may provide positive feedback to the surgeon to indicate that SI joint 102 was correctly located. Final dilator 1906 may also provide further distraction to SI joint 102 to prepare SI joint 102 for implantation of implant 300. In some embodiments, tangs 1908 are wedge shaped. Other shapes are within the scope hereof. Generally, for implanting a posterior SI implant 200, 300, final dilator 1906 may have a distal end that is configured for engaging with bone such that final dilator 1906 can dock into the target space. Providing a final dilator 1906 as discussed herein may be advantageous in correctly locating SI joint 102, which may be difficult from a posterior approach due to the irregular shape of the joint that makes the joint difficult to view under fluoroscopy. Accordingly, with the positive feedback provided by final dilator 1906, the surgeon may be assured that the correct location for inserting implant 200, 300 has been located. For inserting the lateral SI implant 108b, 600, no tangs may be included on the final dilator. Through final dilator 1906, implant 300 and insertion instrument 400 may be inserted when implanting implant 600.

In some embodiments, the tools comprise a drill bit 1910. Drill bit 1910 may be used for drilling a pilot hole to access the target space. In some embodiments, drill bit 1910 is cannulated, as shown, such that drill bit 1910 may be inserted over guidewire 1902. In some embodiments, the tools further comprise a decorticator (not shown) for roughening the target space. The decorticator may likewise be cannulated for insertion over guidewire 1902.

As discussed previously, a tool may be provided to ensure the proper trajectory is used for inserting lateral implant 108a through window 202 when interlocking implants 108a, 200. In some embodiments, the tool is configured to be placed over the guidewire 1902 and at least partially through window 202 to provide a pathway for inserting the lateral SI implant 108a. It is contemplated the trajectory tool could engage with the implant 200 to maintain the pathway from the patient's skin through window 202.

Single Procedure Posterior and Lateral SI Joint Fusion Method

Figure 20:
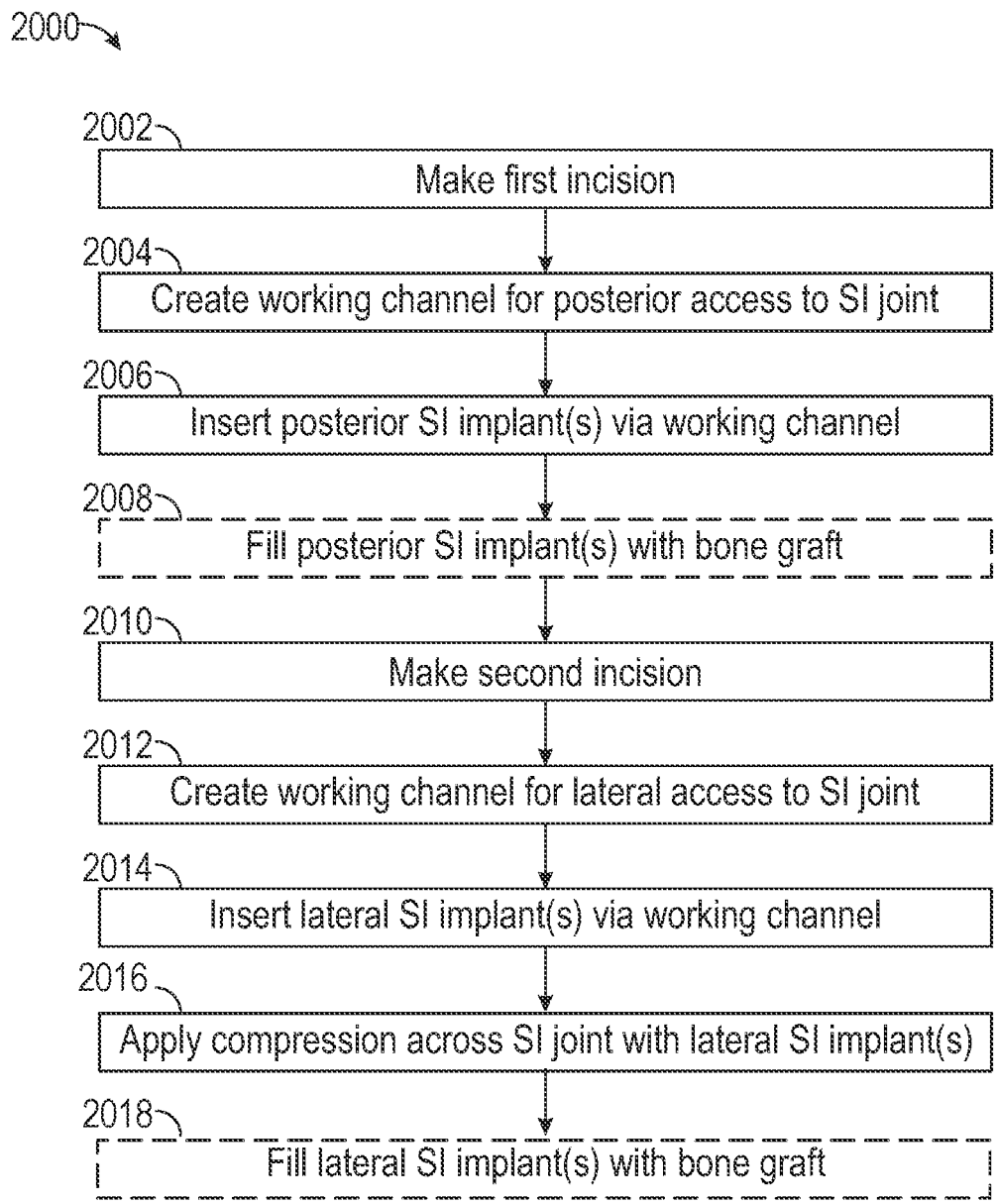
FIG. 20 illustrates an exemplary method in accordance with embodiments of the present disclosure.

A method 2000 for a single procedure lateral and posterior SI fusion is illustrated with respect to FIG. 20. Method 2000 may be embodied as instructions provided with surgical kit 1900. The surgical procedure may take place with the patient in the prone position. The lumbar spine may be flexed and/or the lumbar spine may be elevated out of lordosis during the procedure.

Method 2000 may begin at step 2002 where a first incision for inserting the posterior SI implant 110 is created. The first incision may be a minimally invasive incision having a length of less than about two inches. Step 2002 may correspond to step 502 discussed above.

Next, at step 2004, a working channel for inserting the posterior SI implant 110 may be created. The working channel may be created by inserting a guidewire 1902 and inserting successively larger dilators 1904 over the guidewire 1902 to dilate the joint space. A final dilator 1906 may be inserted and may include tangs 1908 to dock against the ilium 104 and the sacrum 106. If needed, a pilot hole may be drilled. Additionally, decortication, and/or other joint preparation steps may be taken to create the working channel. Once the joint space is prepared, the guidewire 1902 and the final dilator 1906 may be the only instruments remaining in the patient.

At step 2006, the implant 108b, 300 may be inserted through the working channel using insertion instrument 400. For inserting implant 300, external threads 414 on rod 406 may couple to internal threads 316 in proximal section 302b and prongs 416 on shaft 408 may be coupled to recesses 318 in proximal section 302b. Once coupled, insertion instrument 400 may be rotationally driven to insert implant 300 into SI joint 102. Cannula 310 and bore 404 allow for implant 300 and insertion instrument 400 to be inserted over guidewire 1902.

At optional step 2008, the implant 108b, 300 may be packed with bone graft. In some embodiments, implant 300 is filled with bone graft by inserting the bone graft through bore 404 in insertion instrument 400 and into cannula 310 in implant 300 while insertion instrument 400 and implant 300 are coupled. Generally, any type of bone graft may be used. Step 2008 may correspond to step 516 discussed previously. When multiple implants 108b, 300 are inserted into SI joint 102, steps 2002-2008 may then be repeated for each posterior SI implant 108b, 300 to be inserted.

After inserting the posterior SI implant(s), the lateral SI implant(s) may be inserted across the SI joint 102. Accordingly, at step 2010 a second incision for inserting the lateral SI implant 108b, 600 may be made. The second incision may likewise be a minimally invasive incision. Step 2010 may correspond to step 1802 discussed above.

Next, at step 2012, a working channel may be created. Step 2012 may be substantially similar to step 1804. The working channel may be created by inserting a guidewire 1902, and successively larger sleeves or dilators 1904, 1906 over the guidewire 1902 to dilate the target space. In some embodiments, a targeting instrument can be used to help the surgeon place the guidewire through the window 202 in implant 200. The guidewire 1902 may be inserted through ilium 104, across SI joint 102, and into sacrum 106. A pilot hole may be drilled through ilium 104 and into sacrum 106 if desired. Other preparatory steps may be taken to prepare the SI joint 102 for insertion of the lateral SI implant(s). When the joint space is prepared, guidewire 1902 and a single dilator 1906 may remain in the patient.

Thereafter, at step 2014, the lateral SI implant 108*b*, 600 may be inserted. The lateral SI implant 108*b*, 600 may be inserted via a lateral approach. As with implant 300, implant 600 may be inserted over the guidewire 1902. Insertion instrument 1300 may likewise be inserted over guidewire 1902. As discussed above with respect to FIGS. 2A and 2B, implant 600 may interlock with posterior SI implant 200 such that implant 600 is inserted through window 202 in posterior SI implant 200.

At step 2016, once implant 600 is at the implantation site, compression may be applied across SI joint 102 using implant 108*b*, 600. Wings 618*a*, 618*b* may be deployed and implant 600 retracted such that wings 618*a*, 618*b* engage with the cortical bone of the sacrum 106. Compressive body 604 may then be threaded along main body 602 to compress against ilium 104. For embodiments where implant 108*b* is used, the external threads may aid in compressing SI joint 102.

Next, at optional step 2018, bone graft may be inserted into implant 108*b*, 600. Like implant 300 and insertion instrument 400, implant 600 and insertion instrument 1300 are cannulated such that bone graft can be inserted through the cannulas to fill implant 600 with bone graft. Steps 2010-2016 (or a subset thereof) may then be repeated for each additional lateral SI implant 600 to be inserted across SI joint 102 to transfix SI joint 102.

It will be appreciated that method 2000 may be suitably modified without departing from the scope of the present disclosure. For example, while method 2000 is discussed with respect to inserting a posterior SI implant before the lateral SI implant, the SI joint fusion procedure may instead involve inserting the lateral SI implant(s) before inserting the posterior SI implant(s). Furthermore, the steps may generally be taken in any order. For example, steps 2002 and 2010 may be taken first. As another example, each working channel for the respective implant 300, 600 may be created before inserting either implant 300, 600. As yet another example, when interlocking implant 600 with posterior SI implant 200, bone graft may be added to posterior SI implant 200 after implant 600 is inserted through window 202. Furthermore, various insertion methods/techniques for inserting the posterior SI implant into the intra-articular space and the lateral SI implant across the SI joint 102 to transfix the joint may be used. For example, the posterior SI implant may be inserted via an oblique approach.

While embodiments of the present disclosure are generally directed with respect to inserting implants 300, 600 across SI joint 102, it will be appreciated that either or both of implants 300, 600 may be used in various other body regions and joint spaces without departing from the scope hereof. For example, implant 600 and posterior SI implant 200 may be interlocked at other joint spaces. For example, implant 600 may have use in repairing a trocar fracture and may be used to compress on the head of the femur. As another example, implant 300 may be used in the foot and ankle for fixation.

Many different arrangements of the various components depicted, as well as components not shown, are possible without departing from the scope of the claims below. Embodiments of the present disclosure have been described with the intent to be illustrative rather than restrictive. Alternative embodiments will become apparent to readers of this disclosure after and because of reading it. Alternative means of implementing the aforementioned can be completed without departing from the scope of the claims below. Certain features and sub-combinations are of utility and may be employed without reference to other features and sub-combinations and are contemplated within the scope of the claims. Although the present disclosure has been described with reference to the embodiments illustrated in the attached drawing figures, it is noted that equivalents may be employed, and substitutions made herein, without departing from the scope of the present disclosure as recited in the claims.

The invention claimed is:

1. A method for sacroiliac (SI) joint fusion, comprising:
making a first incision on a patient to provide posterior access to an SI joint of the patient;
inserting, via a posterior approach, using a first insertion instrument, and through the first incision, a posterior SI implant into the SI joint such that the posterior SI implant engages with both a sacrum and an ilium of the patient,
wherein the posterior SI implant comprises external threads entirely along a length thereof and has a cannula along a longitudinal axis,
wherein inserting the posterior SI implant with the first insertion instrument comprises rotationally driving the posterior SI implant to thread the posterior SI implant into the SI joint;
making a second incision on the patient to provide lateral access to the SI joint;
inserting, via a lateral approach, using a second insertion instrument, and through the second incision, a lateral SI implant across the SI joint,
wherein the lateral SI implant comprises:
a distal end configured to engage the sacrum; and
a proximal end configured to engage the ilium; and
using the second insertion instrument, compressing the distal end against cortical bone of the sacrum, and compressing the proximal end against the ilium, thereby applying compression across the SI joint and to the posterior SI implant with the lateral SI implant.

2. The method of claim 1, wherein the first incision and the second incision are minimally invasive incisions having a length of less than two inches.

3. The method of claim 1, further comprising:
inserting bone graft into the posterior SI implant through the first insertion instrument and into the lateral SI implant through the second insertion instrument.

4. The method of claim 1, wherein the proximal end of the lateral SI implant comprises an adjustable compressive body and the method further comprises:
threading, using the second insertion instrument, the adjustable compressive body towards the distal end to adjust an amount of compression applied by the adjustable compressive body.

5. The method of claim 1,
wherein the distal end of the lateral SI implant comprises a pair of wings,
wherein the second insertion instrument is used to engage the pair of wings with the cortical bone of the sacrum, and
wherein engagement of the pair of wings retract the lateral SI implant towards the ilium.

6. The method of claim 1, wherein the posterior SI implant further comprises:
a distal section, a proximal section, and a central section between the proximal section and
the distal section, the central section comprising:
an interior core region adjacent the cannula;
a lattice structure located laterally between the interior core region and the external threads; and a plurality of openings extending through the interior core region and connecting the lattice structure to the cannula.

7. A method for sacroiliac (SI) joint fusion, comprising:
making a first incision on a patient to provide posterior access to an SI joint of the patient;
inserting, via a posterior approach, through the first incision, and using a first insertion instrument, a posterior SI implant into the SI joint such that the posterior SI implant engages with both a sacrum and an ilium of the patient,
wherein the posterior SI implant comprises:
a cannula along a longitudinal axis; and
a central section, comprising:
an interior core region adjacent the cannula; and
a lattice structure adjacent the interior core region;
making a second incision on the patient to provide lateral access to the SI joint;
inserting, via a lateral approach, through the second incision, and using a second insertion instrument, a lateral SI implant across the SI joint such that a distal end of the lateral SI implant is at least partially within the sacrum of the patient and a proximal end of the lateral SI implant is in contact with the ilium of the patient; and
using the second insertion instrument to engage a distal end of the lateral SI implant with cortical bone of the sacrum and to engage a proximal end of the lateral SI implant with the ilium, thereby applying compression across the SI joint and to the posterior SI implant with the lateral SI implant.

8. The method of claim 7, wherein each of the first incision and the second incision are minimally invasive incisions having a length of less than two inches.

9. The method of claim 7, wherein the lateral SI implant is a first lateral SI implant, the posterior SI implant is a first posterior SI implant, and further comprising:
inserting at least one of: a second lateral SI implant or a second posterior SI implant.

10. The method of claim 9, wherein the second posterior SI implant is inserted superiorly relative to the first posterior SI implant.

11. The method of claim 7,
wherein the posterior SI implant comprises a window therethrough, and
wherein inserting the lateral SI implant comprises inserting the lateral SI implant through the window of the posterior SI implant.

12. The method of claim 7, wherein at least one of the posterior SI implant or the lateral SI implant comprises a self-drilling distal end.

13. A method for sacroiliac (SI) joint fusion, comprising:
inserting, via a posterior approach, through a first incision on a patient and using a first insertion instrument, a posterior SI implant into an SI joint such that the posterior SI implant engages with both a sacrum and an ilium of the patient,
wherein the posterior SI implant comprises:
a cannula along a longitudinal axis; and
a central section, comprising:
an interior core region adjacent the cannula; and
a lattice structure adjacent the interior core region;
wherein inserting the posterior SI implant with the first insertion instrument comprises rotationally driving the posterior SI implant to thread the posterior SI implant into the SI joint;
filling, when the posterior SI implant is in the SI joint, the posterior SI implant with bone graft by inserting the bone graft through the first insertion instrument and into the posterior SI implant;
inserting, via a lateral approach, through a second incision on the patient and using a second insertion instrument, a lateral SI implant across the SI joint,
wherein a distal end of the lateral SI implant is configured to engage with cortical bone of the sacrum, and
wherein a proximal end of the lateral SI implant is configured to engage with the ilium; and
using the second insertion instrument, engaging the distal end of the lateral SI implant against the cortical bone of the sacrum and engaging the proximal end of the lateral SI implant against the ilium, thereby applying compression across the SI joint and to the posterior SI implant.

14. The method of claim 13, wherein the distal end of the lateral SI implant comprises a pair of deployable wings housed within the lateral SI implant in a closed configuration and deployed from within the lateral SI implant in an open configuration.

15. The method of claim 13, wherein the method further comprises:
inject bone graft into the lateral SI implant or the posterior SI implant.

16. The method of claim 15, wherein the bone graft is injected through the first insertion instrument or the second insertion instrument.

17. The method of claim 13, wherein inserting the lateral SI implant comprises self-drilling the lateral SI implant through the ilium and into the sacrum.

18. The method of claim 13, wherein the proximal end of the lateral SI implant comprises an adjustable threaded body configured to be threaded along a main body of the lateral SI implant to adjust the compression applied across the SI joint.

19. The method of claim 13, wherein the second insertion instrument comprises a first subassembly for engaging the distal end of the lateral SI implant with the cortical bone of the sacrum and a second subassembly for engaging the proximal end of the lateral SI implant with the ilium.

20. The method of claim 13, wherein the central section of the posterior SI implant further comprises a plurality of openings extending through the interior core region and connecting the lattice structure to the cannula.

* * * * *